US007510827B2

(12) United States Patent
Young

(10) Patent No.: US 7,510,827 B2
(45) Date of Patent: Mar. 31, 2009

(54) COMPOSITIONS AND METHODS FOR DETECTING CERTAIN FLAVIVIRUSES, INCLUDING MEMBERS OF THE JAPANESE ENCEPHALITIS VIRUS SEROGROUP

(75) Inventor: Karen K. Y. Young, San Ramon, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 432 days.

(21) Appl. No.: 10/815,480

(22) Filed: Mar. 31, 2004

(65) Prior Publication Data

US 2004/0229261 A1     Nov. 18, 2004

Related U.S. Application Data

(60) Provisional application No. 60/555,530, filed on Mar. 22, 2004, provisional application No. 60/552,454, filed on Mar. 12, 2004, provisional application No. 60/459,491, filed on Mar. 31, 2003.

(51) Int. Cl.
*C12Q 1/70*  (2006.01)
*C07H 21/00* (2006.01)
(52) U.S. Cl. .................. 435/5; 536/24.32; 536/24.33
(58) Field of Classification Search .............. 435/6, 435/194, 91.2, 286.1
See application file for complete search history.

(56) References Cited

U.S. PATENT DOCUMENTS

| | | | |
|---|---|---|---|
| 5,641,630 A | | 6/1997 | Snitman et al. |
| 6,001,611 A | * | 12/1999 | Will ........................ 435/91.2 |
| 6,040,166 A | * | 3/2000 | Erlich et al. ................ 435/194 |
| 7,115,374 B2 | * | 10/2006 | Linnen ......................... 435/6 |
| 7,132,233 B2 | * | 11/2006 | Shyamala ..................... 435/5 |

FOREIGN PATENT DOCUMENTS

| | | |
|---|---|---|
| GB | 2279954 A | 1/1995 |
| WO | WO 93/06214 A1 | 4/1993 |
| WO | WO 93/22440 A1 | 11/1993 |

OTHER PUBLICATIONS

Lanciotti et al., "Complete Genome Sequences and Phylogenetic Analysis of West Nile Virus Strains Isolated from the United States, Europe and the Middle East," Virology, 96-105 (2002).*
Rigler et al., "Fluorescence cross-correlation: A new concept for polymerase chain reaction," Journal of Biotechnology, 63 (1998) 97-109.*
Result No. 3 in 8.rge.*
Result 44 in 9.rge.*
Result 46 in 16.rge.*
Buck et al., "Design Strategies and Performance of Custom DNA Sequencing Primers," Biotechniques 27(3):528-536 (1999).*
Warrilow et al (Journal of Medical Virology 66:524-528, 2002).*
Fulop et al (Journal of Virological Methods 44:179-188, 1993).*
Pierre et al (Res. Virol. 145:93-104, 1994).*
Scaramozzino et al (Journal of Clinical Microbiology 39:1922-1927, 2001).*
Tanaka et al (Journal of Virological Methods 41:311-322, 1993).*
Olsthoorn et al (RNA 7:1370-1377, 2001).*
Rauscher et al (RNA 3:779-791, 1997).*
Lo et al (Journal of Virology 77:10004-10014, 2003).*
Batista et al (Virus Research 75:35-42, 2001).*
Wengler et al (Journal of General Virology 67:1183-1188, 1986).*
Beasley, David W.C. et al.; "Mouse Neuroinvasive Phenotype of West Nile Virus Strains Varies Depending upon Virus Genotype"; 2002, *Virology*, vol. 296, pp. 17-23.
Beasley, David W.C. et al.; EMBL: 2002, AF458347; XP002288984, 1 page.
Beasley, David W.C. et al.; EMBL: 2002, AF458348; XP002288985, 1 page.
Beasley, David W.C. et al.; EMBL: 2002, AF458350; XP002288986, 1 page.
Lanciotti, Robert S. et al.; "Rapid Detection of West Nile Virus from Human Clinical Specimens, Filed-Collected Mosquitoes, and Avian Samples by a TaqMan Reverse Transcriptase-PCR Assay"; 2000, *Journal of Clinical Microbiology*, vol. 38, No. 11, pp. 4066-4071.
Lanciotti, Robert S. et al.; "Nucleic Acid Sequence-Based Amplification Assays for Rapid Detection of West Nile and St. Louis Encephalitis Viruses"; 2001, *Journal of Clinical Microbiology*, vol. 39, No. 12, pp. 4506-4513.
Mansy, Frederic et al.; "A PCR based DNA hybridization capture system for the detection of human cytomegalovirus. A comparative study with other identification methods"; 1999, *Journal of Virological Methods*, vol. 80, pp. 113-122.
Nitsche, Andreas et al.; "Different Real-Time PCR Formats Compared for the Quantitative Detection of Human Cytomegalovirus DNA"; 1999, *Clinical Chemistry*, vol. 45, No. 11, pp. 1932-1937.
Tanaka, Mariko; "Rapid identification of flavivirus using the polymerase chain reaction"; 1993, *Journal of Virological Methods*, vol. 41, pp. 311-322.
Blatt, L. et al.; EMBL: ACN07332, XP-002300080, 1 page, date not available.
Ebel, G.D. et al.; EMBL: AY590194, XP-002300074, 1 page, 2004.
Ebel, G.D. et al.; EMBL: AY590195, XP-002300075, 1 page, 2004.
Holtmeier, W.; EMBL: HSU91175, XP-002300078, 2 pages, 2000.

(Continued)

*Primary Examiner*—Mary E Mosher
(74) *Attorney, Agent, or Firm*—Townsend and Townsend and Crew LLP

(57) ABSTRACT

The present invention provides rapid and accurate methods, primers, probes and kits for identifying the presence of a certain flaviviruses in a sample. Flaviviruses that can be detected include members of the Japanese encephalitis virus serogroup, Dengue virus, St Louis encephalitis virus, Montana myotis leukoencephalitis virus, Modoc virus, and Yellow Fever virus. The primers and probes of the invention can hybridize to regions in the 3' untranslated region of the viral genomes to be detected.

27 Claims, 22 Drawing Sheets

OTHER PUBLICATIONS

Jianrin, F. et al.; EMBL: AY590194, XP-002300074, 1 page, 2000.
Lai, C. et al.; EMBL: E06832, XP-002300081, 2 pages, date not available.
Lai, C. et al.; EMBL: AAQ38606, XP-002300077, 1 page, 2003.
Lai, C. et al.; EMBL: AAQ38605, XP-002300079, 1 page, 2003.
Lanciotti, R.S. et al.; EMBL: AF404753, XP-002300072, 2 pages, 2002.
Lanciotti, R.S. et al.; EMBL: AF404756, XP-002300073, 2 pages, 2002.
Morris, Timothy et al.; "Rapid Reverse Transcription-PCR Detection of Hepatitis C Virus RNA in Serum by Using the TaqMan Fluorogenic Detection System"; 1996, *Journal of Clinical Microbiology*, vol. 34, No. 12, pp. 2933-2936.
Takegami, T.; EMBL: AB051292, XP-002300071, 2 pages, 2001.
Tan, Y. et al.; EMBL: AAQ51476, XP-002300082, 4 pages, 2003.

\* cited by examiner

```
Kern217         TGG........C.........T.T.........AACCC.GCTGGGT GCA......C.....TT...A......G...GTCC.TGGCACGTAG.CTGGAGAGG.C
CoaV608         TGG........C.........T.T.........AATCC.GCTGGGT GCA......C.....TT...A......G...GTCC.TGGCACGTAG.CTGGAGAGG.C
TBH-28          TGG........T.........T.T.........AACCC.GCTGGGT GCA......C.....TT...A......G...GTCC.TGGCACGTAG.CCGGAGAGG.C
VR1265          TGG........T.........T.T.........AATCT.GCTGGGT GCA......C.....TT...A......G...GTCC.TGGCACGTAG.CTGGAG.GG.C
CoaV353                    T.........T.T.........AATCTAGCTGAGT GCA......C.....TT...A......G...GTCC.TGGCACGTAG.CTGGAGAGG.C
MVEV
VR77                                 .T.C........T.ATTCTCC.CGGTTG.A..................AG.AGT...TGCCAACAATGGAGATG.A
AF161266                             .T.C........T.ATTCTCT.CGGTTG.A..................AG.AGT...TGCCAACAATGGAGATG.A
M35172                               .T.C........T.ATTCTCC.CGGTTG.A..................AG.AGT...TGCCAACAATGGAGATG.A
L48972                               .T.C........T.ATTCTCC.CGGTTG.A..................AG.AGT...T.CCAACAATGGAGATG.A
L48973                               .T.C........T.ATTTTCC.CGGTTG.A..................AG.AGT...TGCCAACAATGGAGATG.A
L48974                               .T.C........T.ACTCTCT.CGGTTG.A........C.........AG.AG....TGCCAACAATGGAGATG.A
L48975                               .T.C......A.T.ACTCTCT.CGGTTG.A..................AG.AGT...TTCCAACAATGGAGATG.A
L48976                               .T.C........T.ATTCTCC.CGGTTG.A.......T..........AG.AGT...TGC.AACAATGGAGATG.A
Koutango virus
L48980                      ........C.....T.T...G.A........C....T....................G....T..TTC.......
```

| | | | | | | | |
|---|---|---|---|---|---|---|---|
| AY152187 | GT..CAT.TT.... | ....C......... | T.CCATCACTGACA... | CGCAGCA | AA.GGG..... | ....GAAGCC..GGAG. | ....CTC.T..T. | .....A.............CCCAACA.C... |
| AY152191 | GT..CAT.TT.... | ....C......... | ..CCATCACTGACA... | CGCAGCA | AA.GGG..... | ....GAAGCC..GGAG. | ....CTC.T..T. | .....A.............CCCAACA.C... |
| AY152195 | GT..CAT.TT.... | ....C......... | ..CCATCACTGACA... | CGCAGCA | AA.GGG..... | ....GAAGCC..GGAG. | ....CTC.T..T. | .....A.............CCCAACA.C... |
| AY152199 | GT..CAT.TT.... | ....C......... | ..CCATCACTGACA... | CGCAGCA | AA.GGG..... | ....GAAGCC..GGAG. | ....CTC.T..T. | ....TA.............CCCAACA.C... |
| AY152203 | GT..CAT.TT.... | ....C......... | ..CCATCACTGACA... | CGCAGCA | AA.GGG..... | ....GAAGCC..GGAG. | ....CTC.T..T. | .....A.............CCCAACA.C... |
| AY152207 | GT..CAT.TT.... | ....C......... | ..CCATCACTGACA... | CGCAGCA | AA.GGG..... | ....GAAGCC..GGAG. | ....CTC.T..T. | .....A.............CCCAACA.C... |
| AY152211 | GT..CAT.TT.... | ....C......... | ..CCATCACTGACA... | CGCAGCA | AA.GGG..... | ....GAAGCC..GGAG. | ....CTC.T..T. | .....A.............CCCAACA.C... |
| AY152215 | GT..CAT.TT.... | ....C......... | ..CCATCACTGACA... | CGCAGCA | AA.GGG..... | ....GAAGCC..GGAG. | ....CTC.T..T. | .....A.............CCCAACA.C... |
| AY152219 | GT..CAT.TT.... | ....C......... | ..CCATCACTGACA... | CGCAGCA | AA.GGG..... | ....GAAGCC..GGAG. | ....CTC.T..T. | .....A.............CCCAACA.C... |
| AY152223 | GT..CAT.TT.... | ....C......... | ..CCATCACTGACA... | CGCAGCA | AA.GGG..... | ....GAAGCC..GGAG. | ....CTC.T..T. | .....A.............CCCAACA.C... |
| AY152227 | GT..CAT.TT.... | ....C......... | ..CCATCACTGACA... | CGCAGCA | AA.GGG..... | ....GAAGCC..GGAG. | ....CTC.T..T. | .....A.............CCCAACA.C... |
| AY152231 | GT..CAT.TT.... | ....C......... | ..CCATCACTGACA... | CGCAGCA | AA.GGG..... | ....GAAGCC..GGAG. | ....CTC.T..T. | .....A.............CCCAACA.C... |
| AY152235 | GT..CAT.TT.... | ....C......... | ..CCATCACTGACA... | CGCAGCA | AA.GGG..... | ....GAAGCC..GGAG. | ....CTC.T..T. | .....A.............CCCAACA.C... |
| AY152239 | GT..CAT.TT.... | ....C......... | ..CCATCACTGACA... | CGCAGCA | AA.GGG..... | ....GAAGCC..GGAG. | ....CTC.T..T. | .....A.............CCCAACA.C... |
| AY152243 | GT..CAT.TT.... | ....T......... | ..CCATCACTGACA... | CGCAGCA | AA.GGG..... | ....GAAGCC..GGAG. | ....CTC.T..T. | .....A.............CCCAACA.C... |
| AY152247 | GT..CAT.TT.... | ....C......... | ..CCATCACTGACA... | CGCAGCA | AA.GGG..... | ....GANGCC..GGAG. | ....CTC.T..T. | .....A.............CCCAACA.C... |
| AY152251 | GT..CAT.TT.... | ....C......... | ..CCATCACTGACA... | UGCAGCA | AA.GGG..... | ....GAAGCC..GGAG. | ....CTC.T..T. | .....A.............CCCAACA.C... |
| AY152255 | GT..CAT.TT.... | ....C......... | ..CCATCACTGACA... | CGCAGCA | AA.GGG..... | ....GAAGCC..GGAG. | ....CTC.T..T. | .....A.............CCCAACA.C... |
| AY152259 | GT..CAT.TT.... | ....C......... | ..CCATCACTGACA... | CGCAGCA | AA.GGG..... | ....GAAGCC..GGAG. | ....CTC.T..T. | .....A.............CCCAACA.C... |
| AY152263 | GT..CAT.TT.... | ....C......... | ..CCATCACTGACA... | CGCAGCA | AA.GCG..... | ....GAAGCC..GGAG. | ....CTC.T..T. | .....A.............CCCAACA.C... |
| AY152267 | GT..CAT.TT.... | ....C......... | ..CCATCACTGACA... | CGCAGCA | AA.GGG..... | ....GAAGCC..GGAG. | ....CTC.T..T. | .....A.............CCCAACA.C... |
| AY152271 | GT..CAT.TT.... | ....C......... | ..CCATCACTGACA... | CGCAGCA | AAA.GGG.... | ....GAAGCC..GGAG. | ....CTC.T..T. | .....A.............CCCAACA.C... |
| AY152275 | GT..CAT.TT.... | ....C......... | ..CCATCACTGACA... | CGCAGCA | AA.GGG..... | ....GAAGCC..GGAG. | ....CTC.T..T. | .....A.............CCCAACA.C... |
| AY152279 | GT..CAT.TT.... | ....C......... | ..CCATCACTGACA... | CGCAGCA | AA.GGG..... | ....GAAGCC..GGAG. | ....CTC.T..T. | .....A.............CCCAACA.C... |
| AY152283 | GT..CAT.TT.... | ....C......... | ..CCATCACTGACA... | CGCAGCA | AA.GGG..... | ....GAAGCC..GGAG. | ....CTC.T..T. | .....A.............CCCAACA.C... |
| AY152287 | GT..CAT.TT.... | ....C......... | ..CCATCACTGACA... | CGCAGCA | AA.GGG..... | ....GAAGCC..GGAG. | ....CTC.T..T. | .....A.............CCCAACA.C... |
| AY152291 | GT..CAT.TT.... | ....C......... | ..CCATCACTGACA... | CGCAGCA | AA.GGG..... | ....GAAGCC..GGAG. | ....CTC.T..T. | .....A.............CCCAACA.C... |
| AY152295 | GT..CAT.TT.... | ....C......... | ..CCATCACTGACA... | ACGCA.. | AGA.GGG.... | ....GAAGCC..GGAG. | ....CTC.T..T. | .....A.............CCCAACA.C... |
| AY152299 | GT..CAT.TT.... | ....C......... | ..CCATCACTGACA... | CGCAGCA | AA.GGG..... | ....GAAGCC..GGAG. | ....CTC.T..T. | .....A.............CCCAACA.C... |
| AY152303 | GT..CAT.TT.... | ....C......... | ..CCATCACTGACA... | CGCAGCA | AA.GGG..... | ....GAAGCC..GGAG. | ....CTC.T..T. | .....A.............CCCAACA.C... |
| AY152307 | GT..CAT.TT.... | ....C......... | ..CCATCACTGACA... | CGCAGCA | AA.GGG..... | ....GAAGCC..GGAG. | ....CTC.T..T. | .....A.............CCCAACA.C... |
| AY152311 | GT..CAT.TT.... | ....C......... | ..CCATCACTGACA... | CGCAGCA | AA.GGG..... | ....CAAGCC..GGAG. | ....CTC.T..T. | .....A.............CCCAACA.C... |
| AY152315 | GT..CAT.TT.... | ....C......... | ..CCATCACTGACA... | CGCAGCA | AA.GGG..... | ....GAAGCC..GGAG. | ....CTC.T..T. | .....A.............CCCAACA.C... |
| AY152319 | GT..CAT.TT.... | ....C......... | ..CCATCACTGACA... | CGCAGCA | AA.GGG..... | ....GAAGCC..GGAG. | ....CTC.T..T. | .....A.............CCCAACA.C... |
| AY152323 | GT..CAT.TT.... | ....C......... | ..CCATCACTGACA... | CGCAGCA | AA.GGG..... | ....GAAGCC..GGAG. | ....CTC.T..T. | .....A.............CCCAACA.C... |
| AY152327 | GT..CAT.TT.... | ....C......... | ..CCATCACTGACA... | CGCAGCA | AA.GGG..... | ....GAAGCC..GGAG. | ....CTC.T..T. | .....A.............CCCAACA.C... |
| AY152331 | GT..CAT.TT.... | ....C......... | ..CCATCACTGACA... | CGCAGCA | AA.GGG..... | ....GAAGCC..GGAG. | ....CTC.T..T. | .....A.............CCCAACA.C... |
| AY152335 | GT..CAT.TT.... | ....C......... | ..CCATCACTGACA... | CGCAGCA | AA.GGG..... | ....GAAGCC..GGAG. | ....CTC.T..T. | .....A.............CCCAACA.C... |
| AY152339 | GT..CAT.TT.... | ....C......... | ..CCATCACTGACA... | CGCAGCA | AA.GGG..... | ....CAAGCC..GGAG. | ....CTC.T..T. | .....A.............CCCAACA.C... |
| AY152343 | GT..CAT.TT.... | ....C......... | ..CCATCACTGACA... | CGCAGCA | AA.GGG..... | ....GAAGCC..GGAG. | ....CTC.T..T. | .....A.............CCCAACA.C... |
| AY152347 | GT..CAT.TT.... | ....C......... | ..CCATCACTGACA... | CGCAGCA | AA.GGG..... | ....GAAGCC..GGAG. | ....CTC.T..T. | .....A.............CCCAACA.C... |
| AY152351 | GT..CAT.TT.... | ....C......... | ..CCATCACTGACA... | CGCAGCA | AA.GGG..... | ....GAAGCC..GGAG. | ....CTC.T..T. | .....A.............CCCAACA.C... |
| AY152355 | GT..TAT.TT.... | ....C......... | ..CCATCACTGACA... | CGCAGCA | AA.GGG..... | ....GAAGCC..GGAG. | ....CTC.T..T. | .....A.............CCCAACA.C... |
| AY152359 | GT..CAT.TT.... | ....C......... | ..CCATCACTGACA... | CGCAGCA | AA.GGG..... | ....GAGGCC..GGAG. | ....CTC.T..T. | .....A.............CCCAACA.C... |
| AY152363 | GT..CAT.TT.... | ....C......... | ..CCATCACTGACA... | CGCAGCA | AA.GGG..... | ....GAAGCC..GGAG. | ....CTC.T..T. | .....A.............CCCAACA.C... |
| AY152171 | GT..CAT.TT.... | ....C......... | ..CCATCACTGACA... | CGCAGCA | AA.GGG..... | ....GAAGCC..GGAG. | ....CTC.T..T. | .....A.............CCCAACA.C... |
| VR217-1 | GT..CAT.TT.... | ....C......... | ..CCATCACTGAACA.. | CGCAGCA | AAAGGGG.... | ....GAAGCC..GGAG. | ....CTC.T..T. | .....A.............CCCAACA.C... |

*Two potential binding sites for SEQ ID NOS.: 28 & 70 can be found in this region. These are denoted by single underline for SEQ ID NO.: 28, and shading for SEQ ID NO.: 70.

| | |
|---|---|
| KY1129 | 5'-GTAAGCC CTCAGAACCGTCTCGGAA-3' |

WNV
| | |
|---|---|
| AF317203 | ........  .................... |
| AF196835 | ........  .................... |
| AF260967 | ........  .................... |
| AF260968 | ........  .................... |
| AF260969 | ........  .................... |
| AF481864 | ........  .................... |
| M12294 | ........  .................... |
| AF206518 | ........  .................... |
| AF317203 | ........  .................... |
| AF202541 | ........  .................... |
| AF404757 | ........  .................... |
| AF404753 | ........  .................... |
| AF404754 | ........  .................... |
| AF404755 | ........  .................... |
| AF404756 | ........  .................... |
| AF017254 | ........  .................... |
| L48977 | ........  .................... |
| AF196536 | ........  .................... |
| AF196537 | ........  .................... |
| AF196538 | ........  .................... |
| AF196540 | ........  .................... |
| AF196541 | ........  .................... |
| AF196542 | ........  .................... |
| AF196543 | ........  .................... |
| AF458343 | ........  .C.................. |
| AF458344 | ........  .................... |
| AF458347 | ........  .................... |
| AF458348 | ........  .................... |
| AF458350 | ........  .................... |
| AF458352 | ........  ..........C........ |
| AF458353 | ........  .................... |
| AF458355 | ........  .................... |
| AF458358 | ........  .................... |
| AF458360 | ........  .................... |
| AF458361 | ........  .................... |
| AF208017 | ........  .................... |
| AF196539 | ........  .................... |
| AF196535 | ........  .................... |
| AF458359 | ........  .................... |
| AF458357 | ........  .................... |
| AF458354 | ........  .................... |
| AF458349 | ........  .................... |
| AF458345 | ........  .................... |
| AF458346 | ........T.............T...... |
| AF533540 | ........  .................... |

JEV
| | |
|---|---|
| AB051292 | .A.....  .................... |
| AF014160 | .A.....  .................... |
| AF014161 | .A.....  .................... |
| AF045551 | .A.....  .................... |
| AF069076 | .A.....  .................... |
| AF075723 | .A.....  .................... |
| AF080251 | .A.....  ....G............... |
| AF098735 | .A.....  .................... |
| AF098736 | .A.....  .................... |
| AF098737 | .A.....  .................... |
| AF217620 | .A.....  .................... |
| AF221499 | .A.....  .................... |
| AF221500 | .A.....  .................... |
| AF254452 | .A.....  .................... |
| AF254453 | .A.....  .................... |
| AF315119 | .A.....  ..........T......... |
| AF416457 | .A.....  .................... |
| AF486638 | .A.....  .................... |
| U14163 | .A.....  .................... |
| U15763 | .A.....  .................... |

Fig. 4A

| | |
|---|---|
| KY1129 | 5'-GTAAGCC CTCAGAACCGTCTCGGAA-3' |
| JEV cont. | |
| L48961 | .A..... .................. |
| U47032 | .A..... .................. |
| M18370 | .A..... .................. |
| M55506 | .A..... .................. |
| L78128 | .A..... .................. |
| D90195 | .A..... .................. |
| D90194 | .A..... .................. |
| AF311748 | .A..... .................. |
| AF092550 | .A..... .................. |
| AF092552 | .A..... .................. |
| AF092553 | .A..... .................. |
| AF139531 | .A..... .................. |
| AF148900 | .A..... .................. |
| AF148902 | .A..... .................. |
| AF218068 | .A..... .................. |
| AF289816 | .A..... .................. |
| AF318291 | .A..... .................. |
| L48967 | .A..... .................. |
| L48968 | .A..C.. .................. |
| L54067 | .A..... .................. |
| L54068 | .A..... .................. |
| L54069 | .A..... .................. |
| L54070 | .A..... .................. |
| L54072 | .A..... .................. |
| L54122 | .A..... .................. |
| L54123 | .A..... .................. |
| AF306514 | .A..... .................. |
| AF306515 | .A..... ...........T...... |
| AF306516 | .A..... ...........T...... |
| AF306517 | .A..... ....A......T...... |
| MVEV | |
| AF161266 | .A.....T.C................ |
| M35172 | .A.....T.C................ |
| L48972 | .A.....T.C................ |
| L48973 | .A.....T.C................ |
| L48974 | .A.....T.C....C........... |
| L48975 | .A.....T.C................ |
| L48976 | .A.....T.C.........C...... |
| KUNJIN | |
| AF458351 | ....... ................G. |
| AF458356 | ....... .................. |
| AF297840 | ....... ..........C....... |
| AF297841 | ....... .................. |
| AF298942 | ....... .................. |
| AF297843 | ....... .................. |
| AF297844 | ....... .................. |
| AF297845 | ....... .................. |
| AF297846 | ....... ..........C....... |
| AF297847 | ....... ..........C....... |
| AF297848 | ....... .................. |
| AF297849 | ....... .................. |
| AF297850 | ....... ..........C....... |
| AF297851 | ....... ..........C.....GT |
| AF297852 | ....... ..........C....... |
| AF297853 | ....... ..........C....... |
| AF297854 | ....... .................. |
| AF297855 | ....... .................. |
| AF297856 | ....... .................. |
| AF297857 | ........G................. |
| AF297858 | ....... .................. |
| AF297859 | ....... .................. |
| L48978 | ....... .................. |
| L49311 | ....... .................. |
| D00246 | ....... .................. |
| L48979 | ....... .................. |
| L24512 | ....... .................. |
| KOUTANGO | |
| L48980 | ....... .................. |

Fig. 4B

| KY1130 | 5'-TCCTAGTCTA TCCCAGGTGTCAA-3' |
|---|---|
| WNV | |
| AF196835 | .......... .............. |
| AF260967 | .......... .............. |
| AF260968 | .......... .............. |
| AF260969 | .......... .............. |
| AF481864 | .......... .............. |
| M12294 | C......... .............. |
| AF206518 | .......... .............. |
| AF317203 | .......... .............. |
| AF202541 | .......... .............. |
| AF404757 | .......... .............. |
| AF404753 | .......... .............. |
| AF404754 | .......... .............. |
| AF404755 | .......... .............. |
| AF404756 | .......... .............. |
| AF017254 | .......... .......A..... |
| Kunjin | |
| L24512 | .......... .............. |
| JEV | |
| AB051292 | ...C......T.............. |
| AF014160 | ...C......T.............. |
| AF014161 | ...C......T.............. |
| AF045551 | ...C.C....T.............. |
| AF069076 | ...C......T.............. |
| AF075723 | ...C......T.............. |
| AF080251 | ...C......T.............. |
| AF098735 | ...C......T.............. |
| AF098736 | ...C......T.............. |
| AF098737 | ...C......TCT............ |
| AF217620 | ...C......T.............. |
| AF221499 | ...C......T.............. |
| AF221500 | ...C......T.............. |
| AF254452 | ...C......T.............. |
| AF254453 | ...C......T.............. |
| AF315119 | ...C......T.............. |
| AF416457 | ...C......T.............. |
| AF486638 | ...C...A..T.............. |
| U14163 | ...C......T.............. |
| U15763 | ...C......T.............. |
| L48961 | ...C......T.............. |
| U47032 | ..........T.............. |
| M18370 | ...C......T.............. |
| M55506 | ...C......T.............. |
| L78128 | ...C......T.............. |
| D90195 | ...C......T.............. |
| D90194 | ...C......T.............. |
| AF311748 | ...C......T.............. |
| AF306514 | ...C.C....T.............. |
| AF306515 | ...C......T.............. |
| AF306516 | ...C......T.............. |
| AF306517 | ...C.C....T.............. |
| D00037 | ...C......T.............. |
| M14933 | ...C......T.............. |
| MVEV | |
| AF161266 | ........TT.............. |
| M35172 | ........TT.............. |

Fig. 4C

| | |
|---|---|
| KY1131 | 5'-GGACTAGAGGTTAGAGGAGACCCCGCGG-3' |
| WNV | |
| AF196835 | ............................ |
| AF260967 | ............................ |
| AF260968 | ............................ |
| AF260969 | ............................ |
| AF481864 | ............................ |
| M12294 | ...........................T |
| AF206518 | ............................ |
| AF317203 | ............................ |
| AF202541 | ............................ |
| AF404757 | ............................ |
| AF404753 | ............................ |
| AF404754 | ............................ |
| AF404755 | ............................ |
| AF404756 | ............................ |
| AF017254 | ............................ |
| AF208017 | ......T................A..T |
| | |
| Kunjin | |
| L24512 | ...........................T |
| | |
| JEV | |
| AB051292 | ..........................T.. |
| AF014160 | ..........................T.. |
| AF014161 | ..........................T.. |
| AF045551 | ..........................T.. |
| AF069076 | ..........................T.. |
| AF075723 | ..........................T.. |
| AF080251 | ..........................T.. |
| AF098735 | ..........................T.. |
| AF098736 | ..........................T.. |
| AF098737 | ..........................T.. |
| AF217620 | ..........................T.. |
| AF221499 | ..........................T.. |
| AF221500 | ..........................T.. |
| AF254452 | ..........................T.. |
| AF254453 | ..........................T.. |
| AF315119 | ..........................T.. |
| AF416457 | ..........................T.. |
| AF486638 | ..........................T.. |
| U14163 | ..........................T.. |
| U15763 | ..........................T.. |
| L48961 | ..........................T.. |
| U47032 | ..........................T.. |
| M18370 | ..........................T.. |
| M55506 | ..........................T.. |
| L78128 | ..........................T.. |
| D90195 | ..........................T.. |
| D90194 | ..........................T.. |
| AF311748 | ..........................T.. |
| AF306514 | ..........................T.. |
| AF306515 | ..........................T.. |
| AF306516 | ..........................T.. |
| AF306517 | ..........................T.. |
| | |
| MVEV | |
| AF161266 | .......................A.TC |
| M35172 | .......................A.TC |

Fig. 4D

```
KY1131     5'-GGACTAGAGGTTAGAGGAGACCCCGCGG-3'

DENGUE

```
KY1131       5'-GGACTAGAGGTTAGAGGAGACCCCGCGG-3'

DENGUE,cont.
U88537                  ........................C..C
AF038403                ........................C.CA
AF326826                ........................C.CA
AF326827                ........................C.CA MONTANA MYOTIS LEUKOENCEPHALITIS VIRUS
NC_004119               ........................TTCC

MODOC VIRUS
NC_003635               ........................CG.C

YELLOW FEVER VIRUS
X03700                  ..T.....................TC.A.
U52393                  ..T.....................TC.A.
U52407                  ..T.....................TC.A.
AF052448                ..T.....................TC.A.
```

Amplification of WNV RNA Dilutions

Legend:
- Neg -1.00 — Neg -1.00
- 1.00E-02 32.10 — 1.00E-02 32.19
- 1.00E-03 35.72 — 1.00E-03 35.66
- 1.00E-04 39.02 — 1.00E-04 39.06
- 1.00E-05 42.76 — 1.00E-05 42.70
- 1.00E-06 46.82 — 1.00E-06 45.87
- 1.00E-07 -1.00 — 1.00E-07 -1.00

X-axis: Cycles (0 to 60)
Y-axis: Normalized Fluorescence (-1.00 to 6.00)

Figure 7

```
BFS1750     TTGCCACCGGATGTCAGTGTAAACGGTGCTGTCTGTAACCTGGCCCCAGTGACTGGGTTATCAAAGCCAATCTGCCCGAGTGCAAAGCCC  90
1750-Std    ..........................................................................................
TD6-4G      ..........................................................................................
CoaV750     ............................C.............................................T.............
L695121.05  ............................C..............................C............................
TNM771K     .........................................................................................
MSI-7       ..................................................................C....................C.
Kern217     ..................................................................C..............C.C.T.G.
CoaV608     ..................................................................C..............C.C

Figure 7 – cont.

```
                 ACTAGAGGTTAGAGGAGGACCCCGCTGCAACTTGGCAAGGCCCAAACCCGCTCGAAGCTGTGTAGAGACGGGGGAAGGACTAGAGGTTAGAGG  360
BFS1750          ..........................................................................................
1750-Std         ..........................................................................................
TD6-4G           ...............................C..........................................................
CoaV750          ...............................C..........................A...............................
L695121.05       .................T.............................................T..........................
TNM771K          .................T.............................................T..........................
MSI-7            .................T.............................................T..........................
Kern217          .................T........................................A...............................
C

COMPOSITIONS AND METHODS FOR DETECTING CERTAIN FLAVIVIRUSES, INCLUDING MEMBERS OF THE JAPANESE ENCEPHALITIS VIRUS SEROGROUP

CROSS-REFERENCE TO RELATED PATENT APPLICATIONS

The present application claims benefit of priority to the following applications: U.S. Provisional Patent Application No. 60/459,491, filed Mar. 31, 2003; U.S. Provisional Patent Application No. 60/552,454, filed Mar. 12, 2004; and U.S. Provisional Patent Application No. 60/555,530, filed Mar. 22, 2004, each of which is incorporated by reference in their entirety for any purpose.

BACKGROUND OF THE INVENTION

The family Flaviviridae and genus Flavivirus encompasses a number of viruses that are potentially lethal human pathogens. Such viruses include Dengue virus, Yellow Fever virus, Modoc virus, and viruses of the Japanese encephalitis virus serogroup. The Japanese encephalitis virus serogroup includes several closely related viruses, such as Japanese encephalitis virus (JEV), West Nile virus (WNV), St. Louis encephalitis virus, Murray Valley encephalitis virus, and Kunjin virus. Kunjin virus is often referred to as a variant of WNV because of the degree of sequence conservation between these two viruses. Characterized WNV strains have been divided into two groups, lineage I and lineage II, based on sequence analysis.

In 1999, the first case of human WNV infection in the U.S. was reported. Since then, annual epidemics have occurred. In August 2002, transmission of WNV via routes other than mosquito bites was confirmed when four organ recipients were infected by a single organ donor. The virus has since been found to be transmissible by transfusion of blood products (21 confirmed cases) and by breast milk.

Detection of active WNV infection is difficult, as symptoms are non-specific and virus-specific antibodies can usually be detected only after the viremic phase. Furthermore, WNV-specific IgM can persist for more than a year, making it difficult to differentiate between active infection and past exposure. More sensitive detection methods, such as direct detection of viral nucleic acids, are needed. Detection of viral nucleic acids presents a more sensitive method for the early detection of infection by WNV and other flaviviruses than serological methods currently in use.

Other flaviviruses, including members of the Japanese encephalitis virus serogroup, are also human pathogens. These pathogens include Japanese encephalitis serogroup members such as Japanese encephalitis virus, St. Louis encephalitis virus (SLEV), and Murray Valley encephalitis virus, and other flaviviruses such as Dengue virus, Yellow Fever virus, and Modoc virus. Transmission of members of the Japanese encephalitis virus serogroup other than WNV via blood products remains undocumented. However, such transmissions are possible, and increasingly likely to occur as these viruses become more widespread. Therefore, new, sensitive, and specific assays that are capable of detecting these flaviviruses that are human pathogens are highly desirable. Furthermore, a single assay that is capable of detecting several members of the Japanese encephalitis serogroup would also be very desirable.

BRIEF SUMMARY OF THE INVENTION

The present invention provides compositions, methods, and kits for detecting the presence of a nucleic acid of certain flaviviruses, including several members of the Japanese encephalitis virus serogroup. The compositions and methods of the present invention are based, in part, on the discovery of oligonucleotides that can be used e.g., as primers and probes to detect the presence of members of the Japanese encephalitis virus serogroup. For example, West Nile virus, Kunjin virus, Japanese encephalitis virus, St Louis encephalitis virus (SLEV) and Murray Valley encephalitis virus can be detected with the oligonucleotides of the invention. Further, the oligonucleotides of the invention can be used to detect flaviviruses outside the Japanese encephalitis virus serogroup, including, for example, Dengue virus, Montana myotis leukoencephalitis virus, Modoc virus, and Yellow Fever virus. The oligonucleotides of the invention can be used as primers and probes to detect these flaviviruses according to the methods described herein.

In certain aspects, the invention provides a method for detecting a nucleic acid of several members of the Japanese encephalitis virus serogroup. In the method, a detectably-labeled oligonucleotide of the invention, described in detail below, is used as a probe to detect a nucleic acid of several members of the Japanese encephalitis virus serogroup. The probe hybridizes to a nucleic acid of SEQ ID NO.: 16 or the complement thereof, which is a sequence of a conserved region in the 3' untranslated region of flaviviral nucleic acids that can be detected according to the present invention. In certain embodiments of the invention, a template-dependent nucleic acid polymerase with 5'-3' exonuclease activity fragments the probe, wherein fragmentation of the detectably-labeled probe indicates the presence of the nucleic acid of a member of the Japanese encephalitis serogroup.

In certain embodiments, the methods comprise amplifying the nucleic acid of a member of the Japanese encephalitis virus serogroup in the presence of a detectably-labeled oligonucleotide, wherein the detectably-labeled oligonucleotide comprises at least 20 consecutive nucleotides of SEQ ID NO.: 17, or the complement thereof. In other embodiments, the methods comprise amplifying the nucleic acid of a member of the Japanese encephalitis virus serogroup in the presence of a detectably-labeled oligonucleotide, wherein the detectably-labeled oligonucleotide comprises SEQ ID NO.: 18, or the complement thereof. SEQ ID NO.: 18 is an oligonucleotide sequence that hybridizes to a conserved region of currently known flaviviral nucleic acids that can be detected according to the present invention. In still other embodiments, the methods comprise amplifying the nucleic acid of a member of the Japanese encephalitis virus serogroup in the presence of a detectably-labeled nucleic acid probe, wherein the detectably-labeled probe comprises SEQ ID NO.: 28, or the complement thereof. SEQ ID NO.: 28 is a specific probe nucleic acid sequence that can be used to detect flaviviruses according to the present invention.

In certain embodiments, the probe comprises a detectable moiety. The detectable moiety can be any detectable moiety known to one of skill in the art without limitation. For example, the detectable moiety can be a fluorescent moiety. In certain embodiments, the fluorescent moiety can be selected from the group consisting of fluorescein-family dyes, polyhalofluorescein-family dyes, hexachlorofluorescein-family dyes, coumarin-family dyes, rhodamine-family dyes, cyanine-family dyes, oxazine-family dyes, thiazine-family dyes, squaraine-family dyes, chelated lanthanide-family dyes, and BODIPY®-family dyes. In a preferred embodiment, the fluorescent moiety is 6-carboxyfluorescein.

In certain embodiments, the probe comprises a quencher moiety. The quencher moiety can be any quencher moiety known to one of skill in the art without limitation. In certain embodiments, the quencher moiety can be selected from the group consisting of fluorescein-family dyes, polyhalofluorescein-family dyes, hexachlorofluorescein-family dyes, coumarin-family dyes, rhodamine-family dyes, cyanine-family dyes, oxazine-family dyes, thiazine-family dyes, squaraine-family dyes, chelated lanthanide-family dyes, BODIPY®-family dyes, and non-fluorescent quencher moieties. In certain embodiments, the non-fluorescent quencher moieties can be BHQ™-family dyes, Iowa Black™, or Dabcyl. In a preferred embodiment, the quencher moiety is Cy5™.

In certain aspects, a nucleic acid of a member of the Japanese encephalitis virus serogroup can be detected with an oligonucleotide of the invention. In certain embodiments, a first oligonucleotide that hybridizes to a nucleic acid of SEQ ID NO.: 1 can be used as a primer to amplify a nucleic acid of a member of the Japanese encephalitis virus serogroup. SEQ ID NO.: 1 is based on the discovery of sequences conserved among members of the Japanese encephalitis virus serogroup that can be detected according to the present invention. In certain embodiments, the first primer comprises at least 16 consecutive nucleotides of SEQ ID NO.: 2. In other embodiments, the first primer comprises SEQ ID NO.: 3. SEQ ID NO.: 3 is a primer sequence based on the discovery of a conserved region of all currently known sequences from Japanese encephalitis virus serogroup members that can be detected according to the present invention. In still other embodiments, the first primer comprises SEQ ID NO.: 8. SEQ ID NO.: 8 is a specific primer sequence that can be used to amplify Japanese encephalitis serogroup member nucleic acids according to the present invention.

In certain embodiments, a second oligonucleotide that hybridizes to a nucleic acid of SEQ ID NO.: 9 can be used as a primer to amplify a nucleic acid of a member of the Japanese encephalitis virus serogroup. SEQ ID NO.: 9 is a consensus sequence based on the discovery of sequences conserved among members of the Japanese encephalitis virus serogroup that can be detected according to the present invention. In certain embodiments, the second primer comprises at least 16 consecutive nucleotides of SEQ ID NO.: 10. SEQ ID NO.: 10 is the complement to SEQ ID NO.: 9. In other embodiments, the second primer comprises SEQ ID NO.: 11. SEQ ID NO.: 11 is a primer sequence based on the discovery of a conserved region of all currently known sequences from Japanese encephalitis virus serogroup members that can be detected according to the present invention. In yet other embodiments, the second primer comprises SEQ ID NO.: 15 or SEQ ID NO:74. SEQ ID NO.: 15 and SEQ ID NO:74 are specific primer sequences that can be used to amplify Japanese encephalitis serogroup member nucleic acids according to the present invention. In certain embodiments, the first and second primers can be used together in methods of detecting a nucleic acid of a member of the Japanese encephalitis serogroup.

In certain embodiments, the methods comprise amplifying the nucleic acid of a member of the Japanese encephalitis virus serogroup in the presence of a detectably-labeled nucleic acid probe which comprises a fluorescent moiety and a quencher moiety. In certain embodiments, fragmentation of the detectably-labeled probe by a template-dependent nucleic acid polymerase with 5'-3' nuclease activity separates the fluorescent moiety from the quencher moiety. In certain embodiments, the fragmentation of the probe and thus the presence of the nucleic acid of the a member of the Japanese encephalitis virus serogroup can be detected by monitoring emission of fluorescence.

In certain embodiments, a nucleic acid of a member of the Japanese encephalitis serogroup can be detected by hybridizing the nucleic acid to a primer or probe of the invention that is covalently linked to a solid support. In certain embodiments, the nucleic acid can be detected by hybridizing a detectably-labeled primer or probe to the nucleic acid. In other embodiments, the nucleic acid can be directly detected by incorporating detectable moieties into the nucleic acid.

In other embodiments, a nucleic acid of a member of the Japanese encephalitis serogroup can be detected using a nanoparticle with two or more primers or probes of the invention covalently linked thereto. In still other embodiments, a nucleic acid of a member of the Japanese encephalitis serogroup can be detected using a rolling circle amplification assay with primers and/or probes of the invention. In yet other embodiments, a nucleic acid of a member of the Japanese encephalitis serogroup can be detected using a Strand Displacement Amplification assay with two primers of the invention. In still other embodiments, a nucleic acid of a member of the Japanese encephalitis serogroup can be detected using a transcription-mediated amplification assay using primers and/or probes of the invention. In yet another embodiment, a nucleic acid of a member of the Japanese encephalitis serogroup can be detected using a nucleic acid sequence-based amplification (NASBA) assay, using the primers and/or probes of the invention. In yet another embodiment, a nucleic acid of a member of the Japanese encephalitis serogroup can be detected using diagnostic PCR with primers and/or probes of the invention.

In certain embodiments, the first and second primers and a probe of the invention can be used together in methods of detecting a member of the Japanese encephalitis serogroup. In certain embodiments, a nucleic acid of a member of the Japanese encephalitis serogroup can be detected using a probe of the invention that comprises a molecular beacon. In other embodiments, a nucleic acid of a member of the Japanese encephalitis serogroup can be detected using a nucleic acid sequenced-based amplification assay with primers and/or probes of the invention. In yet other embodiments, a nucleic acid of a member of the Japanese encephalitis serogroup can be detected by amplifying the nucleic acid with two primers of the invention, then detecting the nucleic acid with a detectably-labeled probe of the invention. In certain embodiments, a nucleic acid of a member of the Japanese encephalitis serogroup can be detected using a dot blot assay with primers and/or probes of the invention. In other embodiments, a nucleic acid of a member of the Japanese encephalitis serogroup can be detected using a reverse dot blot assay with primers and/or probes of the invention. In still other embodiments, a nucleic acid of a member of the Japanese encephalitis serogroup can be detected using a multivalent probe such as a dendrimer.

In addition to the foregoing methods, the present invention further provides nucleic acid primers and probes for detecting a nucleic acid of a member of the Japanese encephalitis serogroup. In certain aspects, the invention provides a nucleic acid primer for detecting a member of the Japanese encephalitis virus serogroup. In certain embodiments, the primer comprises a nucleic acid that hybridizes to a nucleic acid of SEQ ID NO.: 1. In certain embodiments, the nucleic acid primer comprises at least 16 consecutive nucleotides of SEQ ID NO.:

2. In other embodiments, the nucleic acid primer comprises SEQ ID NO.: 3. In still other embodiments, the nucleic acid primer comprises SEQ ID NO.: 8.

In certain embodiments, the nucleic acid primer comprises $N^6$-alkyl-deoxyadenosine at position 24 of SEQ ID NO.: 8. In a specific embodiment, the nucleic acid primer comprises $N^6$-methyl-deoxyadenosine at position 24 of SEQ ID NO.: 8. In certain embodiments, the nucleic acid primer comprises $N^6$-alkyl-deoxyadenosine at position 25 of SEQ ID NO.: 8. In a specific embodiment, the nucleic acid primer comprises $N^6$-tert-butyl-benzyl-deoxyadenosine at position 25 of SEQ ID NO.: 8. In certain embodiments, the nucleic acid primer comprises $N^6$-alkyl-deoxyadenosine at positions 24 and 25 of SEQ ID NO.: 8. In still another specific embodiment, the nucleic acid primer comprises $N^6$-methyl-deoxyadenosine at position 24 of SEQ ID NO.: 8 and $N^6$-tert-butyl-benzyl-deoxyadenosine at position 25 of SEQ ID NO.: 8.

In certain embodiments, the invention provides a nucleic acid primer for detecting a member of the Japanese encephalitis virus serogroup. In certain embodiments, the primer comprises a nucleic acid that hybridizes to a nucleic acid of SEQ ID NO.: 9. In other embodiments, the nucleic acid primer comprises at least 16 consecutive nucleotides of SEQ ID NO.: 10. In still other embodiments, the nucleic acid primer comprises SEQ ID NO.: 11. In yet other embodiments, the nucleic acid primer comprises SEQ ID NO.: 15 or SEQ ID NO:74. In certain embodiments, the nucleic acid primer comprises $N^6$-alkyl-deoxyadenosine at position 23 of SEQ ID NO.: 15 or at position 25 of SEQ ID NO:74. In a specific embodiment, the nucleic acid primer comprises $N^6$-tert-butyl-benzyl-deoxyadenosine at position 23 of SEQ ID NO.: 15 or at position 25 of SEQ ID NO:74.

In other aspects, the invention provides a nucleic acid probe for detecting a nucleic acid of a flavivirus. Flavivirus nucleic acids that can be detect with the probe include, for example, members of the Japanese encephalitis virus serogroup, Dengue virus, Yellow Fever virus, Montana myotis leukencephalitis virus, and Modoc virus. In certain embodiments, the probe comprises a nucleic acid that hybridizes to a nucleic acid of SEQ ID NO.: 16, or the complement thereof. In certain embodiments, the nucleic acid probe comprises at least 20 consecutive nucleotides of SEQ ID NO.: 17, or the complement thereof. In other embodiments, the nucleic acid probe comprises SEQ ID NO.: 18, or the complement thereof. In still other embodiments, the nucleic acid probe comprises SEQ ID NO.: 28, or the complement thereof.

In certain embodiments, the invention provides a nucleic acid probe comprising a fluorescent moiety and a quencher moiety. In certain embodiments, the fluorescent moiety is positioned relative to the quencher moiety such that a photon emitted by the fluorescent moiety is absorbed by the quencher moiety when the probe is intact. Fragmentation of the probe by an enzyme with 5' nuclease activity separates the fluorescent moiety from the quencher moiety such that a photon emitted by the fluorescent moiety can be detected.

In other aspects, the invention provides a kit for the detection of a nucleic acid of a member of the Japanese encephalitis virus serogroup. In certain embodiments, the kit comprises an oligonucleotide of the invention. In further embodiments, the kit comprises a combination of one or more of the primers and probes of the invention. For example, in one embodiment the kit comprises a first nucleic acid primer that hybridizes to a nucleic acid of SEQ ID NO.: 1; a second nucleic acid primer that hybridizes to a nucleic acid of SEQ ID NO.: 9; and a nucleic acid probe that hybridizes to a nucleic acid of SEQ ID NO.: 16, or the complement thereof.

In certain embodiments, the first nucleic acid primer of the kits of the invention comprises at least 16 consecutive nucleotides of SEQ ID NO.: 2. In other embodiments, the first nucleic acid primer comprises SEQ ID NO.: 3. In yet other embodiments, the first nucleic acid primer comprises SEQ ID NO.: 8. In certain embodiments, the first nucleic acid primer comprises $N^6$-alkyl-deoxyadenosine at position 24 of SEQ ID NO.: 8. In a specific embodiment, the first nucleic acid primer comprises $N^6$-methyl-deoxyadenosine at position 24 of SEQ ID NO.: 8. In certain embodiments, the first nucleic acid primer comprises $N^6$-alkyl-deoxyadenosine at position 25 of SEQ ID NO.: 8. In a specific embodiment, the first nucleic acid primer comprises $N^6$-tert-butyl-benzyl-deoxyadenosine at position 25 of SEQ ID NO.: 8. In certain embodiments, the first nucleic acid primer comprises $N^6$-alkyl-deoxyadenosine at positions 24 and 25 of SEQ ID NO.: 8. In still another specific embodiment, the first nucleic acid primer comprises $N^6$-methyl-deoxyadenosine at position 24 of SEQ ID NO.: 8 and $N^6$-tert-butyl-benzyl-deoxyadenosine at position 25 of SEQ ID NO.: 8.

In certain embodiments, the second nucleic acid primer of the kits of the invention comprises at least 16 consecutive nucleotides of SEQ ID NO.: 10. In other embodiments, the second nucleic acid primer comprises SEQ ID NO.: 11. In still other embodiments, the second nucleic acid primer comprises SEQ ID NO.: 15 or SEQ ID NO:74. In certain embodiments, the second nucleic acid primer comprises $N^6$-alkyl-deoxyadenosine at position 23 of SEQ ID NO.: 15 or at position 25 of SEQ ID NO:74. In a specific embodiment, the second nucleic acid primer comprises $N^6$-tert-butyl-benzyl-deoxyadenosine at position 23 of SEQ ID NO.: 15 or at position 25 of SEQ ID NO:74.

In certain embodiments, the nucleic acid probe of the kits of the invention comprises at least 20 consecutive nucleotides of SEQ ID NO.: 17, or the complement thereof. In other embodiments, the nucleic acid probe comprises SEQ ID NO.: 18, or the complement thereof. In still other embodiments, the nucleic acid probe comprises SEQ ID NO.: 28, or the complement thereof.

In certain embodiments, the kits of the invention comprise an oligonucleotide useful as a nucleic acid probe, wherein one or more detectable moieties is attached to the nucleic acid probe. In certain embodiments, the one or more detectable moieties is a fluorescent moiety. In certain embodiments, the fluorescent moiety can be selected from the group consisting of fluorescein-family dyes, polyhalofluorescein-family dyes, hexachlorofluorescein-family dyes, coumarin-family dyes, rhodamine-family dyes, cyanine-family dyes, oxazine-family dyes, thiazine-family dyes, squaraine-family dyes, chelated lanthanide-family dyes, and BODIPY®-family dyes. In a preferred embodiment, the fluorescent moiety is 6-carboxyfluorescein.

In certain embodiments, the kits of the invention comprise an oligonucleotide useful as a nucleic acid probe, wherein at least one quencher moiety is attached to the nucleic acid probe. In certain embodiments, the quencher moiety can be selected from the group consisting of fluorescein-family dyes, polyhalofluorescein-family dyes, hexachlorofluorescein-family dyes, coumarin-family dyes, rhodamine-family dyes, cyanine-family dyes, oxazine-family dyes, thiazine-family dyes, squaraine-family dyes, chelated lanthanide-family dyes, BODIPY®-family dyes, and non-fluorescent quencher moieties. In certain embodiments, the non-fluorescent quencher moieties can be BHQ™-family dyes, Iowa Black™, or Dabcyl. In a preferred embodiment, the quencher moiety is Cy5™. In other embodiments, the probe comprises at least one detectable moiety, e.g. a fluorescent moiety and at least one quencher moiety.

In certain embodiments, the kits of invention comprise a thermostable DNA polymerase. In certain embodiments, the thermostable DNA polymerase has reverse transcription activity. In certain embodiments, the kits of the invention additionally comprise instructions for detecting a nucleic acid of a member of the Japanese encephalitis virus serogroup according to the methods of the invention.

The present invention also provides isolated polynucleotides comprising SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, or SEQ ID NO:40.

The present invention also provides vectors comprising a polynucleotide comprising SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, or SEQ ID NO:40.

The present invention also provides oligonucleotides comprising a sequence of at least 10 contiguous nucleotides that hybridizes to SEQ ID NO:29 or a complement thereof, SEQ ID NO:30 or a complement thereof, SEQ ID NO:31 or a complement thereof, SEQ ID NO:32 or a complement thereof, SEQ ID NO:33 or a complement thereof, SEQ ID NO:34 or a complement thereof, SEQ ID NO:35 or a complement thereof, SEQ ID NO:36 or a complement thereof, SEQ ID NO:37 or a complement thereof, SEQ ID NO:38 or a complement thereof, SEQ ID NO:39 or a complement thereof, SEQ ID NO:40 or a complement thereof. In some embodiments, the oligonucleotide hybridizes to SEQ ID NO: 68 or a complement of SEQ ID NO:69. In some embodiments, the oligonucleotide comprises a sequence selected from the group consisting of SEQ ID NO:64, SEQ ID NO:65, SEQ ID NO:66, and SEQ ID NO:67. In some embodiments, the oligonucleotide is selected from the group consisting of SEQ ID NO:64, SEQ ID NO:65, SEQ ID NO:66, and SEQ ID NO:67. In some embodiments, the oligonucleotide has fewer than 100 nucleotides.

The present invention also provides reaction mixtures comprising an oligonucleotide comprising a nucleotide sequence that hybridizes to SEQ ID NO:29 or a complement thereof, SEQ ID NO:30 or a complement thereof, SEQ ID NO:31 or a complement thereof, SEQ ID NO:32 or a complement thereof, SEQ ID NO:33 or a complement thereof, SEQ ID NO:34 or a complement thereof, SEQ ID NO:35 or a complement thereof, SEQ ID NO:36 or a complement thereof, SEQ ID NO:37 or a complement thereof, SEQ ID NO:38 or a complement thereof, SEQ ID NO:39 or a complement thereof, SEQ ID NO:40 or a complement thereof.

In some embodiments, the oligonucleotide hybridizes to SEQ ID NO: 68 or a complement of SEQ ID NO:69. In some embodiments, the oligonucleotide comprises a sequence selected from the group consisting of SEQ ID NO:64, SEQ ID NO:65, SEQ ID NO:66, and SEQ ID NO:67. In some embodiments, the oligonucleotide is selected from the group consisting of SEQ ID NO:64, SEQ ID NO:65, SEQ ID NO:66, and SEQ ID NO:67.

In some embodiments, the reaction mixtures comprise an oligonucleotide selected from the group consisting of SEQ ID NO:64 and SEQ ID NO:65; and an oligonucleotide selected from the group consisting of SEQ ID NO:66 and SEQ ID NO:67. In some embodiments, the oligonucleotide has fewer than 100 nucleotides. In some embodiments, the reaction mixtures further comprise a detectably-labeled oligonucleotide that hybridizes to SEQ ID NO:16 or a complement thereof.

In some embodiments, the reaction mixture comprises a DNA polymerase.

In some embodiments, the detectably-labeled oligonucleotide comprises at least 20 consecutive nucleotides of SEQ ID NO.:17, or the complement thereof. In some embodiments, the detectably-labeled oligonucleotide comprises SEQ ID NO.:28, or the complement thereof. In some embodiments, the detectably-labeled oligonucleotide comprises a fluorescent moiety. In some embodiments, the detectably-labeled oligonucleotide further comprises a quencher moiety.

The present invention also provides methods of detecting a St. Louis encephalitis virus. In some embodiments, the methods comprise amplifying a nucleic acid of St. Louis encephalitis virus with at least one oligonucleotide comprising a nucleotide sequence that hybridizes to SEQ ID NO:29 or a complement thereof, SEQ ID NO:30 or a complement thereof, SEQ ID NO:31 or a complement thereof, SEQ ID NO:32 or a complement thereof, SEQ ID NO:33 or a complement thereof, SEQ ID NO:34 or a complement thereof, SEQ ID NO:35 or a complement thereof, SEQ ID NO:36 or a complement thereof, SEQ ID NO:37 or a complement thereof, SEQ ID NO:38 or a complement thereof, SEQ ID NO:39 or a complement thereof, or SEQ ID NO:40 or a complement thereof, under conditions to allow for initiation of amplification of at least part of the nucleotide sequence from the oligonucleotide; and detecting the amplified nucleic acid, thereby detecting a St. Louis encephalitis virus.

In some embodiments, the oligonucleotide comprises a sequence selected from the group consisting of SEQ ID NO:64, SEQ ID NO:65, SEQ ID NO:66, and SEQ ID NO:67. In some embodiments, the oligonucleotide is selected from the group consisting of SEQ ID NO:64, SEQ ID NO:65, SEQ ID NO:66, and SEQ ID NO:67. In some embodiments, the oligonucleotide hybridizes to SEQ ID NO:68 or a complement of SEQ ID NO:69. In some embodiments, the oligonucleotide has fewer than 100 nucleotides.

In some embodiments, the nucleic acid of St. Louis encephalitis virus is amplified with a primer selected from the group consisting of SEQ ID NO:64 and SEQ ID NO:65; and a primer selected from the group consisting of SEQ ID NO:66 and SEQ ID NO:67.

In some embodiments, the detecting step comprises hybridizing a detectably-labeled oligonucleotide that hybridizes to SEQ ID NO:16 to the amplified nucleic acid of the nucleic acid of St. Louis encephalitis virus; and detecting hybridization of the probe to the amplified nucleic acid.

In some embodiments, the detectably-labeled oligonucleotide comprises at least 20 consecutive nucleotides of SEQ ID NO.:17, or the complement thereof. In some embodiments, the detectably-labeled oligonucleotide comprises SEQ ID NO.:28, or the complement thereof. In some embodiments, the detectably-labeled oligonucleotide comprises a fluorescent moiety. In some embodiments, the detectably-labeled oligonucleotide further comprises a quencher moiety.

In some embodiments, the quantity of amplified nucleic acid is determined during the amplifying step, thereby quantifying the virus in the sample.

In some embodiments, the amplifying step is performed in an amplification reaction mixture comprising a template-dependent nucleic acid polymerase with 5'-3' exonuclease activity under conditions that allow the template-dependent nucleic acid polymerase to fragment the detectably-labeled oligonucleotide; and the method further comprises detecting fragmentation of the detectably-labeled nucleic acid oligonucleotide.

The present invention also provides kits for detecting St. Louis encephalitis virus. In some embodiments, the kits comprise a oligonucleotide comprising a nucleotide sequence that hybridizes to SEQ ID NO:29 or a complement thereof, SEQ ID NO:30 or a complement thereof, SEQ ID NO:31 or a complement thereof, SEQ ID NO:32 or a complement thereof, SEQ ID NO:33 or a complement thereof, SEQ ID NO:34 or a complement thereof, SEQ ID NO:35 or a complement thereof, SEQ ID NO:36 or a complement thereof, SEQ ID NO:37 or a complement thereof, SEQ ID NO:38 or a complement thereof, SEQ ID NO:39 or a complement thereof, or SEQ ID NO:40 or a complement thereof.

In some embodiments, the oligonucleotide hybridizes to SEQ ID NO:68 or the complement of SEQ ID NO:69. In some embodiments, the oligonucleotide comprises a sequence selected from the group consisting of SEQ ID NO:64, SEQ ID NO:65, SEQ ID NO:66, and SEQ ID NO:67. In some embodiments, the oligonucleotide is selected from the group consisting of SEQ ID NO:64, SEQ ID NO:65, SEQ ID NO:66, and SEQ ID NO:67.

In some embodiments, the kits comprise an oligonucleotide selected from the group consisting of SEQ ID NO:64 and SEQ ID NO:65; and an oligonucleotide selected from the group consisting of SEQ ID NO:66 and SEQ ID NO:67. In some embodiments, the oligonucleotide has fewer than 100 nucleotides. In some embodiments, the kits further comprise a detectably-labeled oligonucleotide that hybridizes to SEQ ID NO:16 or a complement thereof.

The present invention also provides oligonucleotides comprising a sequence selected from the group consisting of SEQ ID NO: 56, SEQ ID NO: 57, SEQ ID NO: 58, SEQ ID NO: 59, SEQ ID NO: 60, SEQ ID NO: 61, SEQ ID NO: 62, and SEQ ID NO:63. In some embodiments, the oligonucleotide is selected from the group consisting of SEQ ID NO: 56, SEQ ID NO: 57, SEQ ID NO: 58, SEQ ID NO: 59, SEQ ID NO: 60, SEQ ID NO: 61, SEQ ID NO: 62, and SEQ ID NO:63.

The present invention also provides reaction mixtures comprising an oligonucleotide comprising a sequence selected from the group consisting of SEQ ID NO: 56, SEQ ID NO: 57, SEQ ID NO: 58, SEQ ID NO: 59, SEQ ID NO: 60, SEQ ID NO: 61, SEQ ID NO: 62, and SEQ ID NO:63. In some embodiments, the oligonucleotide is selected from the group consisting of SEQ ID NO: 56, SEQ ID NO: 57, SEQ ID NO: 58, SEQ ID NO: 59, SEQ ID NO: 60, SEQ ID NO: 61, SEQ ID NO: 62, and SEQ ID NO:63.

In some embodiments, the reaction mixtures further comprise a detectably-labeled oligonucleotide that hybridizes to SEQ ID NO:25 or a complement thereof. In some embodiments, the reaction mixtures further comprise a detectably-labeled oligonucleotide comprising FGGTCTAGAIGGTTAGAGGAGACCCTCCAG (SEQ ID NO:75), wherein F is CY5 and I is FAM. In some embodiments, the reaction mixtures further comprise a detectably-labeled oligonucleotide that hybridizes to SEQ ID NO:16 or a complement thereof.

In some embodiments, the reaction mixture comprises a DNA polymerase. In some embodiments, the reaction mixtures comprise at least one upstream primer and at least one downstream primer.

The present invention also provides methods of detecting a yellow fever virus. In some embodiments, the methods comprise amplifying a nucleic acid of yellow fever virus with at least one oligonucleotide comprising a sequence selected from the group consisting of SEQ ID NO: 56, SEQ ID NO: 57, SEQ ID NO: 58, SEQ ID NO: 59, SEQ ID NO: 60, SEQ ID NO: 61, SEQ ID NO: 62, and SEQ ID NO:63 under conditions to allow for initiation of amplification of at least part of the nucleotide sequence from the oligonucleotide; and detecting the amplified nucleic acid, thereby detecting a yellow fever virus.

In some embodiments, the oligonucleotide is selected from the group consisting of SEQ ID NO: 56, SEQ ID NO: 57, SEQ ID NO: 58, SEQ ID NO: 59, SEQ ID NO: 60, SEQ ID NO: 61, SEQ ID NO: 62, and SEQ ID NO:63. In some embodiments, the detecting step comprises hybridizing a detectably-labeled oligonucleotide that hybridizes to SEQ ID NO:25, or a complement thereof, to the amplified nucleic acid of the nucleic acid of yellow fever virus; and detecting hybridization of the detectably-labeled oligonucleotide to the amplified nucleic acid.

In some embodiments, the detectably-labeled oligonucleotide comprises FGGTCTAGAIGGTTAGAGGAGACCCTCCAG (SEQ ID NO:75), wherein F is CY5 and I is FAM. In some embodiments, the detecting step comprises hybridizing a detectably-labeled oligonucleotide that hybridizes to SEQ ID NO:16, or a complement thereof, to the amplified nucleic acid of the nucleic acid of yellow fever virus; and detecting hybridization of the detectably-labeled oligonucleotide to the amplified nucleic acid.

In some embodiments, the detectably-labeled oligonucleotide comprises at least 20 consecutive nucleotides of SEQ ID NO.:17, or the complement thereof. In some embodiments, the detectably-labeled oligonucleotide comprises SEQ ID NO.: 28, or the complement thereof. In some embodiments, the detectably-labeled oligonucleotide comprises a fluorescent moiety. In some embodiments, the detectably-labeled oligonucleotide further comprises a quencher moiety.

In some embodiments, the oligonucleotide has fewer than 100 nucleotides. In some embodiments, the quantity of amplified nucleic acid is determined during the amplifying step, thereby quantifying the virus in the sample.

In some embodiments, the amplifying step is performed in an amplification reaction mixture comprising a template-dependent nucleic acid polymerase with 5'-3' exonuclease activity under conditions that allow the template dependent nucleic acid polymerase to fragment the detectably-labeled oligonucleotide; and the method further comprises detecting fragmentation of the detectably-labeled oligonucleotide.

The present invention also provides kits for detecting yellow fever virus. The kit comprises an oligonucleotide comprising a sequence selected from the group consisting of SEQ ID NO: 56, SEQ ID NO: 57, SEQ ID NO: 58, SEQ ID NO: 59, SEQ ID NO: 60, SEQ ID NO: 61, SEQ ID NO: 62, and SEQ ID NO:63. In some embodiments, the oligonucleotide is selected from the group consisting of SEQ ID NO: 56, SEQ ID NO: 57, SEQ ID NO: 58, SEQ ID NO: 59, SEQ ID NO: 60, SEQ ID NO: 61, SEQ ID NO: 62, and SEQ ID NO:63.

In some embodiments, the kits further comprise a detectably-labeled oligonucleotide that hybridizes to SEQ ID NO:16 or a complement thereof. In some embodiments, the kits further comprise a detectably-labeled oligonucleotide that hybridizes to SEQ ID NO:25 or a complement thereof. In some embodiments, the kits further comprise a detectably-labeled oligonucleotide comprising FGGTCTAGAIGGTTAGAGGAGACCCTCCAG (SEQ ID NO:75), wherein F is CY5 and I is FAM.

In some embodiments, the reaction mixture comprises a DNA polymerase. In some embodiments, the reaction mixtures comprise at least one upstream primer and at least one downstream primer.

The present invention also provides oligonucleotides comprising a sequence selected from the group consisting of SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO:48, SEQ ID NO:49, SEQ ID NO:50, SEQ ID NO:51, SEQ ID NO:52, SEQ ID NO:53, SEQ ID NO:54, and SEQ ID NO:55. In some embodiments, the oligonucleotide is selected from the group consisting of SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO:48, SEQ ID NO:49, SEQ ID NO:50, SEQ ID NO:51, SEQ ID NO:52, SEQ ID NO:53, SEQ ID NO:54, and SEQ ID NO:55.

The present invention also provides reaction mixtures comprising an oligonucleotide comprising a sequence selected from the group consisting of SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO:48, SEQ ID NO:49, SEQ ID NO:50, SEQ ID NO:51, SEQ ID NO:52, SEQ ID NO:53, SEQ ID NO:54, and SEQ ID NO:55. In some embodiments, the oligonucleotide is selected from the group consisting of SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO:48, SEQ ID NO:49, SEQ ID NO:50, SEQ ID NO:51, SEQ ID NO:52, SEQ ID NO:53, SEQ ID NO:54, and SEQ ID NO:55.

In some embodiments, the reaction mixtures further comprise a detectably-labeled oligonucleotide that hybridizes to SEQ ID NO:16 or a complement thereof. In some embodiments, the reaction mixture comprises a DNA polymerase. In some embodiments, the reaction mixtures comprise at least one upstream primer and at least one downstream primer.

The present invention also provides methods of detecting a Dengue fever virus. In some embodiments, the methods comprise amplifying a nucleic acid of Dengue fever virus with at least one oligonucleotide comprising a sequence selected from the group consisting of SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO:48, SEQ ID NO:49, SEQ ID NO:50, SEQ ID NO:51, SEQ ID NO:52, SEQ ID NO:53, SEQ ID NO:54, and SEQ ID NO:55 under conditions to allow for initiation of amplification of at least part of the nucleotide sequence from the oligonucleotide; and detecting the amplified nucleic acid, thereby detecting a Dengue fever virus.

In some embodiments, the method further comprises hybridizing a detectably-labeled oligonucleotide that hybridizes to SEQ ID NO: 16 to the amplified Dengue fever virus nucleic acid; and detecting hybridization of the oligonucleotide to the amplified nucleic acid. In some embodiments, the oligonucleotide is selected from the group consisting of SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO:48, SEQ ID NO:49, SEQ ID NO:50, SEQ ID NO:51, SEQ ID NO:52, SEQ ID NO:53, SEQ ID NO:54, and SEQ ID NO:55.

In some embodiments, the nucleic acid is amplified with at least one upstream primer and at least one downstream primer. In some embodiments, the detectably-labeled oligonucleotide comprises at least 20 consecutive nucleotides of SEQ ID NO.: 17, or the complement thereof. In some embodiments, the detectably-labeled oligonucleotide comprises SEQ ID NO.:28, or the complement thereof. In some embodiments, the detectably-labeled oligonucleotide comprises a fluorescent moiety. In some embodiments, the detectably-labeled oligonucleotide further comprises a quencher moiety.

In some embodiments, the oligonucleotide has fewer than 100 nucleotides. In some embodiments, the quantity of amplified nucleic acid is determined during the amplifying step, thereby quantifying the virus in the sample. In some embodiments, the amplifying step is performed in an amplification reaction mixture comprising a template-dependent nucleic acid polymerase with 5'-3' exonuclease activity under conditions that allow the template dependent nucleic acid polymerase to fragment the detectably-labeled oligonucleotide; and the method further comprises detecting fragmentation of the detectably-labeled nucleic acid oligonucleotide.

The present invention also provides kits for detecting Dengue virus. In some embodiments, the kit comprises an oligonucleotide comprising a sequence selected from the group consisting of SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO:48, SEQ ID NO:49, SEQ ID NO:50, SEQ ID NO:51, SEQ ID NO:52, SEQ ID NO:53, SEQ ID NO:54, and SEQ ID NO:55. In some embodiments, the oligonucleotide is selected from the group consisting of SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO:48, SEQ ID NO:49, SEQ ID NO:50, SEQ ID NO:51, SEQ ID NO:52, SEQ ID NO:53, SEQ ID NO:54, and SEQ ID NO:55.

In some embodiments, the kits further comprise a detectably-labeled oligonucleotide that hybridizes to SEQ ID NO:16 or a complement thereof. In some embodiments, the reaction mixture comprises a DNA polymerase.

In some embodiments, quantification step is performed using either an internal or an external control nucleic acid. See U.S. Pat. Nos. 5,476, 774 and 5,219,727, which are incorporated by reference in their entirety.

BRIEF DESCRIPTION OF THE DRAWINGS

FIG. 1 presents a region of conserved sequence, identified as SEQ ID NO.: 1, in the 3' untranslated region of the genomes of the flaviviruses that can be detected using the compositions and methods of the present invention and that can be bound by a primer of the invention. SEQ ID NO.: 2 represents the complement of SEQ ID NO.: 1. The conserved region in the 3' untranslated region of the genomes of the flaviviruses=SEQ ID NOS:71 and 81-241, respectively.

FIG. 2 presents a region of conserved sequence, identified as SEQ ID NO.: 9, in the 3' untranslated region of the genomes of the flaviviruses that can be detected using the compositions and methods of the present invention and that can be bound by a primer of the invention. SEQ ID NO.: 10 represents the complement of SEQ ID NO.: 9. The conserved region in the 3' untranslated region of the genomes of the flaviviruses=SEQ ID NOS:72 and 242-315, respectively.

FIG. 3 presents a region of conserved sequence, identified as SEQ ID NO.: 16, in the 3' untranslated region of the genomes of the flaviviruses that can be detected using the compositions and methods of the present invention and that can be bound by a probe of the invention. SEQ ID NO.: 17 represents the complement of SEQ ID NO.: 16. The conserved region in the 3' untranslated region of the genomes of the flaviviruses=SEQ ID NO:73 and 316-605, respectively.

FIG. 4 presents an alignment of the nucleic acid sequences of the oligonucleotides of the invention with nucleic acid sequences of Japanese encephalitis virus serogroup members (SEQ ID NOS:7, 606-670, 7, 671-736, 15, 737-788, 16 and 789-839, respectively).

FIG. 5 presents an alignment of the nucleic acid sequences of the oligonucleotides of the invention with nucleic acid sequences of detectable flaviviruses that are not members of the Japanese encephalitis virus serogroup (SEQ ID NOS:16, 840-909, 16 and 910-919, respectively).

FIG. 6 presents a plot of normalized fluorescence versus number of amplification cycles showing detection of serially diluted extracted WNV RNA using the oligonucleotides of the invention.

FIG. 7 presents the sequence of the 3' untranslated region of the genomes of a number of SLEV isolates that can be detected using the compositions and methods of the present invention and that can be bound by a primer of the invention. Sequences for the following isolates are depicted: BFS1750 (SEQ ID NO:29), 1750-Std (SEQ ID NO:30), TD6-4G (SEQ ID NO:31), CoaV750 (SEQ ID NO:32), L695121.05 (SEQ ID NO:33), TNM771K (SEQ ID NO:34), MSI-7 (SEQ ID NO:35), Kern217 (SEQ ID NO:36), CoaV608 (SEQ ID NO:37), TBH-28 (SEQ ID NO:38), VR1265 (SEQ ID NO:39), and CoaV353 (SEQ ID NO:40).

DETAILED DESCRIPTION OF THE INVENTION

1. Abbreviations

The abbreviations used throughout the specification to refer to nucleic acids comprising specific nucleotide sequences are the conventional one-letter abbreviations. Thus, when included in a nucleic acid, the naturally occurring encoding nucleotides are abbreviated as follows: adenine (A), guanine (G), cytosine (C), thymine (T) and uracil (U). Also, unless otherwise specified, nucleic acid sequences that are represented as a series of one-letter abbreviations are presented in the 5'→3' direction.

2. Definitions

An "amplification reaction" refers to any reaction (e.g., chemical, enzymatic, or other type of reaction) that results in increased copies of a template nucleic acid sequence or increased signal indicating the presence of the template. Amplification reactions include, e.g., the polymerase chain reaction (PCR) and ligase chain reaction (LCR) (see U.S. Pat. Nos. 4,683,195 and 4,683,202*; PCR Protocols: A Guide to Methods and Applications* (Innis et al., eds, 1990)), strand displacement amplification (SDA) (Walker, et al. *Nucleic Acids Res*. 20(7):1691-6 (1992); Walker *PCR Methods Appl* 3(1):1-6 (1993)), transcription-mediated amplification (Phyffer, et al., *J. Clin. Microbiol*. 34:834-841 (1996); Vuorinen, et al., *J. Clin. Microbiol*. 33:1856-1859 (1995)), nucleic acid sequence-based amplification (NASBA) (Compton, *Nature* 350(6313):91-2 (1991), rolling circle amplification (RCA) (Lisby, *Mol. Biotechnol*. 12(1):75-99 (1999)); Hatch et al., *Genet. Anal*. 15(2):35-40 (1999)) branched DNA signal amplification (bDNA) (Iqbal et al., *Mol. Cell Probes* 13(4): 315-320 (1999)) and Q-Beta Replicase (Lizardi et al., *Bio/Technology* 6:1197 (1988)).

As used herein, a "sample" refers to any substance containing or presumed to contain nucleic acid. The sample can be of natural or synthetic origin and can be obtained by any means known to those of skill in the art. The sample can be a sample of tissue or fluid isolated from an individual or individuals, including, but not limited to, for example, skin, plasma, serum, whole blood, spinal fluid, semen, seminal fluid, lymph fluid, synovial fluid, urine, tears, blood cells, organs, tumors, bronchio-alveolar lavage, and also to samples of in vitro cell culture constituents (including but not limited to conditioned medium resulting from the growth of cells in cell culture medium, recombinant cells and cell components). A nucleic acid can be obtained from a biological sample by any procedure known in the art.

As used herein, the terms "nucleic acid," ""polynucleotide" and "oligonucleotide" refer to primers, probes, oligomer fragments to be detected, oligomer controls and unlabeled blocking oligomers and is generic to linear polymers of polydeoxyribonucleotides (containing 2-deoxy-D-ribose), polyribonucleotides (containing D-ribose), and any other N-glycoside of a purine or pyrimidine base, or modified purine or pyrimidine bases.

A nucleic acid, polynucleotide or oligonucleotide can comprise phosphodiester linkages or modified linkages including, but not limited to phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages.

A nucleic acid, polynucleotide or oligonucleotide can comprise the five biologically occurring bases (adenine, guanine, thymine, cytosine and uracil) and/or bases other than the five biologically occurring bases. These bases may serve a number of purposes, e.g., to stabilize or destabilize hybridization; to promote or inhibit probe degradation; or as attachment points for detectable moieties or quencher moieties. For example, a polynucleotide of the invention can contain one or more modified, non-standard, or derivatized base moieties, including, but not limited to, $N^6$-methyl-adenine, $N^6$-tert-butyl-benzyl-adenine, imidazole, substituted imidazoles, 5-fluorouracil, 5-bromouracil, 5-chlorouracil, 5-iodouracil, hypoxanthine, xanthine, 4-acetylcytosine, 5-(carboxyhydroxymethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acidmethylester, 3-(3-amino-3-N-2-carboxypropyl) uracil, (acp3)w, 2,6-diaminopurine, and 5-propynyl pyrimidine. Other examples of modified, non-standard, or derivatized base moieties may be found in U.S. Pat. Nos. 6,001,611, 5,955,589, 5,844,106, 5,789,562, 5,750,343, 5,728,525, and 5,679,785, each of which is incorporated herein by reference in its entirety.

Furthermore, a nucleic acid, polynucleotide or oligonucleotide can comprise one or more modified sugar moieties including, but not limited to, arabinose, 2-fluoroarabinose, xylulose, and a hexose.

It is not intended that the present invention be limited by the source of a nucleic acid, polynucleotide or oligonucleotide. A nucleic acid, polynucleotide or oligonucleotide can be from a human or non-human mammal, or any other organism, or derived from any recombinant source, synthesized in vitro or by chemical synthesis. A nucleic acid, nucleotide, polynucleotide or oligonucleotide may be DNA, RNA, cDNA, DNA-RNA, locked nucleic acid (LNA), peptide nucleic acid (PNA), a hybrid or any mixture of the same, and may exist in a double-stranded, single-stranded or partially double-stranded form. A nucleic acid may also be a derivative nucleic acid as described in U.S. Pat. No. 5,696,248, which is hereby incorporated by reference in its entirety. The nucleic acids of the invention include both nucleic acids and fragments thereof, in purified or unpurified forms, including genes, chromosomes, plasmids, the genomes of biological material such as microorganisms, e.g., bacteria, yeasts, viruses, viroids, molds, fungi, plants, animals, humans, and the like.

There is no intended distinction in length between the terms nucleic acid, polynucleotide and oligonucleotide, and these terms will be used interchangeably. These terms include double- and single-stranded DNA, as well as double- and single-stranded RNA. Oligonucleotides of the invention may be used as primers and/or probes. Thus oligonucleotides referred to herein as "primers" may act as probes and oligonucleotides referred to as "probes" may act as primer in some embodiments.

The term "residue" as used herein refers to a nucleotide or base within a nucleic acid as defined above. A residue can be any nucleotide known to one of skill in the art without limitation, including all of the biologically occurring nucleotides and non-biologically occurring nucleotides described above.

The term "primer" refers to an oligonucleotide which is capable of acting as a point of initiation of polynucleotide synthesis along a template nucleic acid strand when placed under conditions that permit synthesis of a primer extension product that is complementary to the template strand. The primer can be obtained from a recombinant source, as in a purified restriction fragment, or produced synthetically. Primer extension conditions typically include the presence of four different deoxyribonucleoside triphosphates and an agent with polymerization activity such as DNA polymerase or reverse transcriptase, in a suitable buffer (a "buffer" can include substituents which are cofactors, or which affect pH, ionic strength, etc.), and at a suitable temperature. The primer is preferably single-stranded for maximum efficiency in amplification. Primers of the invention may be, e.g., between 5 to 500 nucleotides, and in some embodiments will have at least 10, 20, 30, 25, 30, 40, 50, 75, or 100 nucleotides and/or have fewer than 500, 300, 200, 100, 90, 80, 70, 60, 50, 40, 30, 25, or 20 nucleotides.

The term "hybridize" refers to binding of a single-stranded nucleic acid or a locally single-stranded region of a double-stranded nucleic acid to another single-stranded nucleic acid or a locally single-stranded region of a double-stranded nucleic acid having a complementary sequence. As one of skill in the art is aware, it is not necessary for two nucleic acid strands to be entirely complementary to hybridize to each other. Depending on the hybridization conditions, a nucleic acid can hybridize to its complement even if there are few, some, or many mismatches, deletions, or additions in one or both strands. In certain embodiments, the primers and probes of the invention can hybridize to an at least partially complementary nucleic acid selectively, as defined below. In certain embodiments, the primers and probes of the invention can hybridize to an at least partially complementary sequence under stringent conditions, as defined below.

The terms "stringent" or "stringent conditions", as used herein, denote hybridization conditions of low ionic strength and high temperature, as is well known in the art; see for example Maniatis et al., 1989, Molecular Cloning: A Laboratory Manual, 2d Edition; Current Protocols in Molecular Biology, 1988, ed. Ausubel et al., J. Wiley & Sons publ., New York, and Tijssen, 1993, Techniques in Biochemistry and Molecular Biology-Hybridization with Nucleic Acid Probes, "Overview of principles of hybridization and the strategy of nucleic acid assays," each of which is hereby incorporated by reference. Generally, stringent conditions are selected to be about 5-30° C. lower than the thermal melting point (Tm) for the specified sequence at a defined ionic strength and pH. Alternatively, stringent conditions are selected to be about 5-15° C. lower than the thermal melting point (Tm) for the specified sequence at a defined ionic strength and pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). For example, stringent hybridization conditions will be those in which the salt concentration is less than about 1.0 M sodium (or other salts) ion, typically about 0.01 to about 1 M sodium ion concentration at about pH 7.0 to about pH 8.3 and the temperature is at least about 25° C. for short probes (e.g., 10 to 50 nucleotides) and at least about 55° C. for long probes (e.g., greater than 50 nucleotides). Stringent conditions may also be modified with the addition of hybridization destabilizing agents such as formamide.

The terms "selective" or "selective conditions", as used herein, denote hybridization conditions for the primers and/or probes of the invention that permit amplification, detection and/or quantification of a detectable flavivirus nucleic acid in a sample that may contain additional nucleic acids not derived from the detectable flavivirus, or derived from unrelated regions of the flaviviral genome. Detectable flaviviruses are described below.

The "complement" of a nucleic acid sequence, as used herein, refers to an oligonucleotide which, when aligned with the nucleic acid sequence such that the 5' end of one sequence is paired with the 3' end of the other, is in anti-parallel association. The complement of a nucleic acid sequence need not exactly match every nucleotide of the sequence; stable duplexes may contain mismatched base pairs or unmatched bases. Those skilled in the art of nucleic acid technology can determine duplex stability by empirically considering a number of variables including, for example, the length of the oligonucleotide, base composition and sequence of the oligonucleotide, ionic strength, and incidence of mismatched base pairs.

Stability of a nucleic acid duplex is measured by the melting temperature, or "$T_m$". The $T_m$ of a particular nucleic acid duplex under specified conditions is the temperature at which half of the potential base pairs are disassociated.

As used herein, the term "probe" refers to an oligonucleotide which can form a duplex structure with a region of a nucleic acid, due to complementarity of at least one sequence in the probe with a sequence in the region. The probe, preferably, does not contain a sequence complementary to sequence(s) of a primer. As discussed below, the probe can be labeled or unlabeled. The 3' terminus of the probe can be "blocked" to prohibit incorporation of the probe into a primer extension product. "Blocking" can be achieved by using non-complementary bases or by adding a chemical moiety such as biotin or a phosphate group to the 3' hydroxyl of the last nucleotide, which may, depending upon the selected moiety, serve a dual purpose by also acting as a label for subsequent detection or capture of the nucleic acid attached to the label. Blocking can also be achieved by removing the 3' hydroxyl or by using a nucleotide that lacks a 3' hydroxyl such as a dideoxynucleotide.

The term "detectable moiety" as used herein refers to any atom or molecule which can be used to provide a detectable (optionally quantifiable) signal, and which can be attached to a nucleic acid or protein. Detectable moieties may provide signals detectable by fluorescence, radioactivity, colorimetry, gravimetry, X-ray diffraction or absorption, magnetism, enzymatic activity, and the like. Convenient detectable moieties for the present invention include those that facilitate detection of the size of an oligonucleotide fragment.

The term "fluorescent moiety" as used herein refers to a chemical moiety that can emit light under conditions appropriate for the particular moiety. Typically, a particular fluorescent moiety can emit light of a particular wavelength following absorbance of light of shorter wavelength. The wavelength of the light emitted by a particular fluorescent moiety is characteristic of that moiety. Thus, a particular fluorescent moiety can be detected by detecting light of an appropriate wavelength following excitation of the fluorescent moiety with light of shorter wavelength. Examples of fluorescent moieties that can be used in the methods and compositions of the present invention include, but are not limited to, fluorescein-family dyes, polyhalofluorescein-family dyes, hexachlorofluorescein-family dyes, coumarin-family dyes, rhodamine-family dyes, cyanine-family dyes, oxazine-family dyes, thiazine-family dyes, squaraine-family dyes, chelated lanthanide-family dyes, and BODIPY®-family dyes.

The term "quencher moiety" as used herein refers to a chemical moiety that can absorb energy emitted by a fluorescent moiety when the quencher moiety is sufficiently close to the fluorescent moiety, for example, when both the quencher and fluorescent moiety are linked to a common polynucleotide. This phenomenon is generally known in the art as fluorescent resonance energy transfer ("FRET"). A quencher moiety can re-emit the energy absorbed from a fluorescent moiety in a signal characteristic for that quencher moiety, and thus a quencher can also be a "fluorescent moiety." Alternatively, a quencher moiety may dissipate the energy absorbed from a fluorescent moiety as heat.

As defined herein, "5' to 3' nuclease activity" or "5' nuclease activity" refers to that activity of an enzyme whereby nucleotides are removed from the 5' end of an oligonucleotide in a sequential manner. The 5' nuclease activity can be a 5' to 3' exonuclease activity or a 5' to 3' endonuclease activity. For example, many template-specific nucleic acid polymerases exhibit a 5' to 3' exonuclease activity that is traditionally associated with some DNA polymerases, (i.e., *E. coli* DNA polymerase I has this activity whereas the Klenow fragment of *E. coli* DNA polymerase I does not). The 5' to 3' exonuclease activity can also cleave a substrate nucleic acid more than one phosphodiester bond (nucleotide) from the 5' end of the substrate. Although not intending to be bound by any particular theory of operation, it is believed that this aspect of 5' to 3' exonuclease activity associated with DNA polymerases, which leads to release of cleaved oligonucleotide fragments from probes, can depend upon the particular nucleotide composition of the probe. For instance, the number of matches or mismatches between nucleotides of the oligonucleotide and template nucleic acid, particularly at the 5' end of the oligonucleotide, can influence this activity, as described, for example, by Holland et al., 1991, Proc. Natl. Acad. Sci. USA 88:7276-80, which is incorporated herein by reference in its entirety.

The term "control 5' nuclease reaction" as used herein refers to a 5' nuclease reaction performed as described below on a known amount, e.g., copy number, of a nucleic acid of a detectable flavivirus. The amount of fluorescence emitted by such a reaction can be compared to a reaction performed on a sample with an unknown quantity of a nucleic acid of a Japanese encephalitis virus serogroup to assess the amount of such nucleic acid present in the sample.

The term "adjacent" as used herein refers to the positioning of the primer with respect to the probe on the same or the complementary strand of the template nucleic acid. The primer and probe may be separated by more than about 150 nucleotides, more than about 125 nucleotides, more than about 100 nucleotides, more than about 80 nucleotides, more than about 60 nucleotides, more than about 50 nucleotides, more than about 40 nucleotides, more than about 30 nucleotides, more than about 20 nucleotides, by about 1 to about 20 nucleotides, by about 1 to about 10 nucleotides, or may directly abut one another. If it is desired to detect a flavivirus nucleic acid with a polymerization-independent process, the probe is preferably separated from the probe by about 1 to about 10 nucleotides. In the polymerization-dependent process, for example, a PCR amplification and detection methods as taught herein, the probe may hybridize to the detectable nucleic acid anywhere within the sequence to be amplified that is downstream of a primer, thus allowing primer extension to position the polymerase so that the probe is fragmented.

The term "thermostable nucleic acid polymerase" refers to an enzyme which is relatively stable to heat when compared, for example, to nucleotide polymerases from *E. coli* and which catalyzes the polymerization of nucleoside triphosphates. Generally, such enzymes are obtained from organisms considered by those in the art to be thermophilic organisms. Generally, the enzyme will initiate synthesis at the 3' end of a primer annealed to the primer binding sequence, and will continue synthesis of a new strand toward the 5' end of the template. If the polymerase possesses a 5' to 3' nuclease activity, it can hydrolyze intervening probes annealed to the template to release both labeled and unlabeled probe fragments, until polymerization terminates or all probe fragments dissociate from the nucleic acid to be detected. A representative thermostable enzyme isolated from *Thermus aquaticus* (Taq) is described in U.S. Pat. No. 4,889,818 and a method for using it in conventional PCR is described in Saiki et al., 1988, *Science* 239:487-91. Another representative thermostable enzyme includes *Thermus* species Z05 DNA polymerase. See, e.g., U.S. Pat. No. 5,674,738.

Taq DNA polymerase has a DNA synthesis-dependent, strand replacement 5'-3' exonuclease activity (see Gelfand, "Taq DNA Polymerase" in PCR Technology Principles and Applications for DNA Amplification, Erlich, Ed., Stockton Press, N.Y. (1989), Chapter 2). Thus, Taq DNA polymerase does not degrade the probe when it is unbound to template DNA.

The term "5' nuclease reaction" of a nucleic acid primer or probe refers to the degradation of a probe hybridized to the nucleic acid when the primer is extended by a nucleic acid polymerase having 5' to 3' nuclease activity, as defined above and described in detail below. Such reactions are based on those described in U.S. Pat. Nos. 6,214,979, 5,804,375, 5,487,972 and 5,210,015, each of which is hereby incorporated by reference in its entirety.

To determine "percent complementarity" or "percent identity" of two nucleic acid sequences, the sequences are aligned for optimal comparison purposes (e.g., gaps can be introduced in the sequence of a first nucleic acid sequence for optimal alignment with a second nucleic acid sequence). The nucleotides at corresponding nucleotide positions are then compared. When a position in the first sequence is occupied by a complementary nucleotide as the corresponding position in the second sequence, then the molecules are complementary at that position. Likewise, when a position in the first sequence is occupied by the same nucleotide as the corresponding position in the second sequence, then the molecules are identical at that position. The percent complementarity (or percent identity) between the two sequences is a finction of the number of complementary positions (or identical positions) shared by the sequences divided by the total number of positions compared (i.e., % complementarity=number of complementary overlapping positions/total number of positions of the shorter nucleotide×100%; and % identity=number of identical overlapping positions/total number of positions of the shorter nucleotide×100%).

The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST program of Altschul et al., 1990, J. Mol. Biol. 215:403.

The practice of the present invention will employ, unless otherwise indicated, conventional techniques of molecular biology, microbiology and recombinant DNA techniques, which are within the skill of the art. Such techniques are explained fully in the literature. See, e.g., Sambrook et al., 2001, Molecular Cloning: A Laboratory Manual, Third Edition, Cold Spring Harbor Laboratory Press, Cold Spring Harbor, N.Y.; Oligonucleotide Synthesis (M. J. Gait, ed., 1984); Nucleic Acid Hybridization (B. D. Hames & S. J. Higgins, eds., 1984); A Practical Guide to Molecular Cloning (B. Perbal, 1984); and a series, Methods in Enzymology (Academic Press, Inc.).

3. Nucleic Acid Primers and Probes for Detecting a Nucleic Acid of a Member of the Japanese Encephalitis Serogroup and Certain Other Flaviviruses The present invention provides oligonucleotides useful as primers and probes to detect the presence of a nucleic acid of a member of the Japanese encephalitis virus serogroup and certain other members of the genus Flavivirus, and methods of their use. These primers and probes are described in detail below. It is noted that while the primers discussed herein may be designated as particularly useful for amplifying a particular virus type (e.g., West Nile virus, SLEV, Dengue virus, yellow fever virus, etc.), the primers an be useful for amplifying other viruses as well.

The oligonucleotides useful in the methods of the invention may be designed to comprise nucleotide sequences, or complements thereof, that are conserved between different strains of Flaviviruses or that are conserved between two or more members of the Japanese encephalitis virus serogroup or other members of the genus Flavivirus. Oligonucleotides that comprise sequences conserved between different strains or members of a serogroup or genus may be useful, for example, as primers or probes that may be employed to detect the different strains or members, thereby reducing the number of primers or probes necessary to detect the different strains or members. Conserved sequences may include, for example, atleast 5, 6, 7, 8, 9, 10, 11, 12, 13, 14, 15, 16, 17, 18, 19, 20, 21, 22, 23, 24, 25, 30, 40, 50, or more contiguous nucleotides that are completely (i.e., 100%) or substantially identical between the two or more strains or two or more members of the Japanese encephalitis virus serogroup or other members of the genus Flavivirus. Substantially identical sequences include those that are, e.g., 80%, 85%, 90%, 91%, 92%, 93%, 94%, 95%, 96%, 97%, 98%, or 99% identical between the two or more strains across the above-listed contiguous nucleotides.

3.1. Nucleic Acid Primers

Primers Based on SEQ ID NO:1

In one aspect, the invention provides nucleic acid primers that can be used in methods of detecting members of the Japanese encephalitis virus serogroup. In certain embodiments, a first nucleic acid primer that can be used to detect a member of the Japanese encephalitis virus serogroup comprises a nucleic acid that hybridizes to a nucleic acid of SEQ ID NO.: 1 or a complement thereof. SEQ ID NO.: 1, as presented in FIG. 1, represents a region of conserved sequence in the 3' untranslated region of the genomes of the flaviviruses that can be detected using the compositions and methods of the present invention. SEQ ID NO.: 2 represents the complement to SEQ ID NO.: 1.

In such embodiments of the invention, the first nucleic acid primer has a nucleotide composition, i.e., chemical structure, that allows it to hybridize under the defined conditions to a nucleic acid of SEQ ID NO.: 1. In some cases, each nucleotide of a primer that hybridizes to a nucleic acid will form basepair complements with a nucleotide of the nucleic acid. For example, a primer containing a standard nucleotide that hybridizes to a C residue in the nucleic acid of SEQ ID NO.: 1 should have a G residue in the corresponding position. Thus, hybridization to the nucleic acid of SEQ ID NO.: 1 defines the nucleotide sequence and therefore the exact chemical structure of the primer. In addition, the first nucleic acid primer can also comprise non-standard nucleotides according to the definitions of oligonucleotide and primers recited above. Certain of such non-standard nucleotides can also bind to other standard or non-standard nucleotides to form a base-pair. For example, the nonstandard nucleotide inosine can pair with uracil, cytosine, and adenine. Given the known correlation between hybridization and chemical structure, one of skill in the art can easily recognize the standard features of the primers of the invention. Exemplary embodiments are described in detail below.

In certain embodiments, the first nucleic acid primer that hybridizes to a nucleic acid of SEQ ID NO.: 1 can be as short as about 6 nucleotides. In other embodiments, the first nucleic acid primer can be as long as about 80 nucleotides. In certain embodiments, the first nucleic acid primer comprises about 10, about 12, about 14, about 15, about 16, about 17, about 18, about 19, about 20, about 21, about 22, about 23, about 24, about 25, about 26, about 27, about 28, about 29, about 30, about 35, or about 40 nucleotides. In some embodiments, the first nucleic acid primer will comprise fewer than 100, 80, 70, 60, 50, 40, 30, 25, 21 or 20 nucleotides.

The length and composition of the primer can be chosen to give sufficient thermodynamic stability to ensure hybridization of the primer to the flaviviral nucleic acid under the appropriate reaction conditions, which depend on the detection method to be performed. For example, primers with modified, non-standard, or derivatized nucleotides may be longer or shorter than those with conventional nucleotides while having similar thermodynamic hybridization properties. Examples of such non-standard bases may be found in U.S. Pat. Nos. 6,320,005, 6,174,998, 6,001,611, and 5,990, 303, each of which is hereby incorporated by reference in its entirety. As another example, primers with G/C-rich sequences may anneal to target sequences at higher temperatures that a primer of similar length with A/T-rich sequences. Thus, in certain embodiments, the first nucleic acid primer comprises modified, non-standard, or derivatized bases, as defined above.

In certain embodiments, the first nucleic acid primer comprises at least about 16 consecutive nucleotides of SEQ ID NO.: 2. SEQ ID NO.: 2 is the complement to SEQ ID NO.: 1, as shown in FIG. 1. In other embodiments, the first nucleic acid primer comprises at least about 18 consecutive nucleotides of SEQ ID NO.: 2. In still other embodiments, the first nucleic acid primer comprises at least about 20 consecutive nucleotides of SEQ ID NO.: 2. In yet other embodiments, the first nucleic acid primer comprises at least about 22 consecutive nucleotides of SEQ ID NO.: 2. In still other embodiments, the first nucleic acid primer comprises at least about 24 consecutive nucleotides of SEQ ID NO.: 2.

In certain embodiments, the invention provides nucleic acid primers that can be used to detect a member of the Japanese encephalitis virus serogroup. These primers can be structurally defined by reference to their nucleic acid sequences, as presented in Table 1.

TABLE 1

| | |
|---|---|
| SEQ ID NO.: 3<br>Japanese encephalitis virus serogroup Primer 1 | $GN^2AAN^5CCN^8N^9N^{10}CN^{12}N^{13}AN^{15}CN^{17}N^{18}N^{19}N^{20}TCGGN^{25}N^{26}$<br>Wherein $N^2$ is T or A; $N^5$ is G or C; $N^8$ is T or absent; N at position 9 is C or G; $N^{10}$ is T or C; $N^{12}$ is A or G; $N^{13}$ is G or A; $N^{15}$ is A or C; $N^{17}$ is C or T; $N^{18}$ is G or C; $N^{19}$ is T or C; $N^{20}$ is C or T; $N^{25}$ is A or G; and $N^{26}$ is A or T. |
| SEQ ID NO.: 4<br>West Nile virus Primer 1 | $GTAAGCCN^8CN^{10}CAGAACCGN^{19}N^{20}TCGGAA$<br>Wherein $N^8$ is absent or T; $N^{10}$ is T or C; $N^{19}$ is T or C; and $N^{20}$ is C or T. |
| SEQ ID NO.: 5<br>Japanese encephalitis virus Primer 1 | $GAAAN^5CCN^8CTCN^{12}N^{13}AAC\ N^{17}GTN^{20}TCGGAA$<br>Wherein $N^5$ is G or C; $N^8$ is absent; $N^{12}$ is A or G; $N^{13}$ is G or A; $N^{17}$ is C or T; and $N^{20}$ is C or T. |
| SEQ ID NO.: 6<br>Murray Valley encephalitis virus Primer 1 | $GAAAGCCTCCCAGAN^{15}CCGTN^{20}TCGGAA$<br>Wherein $N^{15}$ is A or C; and $N^{20}$ is C or T. |
| SEQ ID NO.: 7<br>Koutango virus Primer 1 | GTAAGCCCTCAGAACCGTCTCGGAA |
| SEQ ID NO.: 8<br>Example Primer 1 | GTAAGCCCTCAGAACCGTCTCGGAA |
| SEQ ID NO.: 11<br>Japanese encephalitis virus serogroup Primer 2 | $N^1CCN^4AN^6TN^8TN^{10}N^{11}N^{12}N^{13}CCAGGTN^{20}TCAA$<br>Wherein $N^1$ is T or C; $N^4$ is C or T; $N^6$ is G or C; $N^8$ is C or A; $N^{10}$ is A or T; $N^{11}$ is absent or T; $N^{12}$ is T or C; $N^{13}$ C or T; and $N^{20}$ is G or A. |
| SEQ ID NO.: 12<br>West Nile virus Primer 2 | $N^1CCTAGTCTATCCCAGGTN^{20}TCAA$<br>Wherein $N^1$ is T or C and $N^{20}$ is G or A. |
| SEQ ID NO.: 13<br>Japanese encephalitis virus Primer 2 | $CCCN^4AN^6TN^8TATN^{12}N^{13}CCAGGTGTCAA$<br>Wherein $N^4$ is C or T; $N^6$ is G or C; $N^8$ is C or A; $N^{12}$ is T or C; and $N^{13}$ is C or T. |
| SEQ ID NO.: 14<br>Murray Valley encephalitis virus Primer 2 | TCCTAGTCTTTTCCCAGGTGTCAA |
| SEQ ID NO.: 15<br>Example Primer 2 | TCCTAGTCTATCCCAGGTGTCAA |
| SEQ ID NO.: 74<br>Example Primer 2 | TCTCCTAGTCTATCCCAGGTGTCAA |

In certain embodiments, the first nucleic acid primer comprises any of SEQ ID NOS.: 3-8. In certain embodiments of the invention, in order to improve primer specificity, the primers can comprise one or more alkylated nucleotides at or near its 3' end. For instance, in certain embodiments, first nucleic acid primer comprises SEQ ID NO.: 8, wherein the residue at position 23 is $N^6$-methyl-deoxyadenosine. In certain embodiments, the first nucleic acid comprises SEQ ID NO.: 8, wherein the residue at position 24 is $N^6$-alkyl-deoxyadenosine. In a specific embodiment, the first nucleic acid comprises SEQ ID NO.: 8, wherein the residue at position 24 is $N^6$-tert-butyl-benzyl-deoxyadenosine. In certain embodiments, the first nucleic acid primer comprises SEQ ID NO.: 8, wherein the residue at position 23 is $N^6$-alkyl-deoxyadenosine and the residue at position 24 is $N^6$-alkyl-deoxyadenosine. In yet another specific embodiment, the first nucleic acid primer comprises SEQ ID NO.: 8, wherein the residue at position 23 is $N^6$-methyl-deoxyadenosine and the residue at position 24 is $N^6$-tert-butyl-benzyl-deoxyadenos U.S. Pat. No. 6,001,611, incorporated by reference above, describes $N^6$-alkyl-deoxyadenosine as well as the identity of the alkyl moieties that can be used with such non-standard nucleotides. For example, in certain embodiments, the alkyl moiety comprises $C_1$ to about $C_{10}$ branched or unbranched alkyl. In other embodiments, the alkyl moiety comprises $C_1$ to about $C_{20}$ branched or unbranched alkyl.

In another aspect, the invention provides a second nucleic acid primer for detecting a member of the Japanese encephalitis virus serogroup comprising a nucleic acid that hybridizes to a nucleic acid of SEQ ID NO.: 9 a complement thereof. SEQ ID NO.: 9, as presented in FIG. 2, represents a region of conserved sequence in the 3' untranslated region of the genomes of the flaviviruses that can be detected using the compositions and methods of the present invention. FIG. 2 also shows that SEQ ID NO.: 10 represents the complement to SEQ ID NO.: 9.

In such embodiments of the invention, the second nucleic acid primer has a nucleotide composition, i.e., chemical structure, that allows it to hybridize to a nucleic acid of SEQ ID NO.: 9. For example, a primer containing a standard nucleotide that hybridizes to a C residue in the nucleic acid of SEQ ID NO.: 9 should have a G residue in the corresponding position. Thus, hybridization to the nucleic acid of SEQ ID NO.: 9 defines the nucleotide sequence and therefore the exact chemical structure of the primer. In addition, the second nucleic acid primer can also comprise non-standard nucleotides according to the definitions of oligonucleotides and primers recited above. Certain of such non-standard nucleotides can also bind to other standard or non-standard nucleotides to form a base-pair. For example, the nonstandard nucleotide inosine can pair with uracil, cytosine, and adenine. Given the known correlation between hybridization and chemical structure, one of skill in the art can easily recognize the standard features of the primers of the invention. Exemplary embodiments are described in detail below.

In certain embodiments, the second nucleic acid primer that hybridizes to a nucleic acid of SEQ ID NO.: 9 can be as short as about 6 nucleotides. In other embodiments, the second nucleic acid primer can be as long as about 80 nucleotides. In certain embodiments, the second nucleic acid primer comprises about 10, about 12, about 14, about 15, about 16, about 17, about 18, about 19, about 20, about 21, about 22, about 23, about 24, about 25, about 26, about 27, about 28, about 29, about 30, about 35, or about 40 nucleotides.

The length and composition of the second primer can be chosen to give sufficient thermodynamic stability to ensure hybridization of the primer to the flaviviral nucleic acid under the appropriate reaction conditions, which depend on the detection method to be performed. For example, primers with modified, non-standard, or derivatized nucleotides may be longer or shorter than those with conventional nucleotides while having similar thermodynamic hybridization properties. Examples of such non-standard bases may be found in U.S. Pat. Nos. 6,320,005, 6,174,998, 6,001,611, and 5,990,303, each of which is hereby incorporated by reference in its entirety. As another example, primers with G/C-rich sequences may anneal to target sequences at higher temperatures that a primer of similar length with A/T-rich sequences. Thus, in certain embodiments, the second nucleic acid primer comprises modified, non-standard, or derivatized bases as defined above.

In certain embodiments, the second nucleic acid primer comprises at least 16 consecutive nucleotides of SEQ ID NO.: 10. SEQ ID NO.: 10 represents the complement of SEQ ID NO.: 9, as shown in FIG. 2. In other embodiments, the second nucleic acid primer comprises at least about 18 consecutive nucleotides of SEQ ID NO.: 10. In still other embodiments, the second nucleic acid primer comprises at least about 20 consecutive nucleotides of SEQ ID NO.: 10. In yet other embodiments, the second nucleic acid primer comprises at least about 22 consecutive nucleotides of SEQ ID NO.: 10. In still other embodiments, the second nucleic acid primer comprises at least about 24 consecutive nucleotides of SEQ ID NO.: 10.

In certain embodiments, the second nucleic acid primer comprises SEQ ID NO.: 11. In other embodiments, the second nucleic acid primer comprises SEQ ID NO.: 12. In yet other embodiments, the second nucleic acid primer comprises SEQ ID NO.: 13. In still other embodiments, the second nucleic acid primer comprises SEQ ID NO.: 14. In yet other embodiments, the second nucleic acid primer comprises SEQ ID NO.: 15 or SEQ ID NO:74. In certain embodiments, the second nucleic acid primer comprises non-standard or derivatized nucleotides. In other embodiments, the second nucleic acid primer can comprise one or more alkylated nucleotides at or near the 3' end. In certain embodiments, the second nucleic acid primer comprises SEQ ID NO.: 15 or SEQ ID NO:74, wherein the residue at position 23 of SEQ ID NO: 15 or position 25 of SEQ ID NO:74 is $N^6$-alkyl-deoxyadenosine. In certain embodiments, the alkyl moiety comprises $C_1$ to about $C_{10}$ branched or unbranched alkyl. In other embodiments, the alkyl moiety comprises $C_1$ to about $C_{20}$ branched or unbranched alkyl. In a specific embodiment, the second nucleic acid primer comprises SEQ ID NO.: 15 or SEQ ID NO:74, wherein the residue at position 23 of SEQ ID NO:15 or position 25 of SEQ ID NO:74 is $N^6$-tert-butyl-benzyl-deoxyadenosine.

The nucleic acid primers of the invention may additionally comprise nucleic acid sequences that are not complementary and/or do not hybridize to a member of the Japanese encephalitis virus serogroup. These additional sequences can be selected by one of skill in the art to, for example, assist in the detection of the member of the Japanese encephalitis virus serogroup. Methods of detecting a nucleic acid, including a nucleic acid of a member of the Japanese encephalitis virus serogroup are extensively described in Sections 4.2 and 4.3, below. These methods describe both the additional nucleic acid sequences that can be present in the nucleic acid primers of the invention as well as methods of using these additional sequences to detect a member of the Japanese encephalitis virus serogroup.

The nucleic acid primers may be prepared by any suitable method known to one of skill in the art without limitation. Methods for preparing oligonucleotides of defined sequence are well-known to the art, and include, for example, cloning and restriction of appropriate sequences and direct chemical synthesis. Chemical synthesis methods may include, for example, the phosphotriester method described by Narang et al., 1979, Methods in Enzymology 68:90, the phosphodiester method disclosed by Brown et al., 1979, Methods in Enzymology 68:109, the diethylphosphoramidate method disclosed in Beaucage et al., 1981, Tetrahedron Letters 22:1859, and the solid support method disclosed in U.S. Pat. No. 4,458,066. In addition, modifications to the above-described methods of synthesis may be used to desirably impact enzyme behavior with respect to the synthesized oligonucleotides. For example, incorporation of modified phosphodiester linkages (e.g., phosphorothioate, methylphosphonates, phosphoamidate, or boranophosphate) or linkages other than a phosphorous acid derivative into an oligonucleotide may be used to prevent cleavage at a selected site. In addition, the use of 2'-amino modified sugars tends to favor displacement over digestion of the oligonucleotide when hybridized to a nucleic acid that is also the template for synthesis of a new nucleic acid strand.

Dengue Virus Primers

Additional primers of the invention hybridize to the Dengue virus 3' UTR. Exemplary primers useful for amplifying and/or detecting Dengue viruses nucleic acids include those depicted in Table 2.

TABLE 2

| Sequence | Comments | SEQ ID NO: |
|---|---|---|
| GAGCCCCGTCCAAGGACGTAAA AAGAA | Dengue virus consensus upstream primer. | 41 |
| GAGCCCCGTCCAAGGACGTAAA AAGAJ | Dengue virus consensus upstream primer. | 42 |
| GAGCCCCGTCCAAGGACGTAAA AAGEJ | Dengue virus consensus upstream primer. | 43 |
| GAGCCCCGTCCAAGGACGTAAA ATGAA | Dengue virus type I upstream primer. | 44 |
| GAGCCCCGTCCAAGGACGTAAA ATGAJ | Dengue virus type I upstream primer. | 45 |
| GAGCCCCGTCCAAGGACGTAAA ATGEJ | Dengue virus type I upstream primer. | 46 |
| GAGCCCCGTCCAAGGACGTTAA AAGAA | Dengue virus types II & III upstream primer. | 47 |
| GAGCCCCGTCCAAGGACGTTAA AAGAJ | Dengue virus types II & III upstream primer. | 48 |
| GAGCCCCGTCCAAGGACGTTAA AAGEJ | Dengue virus types II & III upstream primer. | 49 |
| ATTGAAGTCAGGCCACTTGTGC CA | Dengue virus type IV upstream primer. | 50 |
| ATTGAAGTCAGGCCACTTGTGC CJ | Dengue virus type IV upstream primer. | 51 |
| ATTGAAGTCAGGCCACTTGTGC UJ | Dengue virus type IV upstream primer. | 52 |
| GATCTCTGGTCTTTCCCAGCGT CAA | Dengue virus downstream primer. | 53 |
| GATCTCTGGTCTTTCCCAGCGT CAJ | Dengue virus downstream primer. | 54 |
| GATCTCTGGTCTTTCCCAGCGT CEJ | Dengue virus downstream primer. | 55 |

Definition of primer suffixes:
J = t-butyl-benzyl-dA,
E = methyl-dA;
U = ethyl-dC In some embodiments, one "upstream" primers and a "downstream" primer are used in combination to amplify a Dengue virus nucleic acid. In some embodiments more than one upstream primer is used in combination with at least one downstream primer to detect one or more Dengue virus nucleic acids. The use of multiple upstream primers in a single amplification reaction allows for the amplification and/or detection of different Dengue virus nucleic acid variants. For example, in some embodiments, a first upstream primer (selected from SEQ ID NO:41, SEQ ID NO:42 and SEQ ID NO:43) and a second upstream primer (selected from SEQ ID NO:50, SEQ ID NO:51, and SEQ ID NO:52) are used in combination with a Dengue virus downstream primer (e.g., selected from a primer comprising SEQ ID NO:53, SEQ ID NO:54, and SEQ ID NO:55). These embodiments are useful, e.g., to detect any the Dengue virus types 1, 2, 3, or 4.

Yellow Fever Virus Primers

Additional primers of the invention hybridize to the yellow fever virus 3' UTR. Exemplary primers useful for amplifying and/or detecting Dengue virus nucleic acids include those depicted in Table 3.

TABLE 3

| Sequence | Comments | SEQ ID NO: |
|---|---|---|
| AACCGGGATAAAAACTACGGGTG GAGAA | Yellow fever virus upstream primer. | 56 |
| AACCGGGATAAAAACTACGGGTG GAGAJ | Yellow fever virus upstream primer. | 57 |
| AACCGGGATAAAAACTACGGGTG GAGEJ | Yellow fever virus upstream primer. | 58 |
| ATAAAAACTACGGGTGGAGAACCG GA | Yellow fever virus upstream primer. | 59 |
| ATAAAAACTACGGGTGGAGAACCG GJ | Yellow fever virus upstream primer. | 60 |
| ACTCCGGTCTTTCCCTGGCGTCAA | Yellow fever virus downstream primer. | 61 |
| ACTCCGGTCTTTCCCTGGCGTCAJ | Yellow fever virus downstream primer. | 62 |
| ACTCCGGTCTTTCCCTGGCGTCEJ | Yellow fever virus downstream primer. | 63 |

In some embodiments, one "upstream" primers and a "downstream" primer are used in combination to amplify a yellow fever virus nucleic acid. In some embodiments more than one upstream primer is used in combination with at least one downstream primer to detect one or more yellow fever virus nucleic acids. Multiple upstream primers may be used in a single amplification reaction. For example, in some embodiments, a first upstream primer (e.g., selected from SEQ ID NO:56, SEQ ID NO:57 and SEQ ID NO:58) and a second upstream primer (e.g., selected from SEQ ID NO:59, SEQ ID NO:60, and SEQ ID NO:61) are used in combination with a yellow fever virus downstream primer (e.g., selected from a primer comprising SEQ ID NO:62 and SEQ ID NO:63).

Primers Based on the Sequences of FIG. 7

Additional primers of the invention hybridize to any of the sequences depicted in FIG. 7 (e.g., SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40), or a complement thereof, under conditions to allow for priming of an amplification reaction. In some cases, these primers are useful for amplifying and/or detecting nucleic acids from SLEV.

Like the primers that hybridize to SEQ IDNO:1 described above, primers that hybridize to any of the sequences depicted in FIG. 7 can also comprise non-standard nucleotides according to the definitions of oligonucleotide and primers recited above.

The length and composition of the primers that hybridize to any of the sequences depicted in FIG. 7 can be chosen to give sufficient thermodynamic stability to ensure hybridization of the primer to the flaviviral nucleic acid under the appropriate reaction conditions, which depend on the detection method to be performed. For example, primers with modified, non-standard, or derivatized nucleotides may be longer or shorter than those with conventional nucleotides while having similar thermodynamic hybridization properties. Thus, in certain embodiments, the second nucleic acid primer comprises modified, non-standard, or derivatized bases as defined above. Primers that hybridize to any of the sequences depicted in FIG. 7 can comprise at least, e.g., 4, 5, 6, 7, 8, 9, 10, 11, 12, 13, 14, 15, 16, 17, 18, 19, 20, 21, 22, 23, 24, 25, 30, 40, 50 or more contiguous nucleotides of any of the sequences depicted in FIG. 7 or a complement thereof.

Those of skill in the art will appreciate that primer pairs can be designed using SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40 to amplify desired sequences from the 3' UTR region of SLEV. In some embodiments, a first primer of the invention hybridizes to TTGA-CACCTGGAAAGACAGGAGA (SEQ ID NO: 68 and a second primer hybridizes to the complement of CAAAGCCCCTCATTCCGACTCGGG (SEQ ID NO: 69) under conditions to allow for priming of an amplification reaction.

Exemplary primers for detecting and/or amplifying SLEV include those depicted in Table 4.

TABLE 4

| Sequence | Comments | SEQ ID NO: |
|---|---|---|
| CAAAGCCCCTCATTCCGACTCGGG A | St. Louis encephalitis virus upstream primer. | 64 |
| CAAAGCCCCTCATTCCGACTCGGG J | St. Louis encephalitis virus upstream primer. | 65 |
| TCTCCTGTCTTTCCAGGTGTCAA | St. Louis encephalitis virus downstream primer. | 66 |
| TCTCCTGTCTTTCCAGGTGTCAJ | St. Louis encephalitis virus downstream primer. | 67 |

3.2. Nucleic Acid Probes

In another aspect, the invention provides a probe for the detection of a nucleic acid of certain flaviviruses. Flaviviral nucleic acids that can be detected with the probes of the invention are described in Sections 3.3 and 3.4, below. The probe can be any nucleic acid probe that can be used to identify the presence of a nucleic acid of a detectable flavivirus known to one of skill in the art without limitation. Typically, the probe comprises a nucleotide sequence that hybridizes to a region in a nucleic acid of a flavivirus to be detected.

The probe nucleotide sequence can be of any length sufficient to specifically bind a nucleic acid of a flavivirus to be detected. In certain embodiments, the probe comprises at least about 6 nucleotides. In certain embodiments, the probe comprises fewer than about 140 nucleotides. In certain embodiments, the probe can be about 18 to about 25, about 25 to about 35, or about 35 to about 45 nucleotides in length. The length and composition of the probe can be chosen to give sufficient thermodynamic stability to ensure hybridization of the probe to the flaviviral nucleic acid under the appropriate reaction conditions, which depend on the detection method to be performed. For example, probes with modified, non-standard, or derivatized nucleotides may be longer or shorter than those with conventional nucleotides while having similar thermodynamic hybridization properties. Examples of such non-standard bases may be found in U.S. Pat. Nos. 6,320,005, 6,174,998, 6,001,611, and 5,990,303, each of which is hereby incorporated by reference in its entirety. As another example, probes with G/C-rich sequences may anneal to target sequences at higher temperatures that a probe of similar length with A/T-rich sequences.

Typically, the portion of the probe nucleotide sequence that hybridizes to the detectable nucleic acid is identical or complementary to the region of the detectable nucleic acid to which the probe hybridizes. However, this portion of the probe can have less than 100% sequence identity or complementarity to the region of the detectable viral nucleic acid to which the probe hybridizes. In certain embodiments of the invention, nucleotide sequence of the portion of the probe that hybridizes to the detectable viral nucleic acid can have about 99%, about 98%, about 97%, about 96%, about 95%, about 90%, about 85% or about 80% complementarity or identity to the region of the detectable viral nucleic acid to which the probe hybridizes.

In certain embodiments, the invention provides a probe for detecting a member of the Japanese encephalitis virus serogroup comprising a nucleic acid that hybridizes to a nucleic acid of SEQ ID NO.: 16. SEQ ID NO.: 16, as presented in FIG. 3, represents a region of conserved sequence in the 3' untranslated region of the genomes of the flaviviruses that can be detected using the compositions and methods of the present invention. FIG. 3 also shows that SEQ ID NO.: 17 represents the complement to SEQ ID NO.: 16.

In such embodiments of the invention, the probe has a nucleotide composition, i.e., chemical structure, that allows it to hybridize under the defined conditions to a nucleic acid of SEQ ID NO.: 16. For example, a probe containing a standard nucleotide that hybridizes to a C residue in the nucleic acid of SEQ ID NO.: 16 must have a G residue in the corresponding position. Thus, hybridization to the nucleic acid of SEQ ID NO.: 16 defines the nucleotide sequence and therefore the exact chemical structure of the probe. In addition, the probe can also comprise non-standard nucleotides according to the definitions of oligonucleotide and primers recited above. Certain of such non-standard nucleotides can also bind to other standard or non-standard nucleotides to form a base-pair. For example, the nonstandard nucleotide inosine can pair with uracil, cytosine, and adenine. Given the known correlation between hybridization and chemical structure, one of skill in the art can easily recognize the standard features of the probes of the invention. Exemplary embodiments are described in detail below.

In certain embodiments, the probes that can hybridize to SEQ ID NO.: 16 comprise about 10, about 12, about 14, about 15, about 16, about 17, about 18, about 19, about 20, about 21, about 22, about 23, about 24, about 25, about 26, about 27, about 28, about 29, about 30, about 32, about 34, about 36, about 38, about 40, about 42, about 44, about 46, about 48, about 50, about 55, about 60, about 65, about 70, about 75, or about 80 nucleotides. In certain embodiments, the probe comprises modified, non-standard, or derivatized bases, as defined above.

In certain embodiments, the probe comprises at least about 20 consecutive nucleotides of SEQ ID NO.: 17. In other embodiments, the probe comprises at least about 22 consecutive nucleotides of SEQ ID NO.: 17. In still other embodiments, the probe comprises at least about 24 consecutive nucleotides of SEQ ID NO.: 17. In yet other embodiments, the probe comprises at least about 26 consecutive nucleotides of SEQ ID NO.: 17. In still other embodiments, the probe comprises at least about 28 consecutive nucleotides of SEQ ID NO.: 17. In yet other embodiments, the probe comprises at least about 30 consecutive nucleotides of SEQ ID NO.: 17. In still other embodiments, the probe comprises at least about 32 consecutive nucleotides of SEQ ID NO.: 17. In yet other embodiments, the probe comprises at least about 34 consecutive nucleotides of SEQ ID NO.: 17. In still other embodiments, the probe comprises at least about 36 consecutive nucleotides of SEQ ID NO.: 17. In yet other embodiments, the probe comprises at least about 38 consecutive nucleotides of SEQ ID NO.: 17. In still other embodiments, the probe comprises at least about 40 consecutive nucleotides of SEQ ID NO.: 17.

In certain embodiments, the invention provides particular nucleic acid probes that can be used to detect a member of the Japanese encephalitis virus serogroup, as well as certain other flaviviruses. These probes can be structurally defined by reference to their nucleic acid sequences, as presented in Table 5.

TABLE 5

| | |
|---|---|
| SEQ ID NO.: 18<br>Probe for Detecting<br>Flaviviruses | GGN$^3$CTAGN$^8$GGTTAGAGGAGACCCN$^{24}$N$^{25}$N$^{26}$N$^{27}$N$^{28}$<br>Wherein N$^3$ A or T; N$^8$ is A or T; N$^{24}$ is C or T; N$^{25}$ is G, C, T, A, or absent; N$^{26}$ is C, T, G, or absent; N$^{27}$ is G, C, A, T, or absent; and N$^{28}$ is G, C, A, T, or absent. |
| SEQ ID NO.: 19<br>Probe for Detecting<br>Japanese Encephalitis<br>Virus Serogroup<br>Members | GGACTAGN$^8$GGTTAGAGGAGACCCCN$^{25}$N$^{26}$N$^{27}$N$^{28}$<br>Wherein N$^8$ is A or T; N$^{25}$ is G or A; N$^{26}$ is C or T; N$^{27}$ is G or T; and N$^{28}$ is G or T. |
| SEQ ID NO.: 20<br>Probe for Detecting West<br>Nile Virus | GGACTAGN$^8$GGTTAGAGGAGACCCCN$^{25}$CGN$^{28}$<br>Wherein N$^8$ is A or T; N$^{25}$ is G or A; and N$^{28}$ is G or T. |
| SEQ ID NO.: 21<br>Probe for Detecting<br>Japanese Encephalitis<br>Virus | GGACTAGAGGTTAGAGGAGACCCCGN$^{26}$GG<br>Wherein N$^{26}$ is C or T. |
| SEQ ID NO.: 22<br>Probe for Detecting<br>Murray Valley<br>Encephalitis Virus | GGACTAGAGGTTAGAGGAGACCCCACTC |
| SEQ ID NO.: 23<br>Probe for Detecting<br>Kunjin Virus | AATAN$^5$GTGGATTACATGAN$^{19}$TTCAN$^{24}$TGAAG<br>Wherein N$^5$ is T or C; N$^{19}$ is G or C; and N$^{24}$ is T or C. |
| SEQ ID NO.: 24<br>Probe for Detecting<br>Dengue Virus | GGACTAGAGGTTAGAGGAGACCCCN$^{25}$N$^{26}$N$^{27}$N$^{28}$<br>Wherein N$^{25}$ is C or T; N$^{26}$ is C or G; N$^{27}$ is C or G; and N$^{28}$ is G, C or A. |
| SEQ ID NO.: 25<br>Probe for Detecting<br>Yellow Fever Virus | GGTCTAGAGGTTAGAGGAGACCCTCCAG |
| SEQ ID NO.: 26<br>Probe for Detecting<br>Montana Myotis<br>Leukencephalitis Virus | GGACTAGAGGTTAGAGGAGACCCCTTCC |
| SEQ ID NO.: 27<br>Probe for Detecting<br>Modoc Virus | GGACTAGAGGTTAGAGGAGACCCCGGC |
| SEQ ID NO.: 28<br>Example Probe 1 | GGACTAGAGGTTAGAGGAGACCCCGCGG |
| SEQ ID NO.: 70<br>Flavivirus anti-sense<br>probe | GGGTCTCCTCTAACCTCTAGTCCTTCCCCC |

In certain embodiments of the invention, the probe comprises any of SEQ ID NOS.: 18-28 or 70, or complements thereof.

The nucleic acid probes of the invention can additionally comprise other nucleic acid sequences that are not derived from and/or do not hybridize to a nucleic acid of a member of the Japanese encephalitis virus serogroup or another flavivirus that can be detected with the disclosed probes. These additional nucleic acid sequences can be selected by one of skill in the art to provide desired functionality to the probes. For example, the nucleic acid probes can comprise additional sequences that allow improved methods of detection. Examples of probes that can comprise additional nucleic acid sequences or can otherwise be adapted for use in the probes, methods, and kits of the invention can be found in U.S. Pat. Nos. 6,323,337, 6,248,526, 6,150,097, 6,117,635, 6,090,552, 5,866,336, and 5,723,591, each of which is hereby incorporated by reference in its entirety. Further, methods of detecting a nucleic acid, including a nucleic acid of a member of the Japanese encephalitis virus serogroup or other detectable flaviviruses are extensively described in Sections 4.2 and 4.3, below. Certain of these methods also use additional nucleic acid sequences that can be present in the nucleic acid primers of the invention; such additional nucleic acid sequences and methods of using these additional sequences to detect a member of the Japanese encephalitis virus serogroup are described below.

The nucleic acid probes of the invention can be prepared by any method known to one of skill in the art without limitation. In particular, the methods used to prepare the nucleic acid primers of the invention described above may also be used to prepare the nucleic acid probes of the invention.

In addition to the probe nucleotide sequence, the probe can comprise additional nucleotide sequences or other moieties that do not inhibit the methods of the instant invention. In convenient embodiments of the invention, the probe can comprise additional nucleotide sequences or other moieties that facilitate the methods of the instant invention. For instance, the probe can be blocked at its 3' terminus to prevent undesired nucleic acid polymerization priming by the probe. Also, moieties may be present within the probe that stabilize or destabilize hybridization of the probe or probe fragments with the nucleotide sequence. The probes of the invention can also comprise modified, non-standard, or derivatized nucleotides as defined above.

In certain embodiments of the invention, the probe can comprise a detectable moiety. The detectable moiety can be any detectable moiety known by one of skill in the art without limitation. Further, the detectable moiety can be detectable by any means known to one of skill in the art without limitation. For example, the detectable moiety can be detectable by spectroscopic, photochemical, biochemical, immunochemical, or chemical means.

A variety of detectable moieties that can be used to detect the probes of the invention, as well as methods for their linkage to the probe, are known to the art and include, but are not limited to, enzymes (e.g., alkaline phosphatase and horseradish peroxidase) and enzyme substrates, radioactive moieties, fluorescent moieties, chromophores, chemiluminescent labels, electrochemiluminescent labels, such as Origin™ (Igen, Rockville, Md.), ligands having specific binding partners, or any other labels that may interact with each other to enhance, alter, or diminish a signal. Of course, should a 5' nuclease reaction be performed using a thermostable DNA polymerase at elevated temperatures, the detectable moiety should not be degraded or otherwise rendered undetectable by such elevated temperatures.

In certain embodiments, the detectable moiety can be a fluorescent moiety. The fluorescent moiety can be any fluorescent moiety known to one of skill in the art without limitation. In general, fluorescent moieties with wide Stokes shifts are preferred, allowing the use of fluorometers with filters rather than monochromometers and increasing the efficiency of detection. In certain embodiments, the fluorescent moiety can be selected from the group consisting of fluorescein-family dyes (Integrated DNA Technologies, Inc., Coralville, Iowa), polyhalofluorescein-family dyes, hexachlorofluorescein-family dyes, coumarin-family dyes (Molecular Probes, Inc., Eugene, Oreg.), rhodamine-family dyes (Integrated DNA Technologies, Inc.), cyanine-family dyes, oxazine-family dyes, thiazine-family dyes, squaraine-family dyes, chelated lanthanide-family dyes, and BODIPY®-family dyes (Molecular Probes, Inc.). In a preferred embodiment, the fluorescent moiety is 6-carboxyfluorescein (FAM™) (Integrated DNA Technologies, Inc.). Other examples of fluorescent moieties that can be used in the probes, methods, and kits of the invention can be found in U.S. Pat. Nos. 6,406,297, 6,221,604, 5,994,063, 5,808,044, 5,880,287, 5,556,959, and 5,135,717, each of which is hereby incorporated by reference in its entirety.

In other embodiments, the detectable moiety can be a detectable moiety other than a fluorescent moiety. Among radioactive moieties, $^{32}$P-labeled compounds are preferred. Any method known to one of skill in the art without limitation may be used to introduce $^{32}$P into a probe. For example, a probe may be labeled with 32P by 5' labeling with a kinase or by random insertion by nick translation. Detectable moieties that are enzymes can typically be detected by their activity. For example, alkaline phosphatase can be detected by measuring fluorescence produced by action of the enzyme on appropriate substrate compounds. Where a member of specific binding partners are used as detectable moieties, the presence of the probe can be detected by detecting the specific binding of a molecule to the member of the specific binding partner. For example, an antigen can be linked to the probe, and a monoclonal antibody specific for that antigen can be used to detect the presence of the antigen and therefore the probe. Other specific binding partners that can be used as detectable moieties include biotin and avidin or streptavidin, IgG and protein A, and numerous other receptor-ligand couples well-known to the art. Still other examples of detectable moieties that are not fluorescent moieties can be found in U.S. Pat. Nos. 5,525,465, 5,464,746, 5,424,414, and 4,948,882, each of which is hereby incorporated by reference in its entirety.

The above description of detectable moieties is not meant to categorize the various labels into distinct classes, as the same label may serve in several different modes. For example, $^{125}$I may serve as a radioactive moiety or as an electron-dense reagent. Horseradish peroxidase may serve as enzyme or as antigen for a monoclonal antibody. Further, one may combine various detectable moieties for desired effect. For example, one might label a probe with biotin, and detect its presence with avidin labeled with $^{125}$I, or with an anti-biotin monoclonal antibody labeled with horseradish peroxidase. Other permutations and possibilities will be readily apparent to those of ordinary skill in the art, and are considered as equivalents within the scope of the instant invention.

The method of linking or conjugating the detectable moiety to the probe depends, of course, on the type of detectable moiety or moieties used and the position of the detectable moiety on the probe.

The detectable moiety may be attached to the probe directly or indirectly by a variety of techniques. Depending on the precise type of detectable moiety used, the detectable moiety can be located at the 5' or 3' end of the probe, located internally in the probe's nucleotide sequence, or attached to spacer arms of various sizes and compositions to facilitate signal interactions. Using commercially available phosphoramidite reagents, one can produce oligonucleotides containing functional groups (e.g., thiols or primary amines) at either terminus via an appropriately protected phosphoramidite, and can attach a detectable moiety thereto using protocols described in, for example, PCR Protocols: A Guide to Methods and Applications, ed. by Innis et al., Academic Press, Inc., 1990.

Methods for introducing oligonucleotide functionalizing reagents to introduce one or more sulflhydryl, amino or hydroxyl moieties into the oligonucleotide probe sequence, typically at the 5' terminus are described in U.S. Pat. No. 4,914,210. A 5' phosphate group can be introduced as a radioisotope by using polynucleotide kinase and [gamma-$^{32}$P] ATP to provide a reporter group. Biotin can be added to the 5' end by reacting an aminothymidine residue or alkylamino linker, introduced during synthesis, with an N-hydroxysuccinimide ester of biotin. Other methods of attaching a detectable moiety, including a fluorescent moiety, to the probe can be found in U.S. Pat. No. 5,118,802, which is hereby incorporated by reference in its entirety.

It is also possible to attach a detectable moiety at the 3' terminus of the probe by employing, for example, polynucleotide terminal transferase to add a desired moiety, such as, for example, cordycepin $^{35}$S-DATP, and biotinylated dUTP.

Oligonucleotide derivatives are also detectable moieties that can be used in the probes, methods and kits of the present invention. For example, etheno-dA and etheno-A are known fluorescent adenine nucleotides which can be incorporated into an oligonucleotide probe. Similarly, etheno-dC is another analog that could be used in probe synthesis. The probes containing such nucleotide derivatives can be degraded to release mononucleotides that are much more strongly fluorescent than the intact probe by, for example, a polymerase's 5' to 3' nuclease activity.

In certain embodiments of the invention, a probe can be labeled with more than one detectable moiety. In certain of such embodiments, each detectable moiety can be individually attached to different bases of the probe. In other embodiments, more than one detectable moiety can be attached to the same base of the probe.

In certain embodiments, the detectable moiety can be attached to the 5' end of the probe. In other embodiments, the detectable moiety can be attached to the probe at a residue that is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, about 35, or about 40 residues from the 5' end of the probe. In certain embodiments, the detectable moiety can be attached to the 3' end of the probe. In other embodiments, the detectable moiety can be attached to the probe at a residue that is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, about 35, or about 40 residues from the 3' end of the probe. The detectable moiety can be attached to any portion of a residue of the probe. For example, the detectable moiety can be attached to a sugar, phosphate, or base moiety of a nucleotide in the probe. In other embodiments, the detectable moiety can be attached between two residues of the probe.

In certain embodiments of the invention, the probe can comprise a fluorescent moiety and a quencher moiety. In such embodiments, the fluorescent moiety can be any fluorescent moiety known to one of skill in the art, as described above. Further, the quencher moiety can be any quencher moiety known to one of skill in the art without limitation. In certain embodiments, the quencher moiety can be selected from the group consisting of fluorescein-family dyes, polyhalofluorescein-family dyes, hexachlorofluorescein-family dyes, coumarin-family dyes, rhodamine-family dyes, cyanine-family dyes, oxazine-family dyes, thiazine-family dyes, squaraine-family dyes, chelated lanthanide-family dyes, BODIPY®-family dyes, and non-fluorescent quencher moieties. In certain embodiments, the non-fluorescent quencher moieties can be BHQ™-family dyes (including the quenchers described in WO 01/86001), Iowa Black™, or Dabcyl (Integrated DNA Technologies, Inc.). Other examples of specific quencher moieties include, for example, but not by way of limitation, TAMRA (N,N,N',N'-tetramethyl-6-carboxyrhodamine) (Molecular Probes, Inc.), DABCYL (4-(4'-dimehtylaminophenylazo)benzoic acid), Iowa Black™ (Integrated DNA Technologies, Inc.), Cy3™ (Integrated DNA Technologies, Inc.) or Cy5™ (Integrated DNA Technologies, Inc.). In a preferred embodiment, the quencher moiety is Cy5™. Other examples of quencher moieties that can be used in the probes, methods, and kits of the invention can be found in U.S. Pat. Nos. 6,399,392, 6,348,596, 6,080,068, and 5,707,813, each of which is hereby incorporated by reference in its entirety.

In certain embodiments, the quencher moiety can be attached to the 5' end of the probe. In other embodiments, the quencher moiety can be attached to the probe at a residue that is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, about 35, or about 40 residues from the 5' end of the probe. In certain embodiments, the quencher moiety can be attached to the 3' end of the probe. In other embodiments, the quencher moiety can be attached to the probe at a residue that is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, about 35, or about 40 residues from the 3' end of the probe. In some embodiments, the quencher moiety is attached to the 5' end of the probe and the fluorescent moiety is attached to a residue that is within about 10 residues of the 5' end of the probe. The quencher moiety can be attached to any portion of a residue of the probe. For example, the quencher moiety can be attached to a sugar, phosphate, or base moiety of a nucleotide in the probe. In other embodiments, the quencher moiety can be attached between two residues of the probe.

While not intending to be bound to any particular theory or mechanism of action, it is believed that when the probe is intact, a photon emitted by the fluorescent moiety can be absorbed and thus quenched by the quencher moiety. The quencher moiety then either releases the energy of the photon as a photon of different wavelength or as heat. Thus, the quencher moiety can also be a fluorescent moiety. As described above, this phenomenon is termed fluorescence resonance energy transfer ("FRET"). Cleaving the probe between the fluorescent moiety and quencher results in a reduction in quenching of the fluorescent moiety's emitted fluorescence by the quencher moiety.

Generally, transfer of energy between the fluorescent moiety and the quencher moiety depends on the distance between the fluorescent moiety and the quencher moiety and the critical transfer distance of the particular fluorescent moiety-quencher moiety pair. The critical transfer distance is both characteristic and constant for a given fluorescent moiety paired with a given quencher moiety. Further, the spatial relationship of the fluorescent moiety in reference to the quencher moiety can be more sensitively determined when the critical transfer distance of the fluorescent moiety-quencher moiety pair is close to the distance between the fluorescent moiety and the quencher moiety. Accordingly, the skilled practitioner can select the fluorescent moiety and the quencher moiety to have a critical transfer distance that is close to the distance separating the fluorescent moiety from the quencher moiety on the probe. Critical transfer distances of particular fluorescent moiety-quencher moiety pairs are well known in the art and can be found, for example, in an article by Wu and Brand, 1994, Anal. Biochem. 218:1-13, which is hereby incorporated by reference in its entirety.

Other criteria for section of particular fluorescent moiety-quencher moiety pairs include, for example, the quantum yield of fluorescent emission by the fluorescent moiety; the wavelength of fluorescence emitted by the fluorescent moiety; the extinction coefficient of the quencher moiety; the wavelength of fluorescence, if any, emitted by the quencher moiety; and the quantum yield of fluorescent emission, if any, by the quencher moiety. In addition, if the quencher moiety is also a fluorescent moiety, the quencher moiety and the fluorescent moiety can preferably be selected so that fluorescence emitted by one can easily be distinguished from fluorescence emitted by the other. Further guidance on the selection of particular fluorescent moiety-quencher moiety pairs may be found in a review article by Klostermeier and Millar, 2002, Biopolymers 61:159-179, which is hereby incorporated by reference in its entirety.

Exemplary combinations of fluorescent moieties and quencher moieties that can be used in this aspect of the invention include, but are not limited to, the fluorescent moiety rhodamine 590 and the quencher moiety crystal violet. A preferred combination of fluorescent and quencher moieties is the fluorescent moiety 6-carboxyfluorescein and the quencher moiety Cy5™. Other examples of fluorescent moiety-quencher moiety pairs that can be used in the probes, methods, and kits of the invention can be found in U.S. Pat. No. 6,245,514, which is hereby incorporated by reference in its entirety.

Examples of molecules that can be used as both fluorescent or quencher moieties in FRET include fluorescein, 6-carboxyfluorescein, 2'7'-dimethoxy-4'5'-dichloro-6-carboxyfluorescein, rhodamine, 6-carboxyrhodamine, 6-carboxy-X-rhodamine, and 5-(2'-aminoethyl)aminonaphthalene-1-sulfonic acid (EDANS). Whether a fluorescent moiety is a donor or an acceptor is defined by its excitation and emission spectra, and the fluorescent moiety with which it is paired. For example, FAM™ is most efficiently excited by light with a wavelength of 488 nm, and emits light with a spectrum of 500 to 650 nm, and an emission maximum of 525 nm. Accordingly, FAM™ is a suitable fluorescent moiety for use with, for example, with TAMRA as quencher moiety, which has at its excitation maximum 514 nm.

In some embodiments, the following probe variants are used:

FGGACTAGAIGGTTAGAGGAGACCCCGCGGP (SEQ ID NO:76, which is a variant of SEQ ID NO:28);

FGGAEUAGAIGGUUAGAGGAGAEEEEGEGGP (SEO ID NO:77, which is a variant of SEQ ID NO:28);

FGGGTCTCCITCTAACCTCTAGTCCTTCCCCCP (SEQ ID NO:78, which is a variant of SEQ ID NO:70);

FGGGUEUEEIUEUAACCTCTAGTCCTTCCCCCP (SEQ ID NO:79, which is a variant of SEQ ID NO:70); and FGGTCTAGAIGGTTAGAGGAGACCCTCCAGP (SEQ ID NO:80, which is a variant of SEQ ID NO:25). In all of the above probes, F=CY5; I=FAM; P=PO4; U=propynyl dU; E=5-methyl-dC).

3.3. Nucleic Acids of Detectable Members of the Japanese Encephalitis Virus Serogroup The primers, probes, methods, and kits of the invention are useful for the detection of certain members of the genus Flavivirus. In particular, the primers, probes, methods, and kits are useful for detecting members of the Japanese encephalitis virus serogroup. For example, the members of the Japanese encephalitis virus serogroup that can be detected according to the present invention include, but are not limited to, Japanese encephalitis virus, West Nile virus, Murray Valley encephalitis virus, SLEV, and Kunjin virus. In several instances, the complete sequence of at least one strain of some of these viruses has been determined. These sequences may be found by reference to the GenBank accession numbers presented in FIG. 4, which presents an alignment of nucleic acid sequences of Japanese encephalitis virus serogroup members with the oligonucleotides of the invention. The nucleic acid sequences of each flaviviral genome identified by accession number in FIG. 4 is hereby incorporated by reference in its entirety.

The complete nucleic acid sequences of the genomes of other members of the Japanese encephalitis virus serogroup, e.g., Cacipacore virus, St. Louis encephalitis virus, Usutu virus, and Youende virus, have not yet been determined. Nonetheless, it is believed that the primers and probes of the present invention hybridize to sequences that have a high degree of conservation with all members of the Japanese encephalitis virus serogroup. Further, one of skill in the art can easily recognize that the primers and probes can hybridize to a nucleic acid from one of the as yet unsequenced members following determination of the nucleic acid sequences of these viral genomes.

In certain embodiments, a nucleic acid of a member of the Japanese encephalitis virus serogroup can be detected. In other embodiments, a nucleic acid of Japanese encephalitis virus can be detected. In yet other embodiments, a nucleic acid of West Nile virus can be detected. In still other embodiments, a nucleic acid of Kunjin virus can be detected. In yet other embodiments, a nucleic acid of Murray Valley encephalitis virus can be detected. In yet other embodiments, a nucleic acid of SLEV can be detected. In still other embodiments, a nucleic acid of Japanese encephalitis virus, West Nile virus, SLEV or Murray Valley encephalitis virus can be detected.

The nucleic acid to be detected can be any nucleic acid from a detectable flavivirus as described herein. Typically, the nucleic acid will be a single-stranded RNA, as the flaviviruses to be detected have plus-strand single stranded RNA genomes. However, the nucleic acid to be detected can also be DNA corresponding in sequence to an RNA genome of a flavivirus that can be detected. Such DNA can be prepared, for example, by reverse-transcribing the viral RNA as described in Section 4.1, below.

The presence of a nucleic acid of a detectable flavivirus can be detected in a sample from any source known to one of skill in the art without limitation. For example, the viral nucleic acid can be detected in a biological sample, as defined above. The viral nucleic acid can be detected in a sample from any natural source, including a vertebrate animal, such as a fish, amphibian, reptile, bird, or mammal, and an invertebrate animal, such as insects, crustaceans, arachnids, etc. In addition, the sample to be tested can be from a non-living source, such as a water or soil sample or a swipe sample, such as is derived from testing a surface.

It certain embodiments of the invention, the nucleic acid to be detected can be amplified according to methods known to those of skill in the art. The amplification can be performed prior to detection according to the methods described herein or the amplification can be performed concurrently with detection as described herein. Methods of amplifying a nucleic acid are described below and in, for example, Saiki et al., 1988, Science 239:487-91, the contents of which are hereby incorporated by reference in their entirety.

3.4. Nucleic Acids of Other Detectable Flaviviruses

The probes, methods and kits of the invention can also be used to detect a nucleic acid from other flaviviruses, including, but not limited to, Dengue virus, Montana myotis leukoencephalitis virus, Modoc virus, and Yellow Fever virus. As with members of the Japanese encephalitis virus serogroup, the nucleic acid sequences of at least one strain of some of these viruses has been determined. These sequences may be found by reference to the accession numbers presented in FIG. 5, which presents an alignment of nucleic acid sequences of these detectable flaviviruses with SEQ ID NO:16. The nucleic acid sequences of each flaviviral genome identified by GenBank accession number in FIG. 5 is hereby incorporated by reference in its entirety.

As discussed herein, primers SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO:48, SEQ ID NO:49, SEQ ID NO:50, SEQ ID NO:51, SEQ ID NO:52, SEQ ID NO:53, SEQ ID NO:54, and SEQ ID NO:55 are useful for amplifying and/or detecting Dengue virus and primers SEQ ID NO: 56, SEQ ID NO: 57, SEQ ID NO: 58, SEQ ID NO: 59, SEQ ID NO: 60, SEQ ID NO: 61, SEQ ID NO: 62, and SEQ ID NO:63 are useful for amplifying and/or detecting yellow fever virus.

3.5. Multiplex Amplification Reactions to Detect Different Virus Variants or Different Viruses The primers and probes of the invention can be combined in reactions to detect more than one viral nucleic acid. For example, in some cases, multiple upstream and/or multiple downstream primers are combined in one reaction mixture for use in detecting different viral variants (e.g., that would not be detected, or would only be poorly detected by a single primer or primer pair). In some embodiments, multiple upstream and/or multiple downstream primers are combined in one reaction mixture to detect more than one virus. In such embodiments, primers specific for each virus to be detected are included in the reaction mixture, thereby allowing for amplification of each viral nucleic acid present in a sample. For example, any combination of primers for amplification of West Nile Virus, SLEV, Dengue virus and yellow fever virus can be included depending on what virus is desired to be detected. Detection of multiple viruses using a single reaction is useful, for example, when screening the blood supply or in other cases where contamination with any virus is all that needs to be detected.

Probes of the invention can be used in the reactions described above. Depending on what result is desired, a single probe capable of detecting any possible viral nucleic acid product can be used. Alternatively, a different probe that specifically hybridizes to each possible viral nucleic acid product can be used. In such cases, it can be useful to employ a different detectable label with each probe, thereby allowing for differentiation of viral nucleic acid products.

In some embodiments, multiplex PCR can be used to detect multiple viral nucleic acids using the components described above. Multiplex PCR allows for amplification and/or detection of multiple polynucleotide fragments in the same reaction. See, e.g., PCR PRIMER, A LABORATORY MANUAL (Dieffenbach, ed. 1995) Cold Spring Harbor Press, pages 157-171.

In some embodiments, primers for the detection of both West Nile virus and SLEV are used. In some embodiments, primers for the detection of West Nile virus, SLEV, and Dengue virus are used. In some embodiments, primers for the detection of West Nile virus, SLEV, and yellow fever virus are used. In some embodiments, primers for the detection of West Nile virus, SLEV, yellow fever and Dengue virus are used. In some cases, the multiplex reactions further comprise at least one probe as described herein.

4. Methods for Detecting and/or Quantifying a Nucleic Acid of a Member of the Japanese Encephalitis Serogroup and Certain other Flaviviruses In certain aspects, the present invention provides methods for using nucleic acid primers and probes to detect a nucleic acid of certain flaviviruses. In other aspects, the present invention provides methods for using nucleic acid primers and probes to quantify a nucleic acid of certain flaviviruses in a sample. Any method for using nucleic acid primers and probes to detect a nucleic acid known to one of skill in the art without limitation can be used to detect a nucleic acid of a detectable flavivirus, as described above. In certain embodiments, the methods provide using a primer and a probe to detect a nucleic acid of a member of the Japanese encephalitis virus serogroup. In other embodiments, the methods provide using two primers and a probe to detect a nucleic acid of a member of the Japanese encephalitis virus serogroup. In still other embodiments, the methods provide using a probe to detect certain flaviviruses, as described below.

4.1. 5' Nuclease Reaction-Based Assays for Detecting and/or Quantifying a Nucleic Acid of a Member of the Japanese Encephalitis Serogroup In certain aspects of the invention, the methods comprise detecting a nucleic acid of a member of the Japanese encephalitis virus serogroup with a primer and a probe. These methods generally comprise contacting a primer hybridized to a nucleic acid of a member of the Japanese encephalitis virus serogroup with an enzyme with 5' nuclease activity. The enzyme with 5' nuclease activity then fragments a probe hybridized to the nucleic acid of the member of the Japanese encephalitis virus serogroup in a 5' nuclease reaction. The probe can be labeled with a detectable moiety that enables detection of fragmentation of the probe. Such methods are based on those described in U.S. Pat. Nos. 6,214,979, 5,804, 375, 5,487,972 and 5,210,015, each of which is hereby incorporated by reference in its entirety.

In a 5' nuclease reaction, the nucleic acid, primer and probe can be contacted with any enzyme known by one of skill in the art to have 5' to 3' nuclease activity without limitation. The conditions are preferably chosen to permit the polymerase to cleave the probe and release a plurality of fragments of the probe from the nucleic acid. Preferred enzymes with 5' nuclease activity include template-dependent nucleic acid polymerases. Known native and recombinant forms of such polymerases include, for example, *E. coli* DNA polymerase I (Fermentas, Inc., Hanover, Md.), *Bacillus stearothermophilus* DNA polymerase, and *Thermococcus littoralis* DNA polymerase.

In preferred embodiments, the enzymes with 5' nuclease activity are thermostable and thermoactive nucleic acid polymerases. Such thermostable polymerases include, but are not limited to, native and recombinant forms of polymerases from a variety of species of the eubacterial genera *Thermus, Thermatoga,* and *Thermosipho*. For example, *Thermus* species polymerases that can be used in the methods of the invention include *Thermus aquaticus* (Taq) DNA polymerase, *Thermus thermophilus* (Tth) DNA polymerase, *Thermus* species Z05 (Z05) DNA polymerase, and *Thermus* species sps17 (sps17), as described in U.S. Pat. Nos. 5,405, 774, 5,352,600, 5,079,352, 4,889,818, 5,466,591, 5,618,711, 5,674,738, and 5,795,762, each of which is incorporated herein by reference in its entirety. *Thermatoga* polymerases that can be used in the methods of the invention include, for example, *Thermatoga maritima* DNA polymerase and *Thermatoga neapolitana* DNA polymerase, while an example of a *Thermosipho* polymerase that can be used is *Thermosipho africanus* DNA polymerase. The sequences of *Thermatoga maritima* and *Thermosipho africanus* DNA polymerases are published in International Patent Application No. PCT/US91/07035 with Publication No. WO 92/06200, which is incorporated herein by reference in its entirety. The sequence of *Thermatoga neapolitana* may be found in International Patent Publication No. WO 97/09451, which is incorporated herein by reference in its entirety.

A 5' nuclease reaction comprises contacting the nucleic acid to be detected with a primer, a probe, and an enzyme having 5' to 3' nuclease activity, under conditions in which the primer and the probe hybridize to the nucleic acid. Components of a 5' nuclease reaction can contact the nucleic acid to be detected in any order, e.g., the primer can contact the nucleic acid to be detected first, followed by the probe and enzyme with 5' nuclease activity, or alternatively the enzyme with 5' nuclease activity can contact the nucleic acid to be detected first, followed by the probe and primer. In certain embodiments, more than one primer or probe may be added to a 5' nuclease reaction. In certain preferred embodiments, a pair of primers can contact the nucleic acid in a 5' nuclease reaction. The primer can be any primer capable of priming a DNA synthesis reaction. Where only one primer is used, the primer should hybridize to the nucleic acid upstream of the probe, i.e., the 3' end of the primer should point toward the 5' end of the probe. The 3' end of the primer can hybridize adjacent to the 5' end of the probe, or the 3' end of the primer can hybridize further upstream of the 5' end of the probe. Where more than one primer is used, at least one primer should hybridize to the nucleic acid to be detected upstream of the probe, as described above.

Certain embodiments of the 5' nuclease reactions of the present invention are based on several 5' nuclease reactions that are known to those of skill in the art. Examples of such reactions are described in detail, for instance, in U.S. Pat. No. 5,210,015, the content of which is hereby incorporated by reference in its entirety.

Briefly, in a 5' nuclease reaction, a target nucleic acid is contacted with a primer and a probe under conditions in which the primer and probe hybridize to a strand of the nucleic acid. The nucleic acid, primer and probe are also contacted with an enzyme, for example a nucleic acid polymerase, having 5' to 3' nuclease activity. Nucleic acid polymerases possessing 5' to 3' nuclease activity can cleave the probe hybridized to the nucleic acid downstream of the primer. The 3' end of the primer provides a substrate for extension of a new nucleic acid as based upon the template nucleic acid by the nucleic acid polymerase. As the polymerase extends the new nucleic acid, it encounters the 5' end of the probe and begins to cleave fragments from the probe.

The primer and probe can be designed such that they hybridize to the target nucleic acid in close proximity to each other such that binding of the nucleic acid polymerase to the 3' end of the primer puts it in contact with the 5' end of the probe. In this process, nucleic acid extension is not required to bring the nucleic acid polymerase into position to accomplish the cleavage. The term "polymerization-independent cleavage" refers to this process.

Alternatively, if the primer and probe anneal to more distantly spaced regions of the nucleic acid, nucleic acid extension must occur before the nucleic acid polymerase encounters the 5' end of the probe. As the polymerization continues, the polymerase progressively cleaves fragments from the 5' end of the probe. This cleaving continues until the remainder of the probe has been destabilized to the extent that it dissociates from the template molecule. The term "polymerization-dependent cleavage" refers to this process.

One advantage of polymerization-independent cleavage lies in the elimination of the need for amplification of the nucleic acid. In the absence of primer extension, the strand of the nucleic acid is substantially single-stranded. Provided the primer and probe are adjacently bound to the nucleic acid, sequential rounds of oligonucleotide annealing and cleavage of fragments can occur. Thus, sufficient amounts of the probe can be fragmented to yield a detectable signal, thereby permitting detection in the absence of polymerization.

In either process, a sample is provided which contains the nucleic acid. If the nucleic acid is double-stranded, it should first be denatured, e.g., the strands of the nucleic acid separated from each other. Any suitable denaturing method, including physical, chemical, or enzymatic means, known to one of skill in the art without limitation can be used to separate the nucleic acid strands. A preferred physical means for strand separation is heating the nucleic acid until it is completely (>99%) denatured. Typical heat denaturation involves temperatures ranging from about 80° C. to about 105° C., for about 10 seconds to about 10 minutes. As an alternative to denaturation, the nucleic acid may exist in a single-stranded form in the sample, such as, for example, single stranded RNA or DNA viruses.

It should be noted that the viruses that can be detected with the primers, probes, methods, and kits of the invention are single stranded plus-strand RNA viruses. Accordingly, denaturation of the native viral genome is not required to detect an unamplified viral genome. However, if the native viral genome is reverse-transcribed into DNA according to certain embodiments of the invention, described below, denaturation of the amplified viral nucleic acids is necessary prior to detection with the primers and probes of the invention.

If the nucleic acid to be detected is RNA, the RNA can either be used as an RNA template for a 5' nuclease reaction as described above, or the RNA can be used as a template for reverse-transcription into cDNA, or both simultaneously. In certain embodiments, the RNA can be detected without reverse-transcription into cDNA using the methods of the invention. Polymerization-independent cleavage methods as described above are particularly well-suited for such embodiments. In other embodiments, the RNA can be first reverse-transcribed into cDNA in the absence of a probe, and then the cDNA product can be detected according to the methods of the invention. In still other embodiments, the RNA can be reverse-transcribed in the presence of a probe, simultaneously producing cDNA that can subsequently be amplified and/or detected and detecting the presence of the RNA by assessing fragmentation of the probe as described herein.

Where the RNA is reverse-transcribed in the absence of a probe, the RNA can be reverse transcribed into cDNA by any method known to one of skill in the art. The products of such reverse transcription can then be detected like any detectable nucleic acid according to the methods described herein.

Where the RNA is reverse-transcribed in the presence of a probe, the RNA can be reverse-transcribed by a DNA polymerase with 5'-3' nuclease activity that can use RNA as a template for DNA strand synthesis. As with all known DNA polymerase synthesis activities, such synthesis requires the presence of a primer, such as those described herein. The DNA polymerase that can use RNA is a template is preferably thermostable, so that multiple cycles of denaturation and DNA synthesis can occur without destroying the polymerase. Further, the DNA polymerase used for reverse transcription can preferably also synthesize DNA using a DNA template. Such polymerases are described in, for example, U.S. Pat. No. 6,468,775 (*Carboxydothermus hydrogenformans* DNA polymerase), U.S. Pat. No. 5,968,799 (*Thermosipho africanus* DNA polymerase), U.S. Pat. No. 5,736,373 (*Bacillus pallidus* DNA polymerase), U.S. Pat. No. 5,674,738 (*Thermus* species Z05 DNA polymerase), and U.S. Pat. No. 5,407,800 (*Thermus aquaticus* and *Thermus thermophilus* DNA polymerases), each of which is incorporated herein by reference in its entirety. In addition, methods and compositions for reverse transcribing an RNA using a thermostable DNA polymerase with reverse transcription activity are described in U.S. Pat. Nos. 5,693,517, 5,561,058, 5,405,774, 5,352,600, 5,310,652, and 5,079,352, each of which is incorporated herein by reference in its entirety.

Whether RNA or DNA, the denatured nucleic acid strand is then contacted with a primer and a probe under hybridization conditions, which enable the primer and probe to bind to the nucleic acid strand. In certain embodiments, two primers can be used to amplify the nucleic acid. In such embodiments, the two primers can be selected so that their relative positions along the nucleic acid are such that an extension product synthesized from one primer, after the extension produce is separated from its template (complement), can serve as a template for the extension of the other primer to yield an amplified product of defined length. The length of the product depends on the length of the sequence between the two primers and the length of the two primers themselves.

Because the complementary strands are typically longer than either the probe or primer, the strands have more points of contact and thus a greater chance of finding and binding each other over any given period of time. A high molar excess of probe and primer helps shift the equilibrium toward primer and probe annealing rather than template reannealing.

The primer should be sufficiently long to prime the synthesis of extension products in the presence of the agent for polymerization. The exact length and composition of the primer can depend on many factors, including temperature of the annealing reaction, source and composition of the primer, proximity of the probe annealing site to the primer annealing site, and ratio of primer:probe concentration. For example, depending on the complexity of the sequence, an oligonucleotide primer typically contains about 15-30 nucleotides, although it may contain fewer or more nucleotides. The primers must be sufficiently complementary to selectively anneal to their respective strands and form stable duplexes.

Each primer can be selected to be "substantially" complementary to a strand of the nucleic acid. The primers need not reflect the exact sequence of the template, but must be sufficiently complementary to selectively hybridize to their respective strands under the appropriate reaction conditions. Non complementary bases or longer sequences can be interspersed into the primer or located at the ends of the primer, provided the primer retains sufficient complementarity with its template strand to form a stable duplex therewith. The non-complementary nucleotide sequences of the primers may include restriction enzyme sites. Any non-complementary nucleotide sequences are preferably not at the 3' end of the primer.

The probe preferably hybridizes to the nucleic acid to be detected before the polymerase binds the nucleic acid and primer and begins to extend the new nucleic acid strand from the primer based upon the template of the detectable nucleic acid. It is possible for the polymerase to bind the primer and nucleic acid to be detected before the probe contacts the detectable nucleic acid; however, this arrangement can result in decreased probe fragmentation unless multiple cycles of primer extension are performed, as in a preferred PCR based 5' nuclease reaction as described below. Accordingly, it is preferable that the probe hybridize to the nucleic acid to be detected before primer extension by the polymerase begins.

A variety of techniques known to one of skill in the art can be employed to enhance the likelihood that the probe will hybridize to the detectable nucleic acid before primer extension polymerization reaches this duplex region, or before the polymerase attaches to the upstream oligonucleotide in the polymerization-independent process. For example, short primer molecules generally require cooler temperature to form sufficiently stable hybrid complexes with the nucleic acid. Therefore, the probe can be designed to be longer than the primer so that the probe anneals preferentially to the nucleic acid at higher temperatures relative to primer annealing.

One can also use primers and probes having differential thermal stability based upon their nucleotide composition. For example, the probe can be chosen to have greater G/C content and, consequently, greater thermal stability than the primer. Alternatively or additionally, one or more modified, non-standard or derivatized DNA bases may be incorporated into primers or probes to result in either greater or lesser thermal stability in comparison to primers or probes having only conventional DNA bases. Examples of such modified, non-standard or derivatized bases may be found in U.S. Pat. Nos. 6,320,005, 6,174,998, 6,001,611, and 5,990,303, each of which is hereby incorporated by reference in its entirety.

Further, the temperature of the reaction can also be varied to take advantage of the differential thermal stability of the probe and primer. For example, following denaturation at high temperatures as described above, the reaction can be incubated at an intermediate temperature which permits probe but not primer binding, followed by a further temperature reduction to permit primer annealing and subsequent extension.

A high molar excess of probe to primer concentration can also be used to preferentially favor binding of the probe before the primer. Such probe concentrations are typically in the range of about 2 to 20 times higher than the respective primer concentration, which is generally $0.5\text{-}5 \times 10^{-7}$ M.

Template-dependent extension of the oligonucleotide primer(s) is catalyzed by a DNA polymerase in the presence of adequate amounts of the four deoxyribonucleoside triphosphates (dATP, dGTP, dCTP, and dTTP) or analogs, e.g., dUTP, as discussed above, in a reaction medium which is comprised of the appropriate salts, metal cations, and pH buffering system. Suitable polymerizing agents are enzymes known to catalyze primer and template-dependent DNA synthesis and possess the 5' to 3' nuclease activity. Such enzymes include, for example, *Escherichia coli* DNA polymerase I, *Thermus thermophilus* DNA polymerase, *Bacillus stearothermophilus* DNA polymerase, *Thermococcus littoralis* DNA polymerase, *Thermus aquaticus* DNA polymerase, *Thermatoga maritima* DNA polymerase and *Thermatoga neapolitana* DNA polymerase and Z05 DNA polymerase. Further, the reaction conditions for performing DNA synthesis using these DNA polymerases are well known in the art. To be useful in the methods of the present invention, the polymerizing agent should possess 5' nuclease activity that can efficiently cleave the oligonucleotide and release labeled fragments so that a detectable signal is directly or indirectly generated.

The products of the synthesis are duplex molecules consisting of the template strands and the primer extension strands. Byproducts of this synthesis are probe fragments which can consist of a mixture of mono-, di- and oligonucleotide fragments. In preferred embodiments, repeated cycles of denaturation, probe and primer annealing, and primer extension and cleavage of the probe can be performed, resulting in exponential accumulation of the amplified region defined by the primers and exponential generation of labeled fragments. Such repeated thermal cycling is generally known in the art as the polymerase chain reaction (PCR). Sufficient cycles can be performed to achieve fragment a sufficient amount of the probe to distinguish positive reactions, i.e., the nucleic acid to be detected is present, from negative reactions, i.e., the nucleic acid to be detected is not present. Generally, positive reactions will exhibit a signal that is several orders of magnitude greater than a negative reaction.

In certain preferred embodiments, the PCR reaction is carried out as an automated process which utilizes a thermostable enzyme. In this process the reaction mixture is cycled through a denaturing step, a probe and primer annealing step, and a synthesis step, whereby cleavage and displacement occur simultaneously with primer dependent template extension. A thermal cycler, such as the ABI3700 (Applied Biosystems, Inc., Foster City, Calif.), which is specifically designed for use with a thermostable enzyme, may be employed. In certain of such embodiments of the invention, the nucleic acids to be detected can be amplified in the absence of a detectably-labeled probe, followed by detection of the amplification product in a separate reaction. Alternatively, the nucleic acids to be detected can be amplified in the presence of the probe, allowing amplification and detection in a single reaction.

Temperature stable polymerases are preferred in this automated process because the preferred way of denaturing the double stranded extension products is by exposing them to a high temperature (about 95° C.) during the PCR cycle. For example, U.S. Pat. No. 4,889,818 discloses a representative thermostable enzyme isolated from *Thermus aquaticus*. Additional representative temperature stable polymerases include, e.g., polymerases extracted from the thermostable bacteria *Thermus flavus, Thermus ruber, Thermus thermophilus, Bacillus stearothermophilus* (which has a somewhat lower temperature optimum than the others listed), *Thermus lacteus, Thermus rubens, Thermotoga maritima, Thermococcus littoralis, Methanothermusfervidus*, and *Pyrococcus furiosus* (Stratagene, La Jolla, Calif.). As described above, certain of these thermostable polymerases can synthesize DNA from an RNA template. Where an RNA molecule is to be detected according to the methods of the invention, a DNA polymerase that can synthesize DNA from an RNA template, i.e., with reverse transcription activity, should be used.

In other aspects, the methods of the present invention can also be used to quantify an amount of a nucleic acid of a member of the Japanese encephalitis virus serogroup in a sample. In such methods, a 5' nuclease reaction as described above is performed, and the amount of fluorescence produced is quantified. The amount of fluorescence can be quantified by any method known to one of skill in the art without limitation. In certain embodiments, the amount of fluorescence emitted can be quantified with a fluorometer. This amount of fluorescence can be compared to the amount of fluorescence emitted by a control reaction. The control reaction is preferably performed with the same reagents and at the same time as the reaction performed with the sample with a known amount of nucleic acid of a member of the Japanese encephalitis virus serogroup. Alternatively, the amount of fluorescence emitted by the fluorescent moiety can be compared to a standard curve plotting fluorescence against viral nucleic acid concentration. A representative standard curve is presented in FIG. 6. Further guidance in quantifying an amount of a nucleic acid of a member of the Japanese encephalitis virus serogroup can be found in published U.S. Patent Application Publication No. 2002/0058262 and European Patent Nos. 1 138 780, 1 138 783, and 1 138 784.

4.2. Other Methods for Detecting a Nucleic Acid of a Member of the Japanese Encephalitis Serogroup that Use One or More Primers and a Probe In addition to the 5' nuclease reactions described above, the invention further provides other methods can be used to be used to detect a nucleic acid of a member of the Japanese encephalitis virus serogroup, as described below.

In certain embodiments, any method known by one of skill in the art that uses two nucleic acid primers and a nucleic acid probe to detect a nucleic acid can be used to detect a nucleic acid of a member of the Japanese encephalitis virus serogroup. The nucleic acid primers and probes described Sections 3.1 and 3.2 can be used in any such method known to one of skill in the art, without limitation. Exemplary amplification reactions that can be used to detect the viral nucleic acids include, e.g., polymerase chain reaction (PCR) and ligase chain reaction (LCR) (see U.S. Pat. Nos. 4,683,195 and 4,683,202; *PCR Protocols: A Guide to Methods and Applications* (Innis et al., eds, 1990)), strand displacement amplification (SDA) (Walker, et al. *Nucleic Acids Res.* 20(7):1691-6 (1992); Walker *PCR Methods Appl* 3(1):1-6 (1993)), transcription-mediated amplification (Phyffer, et al., *J. Clin. Microbiol.* 34:834-841 (1996); Vuorinen, et al. , *J. Clin. Microbiol.* 33:1856-1859 (1995)), nucleic acid sequence-based amplification (NASBA) (Compton, *Nature* 350(6313):91-2 (1991), rolling circle amplification (RCA) (Lisby, *Mol. Biotechnol.* 12(1):75-99 (1999)); Hatch et al., *Genet. Anal.* 15(2):35-40 (1999)) branched DNA signal amplification (bDNA) (see, e.g., Iqbal et al., *Mol. Cell Probes* 13(4):315-320 (1999)) and Q-Beta Replicase (Lizardi et al., *Bio/Technology* 6:1197 (1988)).

One example of such methods is amplifying a nucleic acid of a member of the Japanese encephalitis serogroup and detecting the presence of the nucleic acid with a probe that is a molecular beacon. Such probes contain a target recognition sequence that can hybridize to a flanked by complementary sequences that can form a hairpin. The molecular beacon has a fluorescent moiety and a quencher moiety on opposite ends of the probe. Hybridization of the molecular beacon to the nucleic acid of a member of the Japanese encephalitis serogroup separates the fluorescent moiety from the quencher moiety allowing detection of the fluorescent moiety, and thus revealing the presence of the nucleic acid of a member of the Japanese encephalitis serogroup. Any probe of the invention may be used in such methods with the addition of several residues on the 5' and 3' ends of the probe that one of skill in the art recognizes as capable of forming a hairpin structure. Further guidance in selection and use of molecular beacons may be found in an article by Tyagi and Kramer, 1996, *Nat. Biotechnol.* 14:303-308, which is hereby incorporated by reference in its entirety.

In still another example, two primers and a probe of the invention may be used to detect a nucleic acid of a member of the Japanese encephalitis serogroup using nucleic acid sequence-based amplification. Nucleic acid sequence-based amplification (NASBA) is a robust amplification technology that can be used to detect a nucleic acid of a member of the Japanese encephalitis serogroup. In NASBA methods, three enzymes are used, including reverse transcriptase, T7 RNA polymerase, and RNase H. The final amplification product is single-stranded RNA with a polarity opposite that of the nucleic acid to be detected. The amplified RNA product can be detected through the use of a target-specific capture probe bound to magnetic particles in conjunction with a ruthenium-labeled detector probe and an instrument (NucliSens Reader; bioMérieux) capable of measuring electrochemiluminescence (ECL). Alternatively, RNA amplified by NASBA can specifically be detected in real time by including molecular beacon probes in the amplification reaction, as described above. Further guidance on use of the primers and probes of the invention may be found in articles by Compton, 1991, Nature 350:91-92 and Kievits et al., 1991, J. Virol. Methods 35:273-86, each of which is hereby incorporated by reference in its entirety.

Other examples of such methods include the 5' nuclease reactions described extensively above. Another example of such methods include amplification of a nucleic acid of a member of the Japanese encephalitis serogroup with two primers of the invention, followed by detection of the amplified nucleic acid with a probe of the invention. Still other examples of such methods that may be used or adapted by one of skill in the art to detect a nucleic acid of a member of the Japanese encephalitis virus serogroup may be found in U.S. Pat. Nos. 6,403,339, 6,329,152, 5,952,202, and 5,387,510, each of which is hereby incorporated by reference in its entirety.

In other embodiments, any method known by one of skill in the art that uses a nucleic acid primer and a nucleic acid probe to detect a nucleic acid can be used to detect a nucleic acid of a member of the Japanese encephalitis virus serogroup. The nucleic acid primers and probes described Sections 3.1 and 3.2 can be used in any such method known to one of skill in the art, without limitation. In certain of these methods, one of skill in the art will recognize that a primer of the invention may also be used as a probe, and a probe of the invention used as a primer.

For example, a nucleic acid of a member of the Japanese encephalitis virus serogroup can be hybridized to a primer of the invention that is bound to a solid support. A detectably-labeled probe of the invention can then be hybridized to the nucleic acid to be detected, thereby indicating the presence of the nucleic acid. Alternatively, the probe can be bound to the solid support and used to capture the nucleic acid, and then the primer can be detectably labeled and hybridized to the nucleic acid, thereby indicating the presence of the nucleic acid.

Another example of methods that use a nucleic acid primer and a probe to detect a nucleic acid of a member of the Japanese encephalitis virus serogroup involves the use of nanoparticles. In such methods, two oligonucleotides, such as a primer or probe of the invention, that can hybridize to different regions of a nucleic acid to be detected are covalently linked to a nanoparticle. The nanoparticles are contacted with a nucleic acid of a member of the Japanese encephalitis virus serogroup under hybridization conditions. If the nucleic acid is present, the nucleic acid will bind to the oligonucleotides attached to the nanoparticles, producing a large molecular weight complex that can be detected. The complex can be detected by any method known to one of skill in the art without limitation. In certain embodiments, the complex is detected by precipitation of the complex. Further guidance on methods of using nanoparticles in connection with the primers and probes of the invention may be found in Taton et al., 2000, Science 289(5485):1757-60 and U.S. Pat. Nos. 6,506,564, 6,495,324, 6,417,340, 6,399,303, and 6,361,944.

In yet another example, rolling circle amplification ("RCA") can be used as part of a method for detecting a nucleic acid of a member of the Japanese encephalitis virus serogroup. In certain embodiments of RCA methods, a DNA circle is amplified by polymerase extension of a complementary primer. Any of the primers or probes of the invention can be used in such methods. Methods of circularizing DNA are well known in the art, and include, for example, ligating the ends of a DNA molecule together under conditions which favor intramolecular ligation. The single-stranded product concatamer product can then be detected by any method of detecting a nucleic acid known to one of skill in the art without limitation. For example, the concatamer product can be detected using a detectably-labeled probe of the invention. Other examples of methods of detecting a nucleic acid of known sequence are extensively described herein. In other embodiments of RCA, a second primer can be used that is complementary to the concatamer product. This primer allows exponential amplification of the sequences present in the circular DNA template. The products of the amplification can still be detected, for example, by using a detectably-labeled probe of the invention. Further guidance on using the primers and probes of the invention in RCA methods for detecting a nucleic acid of a member of the Japanese encephalitis virus serogroup may be found in U.S. Pat. Nos. 6,344,329, 6,350,580, 6,221,603, 6,210,884, 5,648,245, and 5,714,320 and international patent publication no. WO95/35390, each of which is hereby incorporated by reference in its entirety.

Still another example of such methods is the polymerization-independent 5' nuclease reaction described above. Still other examples of methods of using a primer and a probe that can be used or adapted by one of skill in the art to detect a member of the Japanese encephalitis virus serogroup are described in U.S. Pat. Nos. 6,316,200, 6,268,128, 6,180,338, 5,716,784, and 5,573,906, each of which is hereby incorporated by reference in its entirety.

In certain embodiments, any assay known by one of skill in the art that uses two nucleic acid primers that can amplify a nucleic acid to detect the nucleic acid can be used to detect a nucleic acid of a member of the Japanese encephalitis virus serogroup. The nucleic acid primers described in Section 3.1 can be used in any such method known to one of skill in the art, without limitation. In addition, one of skill in the art will recognize that a probe of the invention may also be used as a primer in certain of these methods.

In one example of such methods, a nucleic acid of a member of the Japanese encephalitis virus serogroup can be detected by amplifying the nucleic acid with at least one primer that comprises a hairpin structure containing a fluorescent moiety and a quencher moiety at the 5' end of the molecule. Incorporation of the primer into the amplification product can then separate the fluorescent moiety from the quencher moiety, allowing detection of the fluorescent moiety. Detection of the fluorescent moiety reveals the presence of the nucleic acid of a member of the Japanese encephalitis virus serogroup. One of skill in the art will easily recognize the use of the primers or probes of the invention in such methods by incorporating additional residues in the primer or probe to form the necessary hairpin structure. Further guidance in design and selection of such primers and probes may be found in Nazerenko et al., 1997, Nucleic Acids Res.

25:2516-2521 and in Thelwell et al., 2000, Nucleic Acids Res. 28:3752-3761, each of which is hereby incorporated by reference in its entirety.

In another example of such methods, a nucleic acid of a member of the Japanese encephalitis virus serogroup can be detected using Strand Displacement Amplification ("SDA"). In such methods, amplified Japanese encephalitis virus serogroup nucleic acids are detected by incorporation of a single-stranded primer that comprises a fluorescent moiety, a quencher moiety, and an engineered restriction site separating the two moieties. One of skill in the art can easily recognize how to modify any of the primers or probes of the invention for use in SDA.

In a first amplification reaction used in SDA, the primer is used to amplify the nucleic acid of a member of the Japanese encephalitis serogroup in the presence of, for example, thio-dCTP, thereby incorporating the primer into the amplification product. Then, a restriction endonuclease can be used to nick the restriction site in the primer. The restriction endonuclease cannot cut both strands of the amplification product because of the incorporation of thio-dCTP in the amplification product. Finally, the 3' end of the primer created by the nick can be used to prime a new polymerization reaction, thereby displacing the portion of the strand 3' to the nick from the template strand. Displacement of the strand separates the fluorescent moiety from the quencher moiety, thereby preventing quenching of fluorescence emitted by the fluorescent moiety. The nucleic acid of a member of the Japanese encephalitis serogroup can thereby be detected and/or quantified by measuring the presence and/or amount of fluorescence. Further guidance on selection and modification of primers and probes for use in SDA may be found in Little et al., 1999, Clin. Chem. 45-777-784 and U.S. Pat. Nos. 6,528,254 and 6,528,632, each of which is hereby incorporated by reference in its entirety.

In another example, a nucleic acid of a member of the Japanese encephalitis serogroup may be detecting using transcription-mediated amplification ("TMA"). TMA is an RNA transcription amplification system that uses RNA polymerase and reverse transcriptase to amplify the nucleic acids to be detected. In the method, a primer of the invention with a promoter for RNA polymerase is used to prime reverse transcription of an RNA of a member of the Japanese encephalitis virus serogroup. The RNAse activity of reverse transcriptase then degrades the RNA template, releasing the cDNA strand. Second strand synthesis is primed with a second primer of the invention and catalyzed by reverse transcriptase. RNA polymerase then recognizes the promoter synthesized in the second strand and catalyzes multiple cycles of RNA transcription from the second strand. The RNA product can then be detected or can serve as template for another round of amplification.

The RNA product of TMA can then be detected by any method known to one of skill in the art. In certain embodiments, the RNA product can be detected with a probe of the invention. In other embodiments, the RNA product can be detected with a probe of the invention that has been labeled with an acridine-ester label (Gen-Probe, Inc., San Diego, Calif.). Such labels can be chemically removed from unhybridized probe while labels on hybridized probes remain undisturbed. Thus, in such embodiments, presence of a nucleic acid of a member of the Japanese encephalitis virus serogroup can be detected by detecting the presence of the acridine-ester label. Further guidance in using the primers and probes of the invention in TMA-based methods may be found in Arnold et al., 1989, Clin. Chem. 35:1588-1594, Miller et al., 1994, J. Clin. Microbiol. 32-393-397, and U.S. Pat. Nos. 6,335,166 and 6,294,338, each of which is hereby incorporated by reference in its entirety.

In yet another example, a nucleic acid of a member of the Japanese encephalitis virus serogroup can be detected using diagnostic PCR. In such methods, the presence of a nucleic acid to be detected is indicated by the successful template-dependent amplification of a PCR product. Generally, the identity of the PCR product can be determined from the size of the PCR product; successful amplification of the nucleic acid to be detected will generally result in a PCR product of known size. Methods for determining the size of a nucleic acid, such as a PCR product, are well-known to the art and include, for example, gel and capillary electrophoresis, among others.

Other methods of detecting successful amplification of a PCR product thereby revealing the presence of a member of the Japanese encephalitis serogroup include using non-specific DNA binding dyes. For example, SYBR® Green (Molecular Probes, Inc., Eugene, Oreg.) can be included in the amplification reaction, which allows the detection and quantification of any double-stranded DNA generated during PCR. Examples of such methods may be found in U.S. Pat. Nos. 6,323,337 and 5,863,753, each of which is incorporated by reference in its entirety.

Finally, other methods that can be used or adapted by one of skill in the art to use the primers and probes of the invention to detect a member of the Japanese encephalitis virus serogroup are described in U.S. Pat. Nos. 6,528,632, 6,475,729, 6,361,944, 6,329,152, 6,270,967, 6,258,546, 6,063,603, 6,057,099, 6,040,166, 5,914,230, 5,843,650, 5,747,255, 5,747,251, 5,731,146, 5,712,386, 5,635,347, 5,554,517, 5,409,818, 5,384,242, 4,965,188, 4,868,104, 4,800,159, and 4,683,195, each of which is hereby incorporated by reference in its entirety.

In other embodiments, any assay known by one of skill in the art that uses a single nucleic acid primer or probe that can hybridize to a nucleic acid to detect the nucleic acid can be used to detect a nucleic acid of a member of the Japanese encephalitis virus serogroup. The nucleic acid primers and probes described in Section 3.1 and 3.2 can be used in any such method known to one of skill in the art, without limitation. In addition, one of skill in the art will recognize that a primer of the invention may also be used as a probe, and a probe of the invention used as a primer in certain of the described methods.

For example, a nucleic acid of a member of the Japanese encephalitis virus serogroup can be detected using a primer to initiate a primer extension reaction. Successful extension of the primer by a nucleic acid polymerase indicates the presence of the nucleic acid of a member of the Japanese encephalitis virus serogroup. A primer extension product that indicates the presence of a member of the Japanese encephalitis virus serogroup can be detected by any method known to one of skill in the art. For example, the primer extension reaction can incorporate $^{32}$P-labeled or fluorescently-labeled nucleotides.

Other examples of single primer or probe detection methods that describe methods that can be used as described or adapted by one of skill in the art to detect a member of the Japanese encephalitis virus serogroup can be found in U.S. Pat. Nos. 6,440,707, 6,379,888, 6,368,803, 6,365,724, 6,361, 944, 6,352,827, 6,326,145, 6,312,906, 6,268,128, 6,261,784, 6,177,249, 6,140,055, 6,130,047, 6,124,090, 6,121,001, 6,110,677, 6,054,279, 6,022,686, 5,981,176, 5,958,700, 5,945,283, 5,935,791, 5,919,630, 5,888,739, 5,888,723, 5,882,867, 5,876,924, 5,866,336, 5,856,092, 5,853,990, 5,846,726, 5,814,447, 5,808,036, 5,800,989, 5,795,718, 5,792,614, 5,710,028, 5,683,875, 5,683,872, 5,679,510, 5,641,633, 5,597,696, 5,595,890, 5,571,673, 5,547,861, 5,525,462, 5,514,546, 5,491,063, 5,437,977, 5,294,534, 5,118,605, 5,102,784, 4,994,373, 4,851,331, 4,767,700, and 4,683,194, each of which is hereby incorporated by reference in its entirety.

Certain of the above-referenced U.S. patents disclose methods that can use either one or two primers, or either one or two primers and a probe. The above description is not meant to categorize such methods. Methods of detecting a nucleic acid using, for example, two primers provided in a U.S. patent that is described as providing a method for detecting a nucleic acid using a single primer are also incorporated by reference and can be used with the primers, probes, and kits of the invention.

4.3. Methods for Detecting a Nucleic Acid of a Member of the Japanese Encephalitis Serogroup and Certain Other Flaviviruses Using a Probe In addition to the assays for detecting a nucleic acid of a member of the Japanese encephalitis virus serogroup described above, the invention further provides methods for detecting a nucleic acid of a member of the Japanese encephalitis virus serogroup and certain other flaviviruses. The flaviviruses that can be detected according to these methods are described in Section 3.4, above.

In certain embodiments, any method known to one of skill in the art that uses a nucleic acid probe to detect a nucleic acid can be used to detect a nucleic acid of a member of the Japanese encephalitis virus serogroup and certain other flaviviruses. Nucleic acid probes that can be used to detect nucleic acids of members of the Japanese encephalitis virus serogroup and certain other flaviviruses are described in Section 3.2, above.

In certain embodiments, the probes of the invention can be used to determine if viral sequences of nucleic acids of members of the Japanese encephalitis virus serogroup and certain other flaviviruses are present in a sample by determining if the probes bind to the viral sequences present in the sample. For example, the detection can be accomplished using a dot blot format. In the dot blot format, the unlabeled amplified sample is bound to a solid support, such as a membrane, the membrane incubated with labeled probe under suitable hybridization conditions, the unhybridized probe removed by washing, and the filter monitored for the presence of bound probe. When multiple samples are analyzed with a single probe, the dot blot format is quite useful. Many samples can be immobilized at discrete locations on a single membrane and hybridized simultaneously by immersing the membrane in a solution of probe.

An alternate method that is quite useful when large numbers of different probes are to be used is a "reverse" dot blot format, in which the amplified sequence contains a label, and the probe is bound to the solid support. This format would be useful if the assay methods of the present invention were used as one of a battery of methods to be performed simultaneously on a sample. In this format, the unlabeled probes are bound to the membrane and exposed to the labeled sample under appropriately stringent hybridization conditions. Unhybridized labeled sample is then removed by washing under suitably stringent conditions, and the filter is then monitored for the presence of bound sequences.

Both the forward and reverse dot blot assays can be carried out conveniently in a microtiter plate; see U.S. patent application Ser. No. 695,072, filed May 3, 1991, which is a CIP of U.S. patent application Ser. No. 414,542, filed Sep. 29, 1989, now abandoned, each of which is incorporated herein by reference in its entirety. The probes can be attached to bovine serum albumen (BSA), for example, which adheres to the microliter plate, thereby immobilizing the probe.

Another example of a method of using a probe of the invention to detect a nucleic acid of members of the Japanese encephalitis virus serogroup and certain other flaviviruses is described in U.S. Pat. No. 6,383,756, which provides a method for detecting a nucleic acid bound to a membrane, and which is hereby incorporated by reference in its entirety.

In another example, a nucleic acid of a member of the Japanese encephalitis virus serogroup can be detected using branched-DNA-based methods. In such methods, a dendrimer monomer is constructed of two DNA strands that share a region of sequence complementarity located in the central portion of each strand. When the two strands anneal to form the monomer the resulting structure has a central double-stranded center bordered by four single-stranded ends. A dendrimer can be assembled from monomers by hybridization of the single stranded ends of the monomers to each other, while still leaving many single-stranded ends free. These free single-stranded ends can have the sequences of any of the primers or probes of the invention. A dendrimer can be detectably-labeled with any detectable moiety known to one of skill in the art without limitation, as described above in connection with the probes of the invention.

Dendrimers can then be used as a probe, in, for example, the "dot blot" assays described below. In addition, a dendrimer can be used as a probe in any method known to one of skill in the art in which the probe is directly detected. A probe is directly detected when the presence of the probe can be determined without any subsequent reaction or modification, such as a dot blot or Southern hybridization. Further guidance on the selection and use of dendrimers as probes to detect a nucleic acid of a member of the Japanese encephalitis serogroup or other detectable flaviviruses may be found in U.S. Pat. No. 6,261,779 and in Nilsen et al., 1997, J. Theoretical Biology 187:273-284, Capaldi et al., 2000, Nucleic. Acids Res., 28(7):21e, Wang et al., 1998, J. Am. Chem. Soc. 120: 8281-8282, and Wang et al., 1998, Electroanalysis 10(8):553-556, each of which is hereby incorporated by reference in its entirety.

One of skill in the art will recognize that the probes of the invention can be used in combination with any primer that selectively hybridizes to a virus that can be detected with the probes of the invention. Accordingly, it is intended that methods of detecting a detectable flavivirus with a probe of the invention in combination with any primers that selectively hybridize to a detectable flavivirus fall within the scope of the present invention.

Any method that uses a single primer or probe that can be used to detect a nucleic acid of a member of the Japanese encephalitis virus serogroup described in Section 4.2, above, can be used with a probe of the invention to detect other flaviviruses described in Section 3.4, above.

5. Kits

In another aspect, the present invention provides kits that can be used to detect a nucleic acid of a Japanese encephalitis virus serogroup member and/or certain other flaviviruses. The members of the Japanese encephalitis virus serogroup that can be detected with the kits of the invention are described in Section 3.3, above, while the nucleic acids of other flaviviruses that can be detected with the kits of the invention are described in Section 3.4, above.

In certain embodiments, the kit comprises a probe of the invention. In some embodiments, the kit comprises a primer of the invention. In some embodiments, the kit comprises a combination of one or more of the primers and probes of the invention.

For example, in one embodiment the kit comprises a first nucleic acid primer that hybridizes to a nucleic acid of SEQ ID NO.: 1 and a second nucleic acid primer that hybridizes to a nucleic acid of SEQ ID NO.: 9. In other embodiments, the kits comprise a primer (e.g., at least one upstream and/or one downstream primer) comprising a polynucleotide that hybridizes to SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40 or a complement thereof. Exemplary primers may be selected from, e.g., SEQ ID NO:64, SEQ ID NO:65, SEQ ID NO:66, and SEQ ID NO:67.

In some embodiments, the kits comprise at least one upstream and/or one downstream primer selected from SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO:48, SEQ ID NO:49, SEQ ID NO:50, SEQ ID NO:51, SEQ ID NO:52, SEQ ID NO:53, SEQ ID NO:54, or SEQ ID NO:55.

In other embodiments, the kits comprise at least one upstream and/or one downstream primer selected from SEQ ID NO: 56, SEQ ID NO: 57, SEQ ID NO: 58, SEQ ID NO: 59, SEQ ID NO: 60, SEQ ID NO: 61, SEQ ID NO: 62, or SEQ ID NO:63.

In some of the above-described embodiments, the kits also comprise a nucleic acid probe that hybridizes to a nucleic acid of SEQ ID NO.: 16, or the complement thereof, as described herein.

In certain embodiments, the kits comprise two nucleic acid primers and a nucleic acid probe for detecting a nucleic acid of a member of the Japanese encephalitis virus serogroup. The nucleic acid primers that can be a component of the kits of the invention are extensively described in Section 3.1, above, while the nucleic acid probes that can be a component of the kits of the invention are described in Section 3.2, above. The probes can optionally be labeled as described above. In certain embodiments, the kits comprise a thermostable DNA polymerase. In certain embodiments, the thermostable DNA polymerase has reverse transcription activity. In certain embodiments, the kits comprise instructions for detecting a nucleic acid of a detectable flavivirus according to the methods of the invention. In other embodiments, the kits comprise instructions for detecting a member of the Japanese encephalitis virus serogroup. In other embodiments, the kits comprise one or more containers to hold the components of the kit.

In certain embodiments, the kits can contain a composition comprising a primer of the invention. The kits can also contain a composition comprising a probe of the invention. The kits can further contain a composition comprising a thermostable DNA polymerase. In some embodiments, the thermostable DNA polymerase is selected from the group of *Carboxydothermus hydrogenformans* DNA polymerase, *Thermosipho africanus* DNA polymerase, *Bacillus pallidus* DNA polymerase, *Thermus* species Z05 DNA polymerase, *Thermus aquaticus* DNA polymerase, *Thermus thermophilus* DNA polymerase, *Thermatoga maritima* DNA polymerase, *Thermatoga neapolitana* DNA polymerase and *Thermus* sps17 DNA polymeraseThe compositions comprising a primer or probe of the invention or a thermostable DNA polymerase can further comprise additional reagents. For example, the compositions can comprise suitable preservatives prevent degradation of the composition, suitable buffers to modulate the pH of the composition, suitable diluents to alter the viscosity of the compositions, and the like.

The kits can additionally comprise other reagents for carrying out a 5' nuclease reactions, as described above. In addition, the kits can comprise reagents to facilitate the detection of a fragmented probe that indicates the presence of a nucleic acid of a Japanese encephalitis virus serogroup member. Kits that can be used to detect a nucleic acid of defined sequence are described in U.S. Pat. Nos. 6,514,736, 6,197,563, 6,040,166, and 5,641,864, each of which is incorporated herein by reference in its entirety. One of skill in the art can easily use the primers and probes of the invention to modify the disclosures of these U.S. patents to design additional kits that are also within the scope of the present invention.

EXAMPLES

Example 1

Amplification and Detection of West Nile Virus RNA

A lysate of virus-infected cell culture supernatant was received from Dr. R. Lanciotti of the Centers for Disease Control and Prevention. Nucleic acids were purified from the lysate using reagents from the QIAamp Viral RNA Mini Kit (Qiagen Inc., Valencia, Calif.) according to the manufacturer's instructions. Serial 10-fold dilutions ($10^{-2}$-$10^{-7}$) of the purified nucleic acids were made. Fifty microliters of each dilution were amplified in 5' nuclease reaction assays using TaqMan® reagents and methods by RT-PCR in 100 µl reactions containing 1 µM primers (each of SEQ ID NO:8 and SEQ ID NO:15), 55 mM Tricine (pH 7.7), 450 µM dNTPs (each of dATP, dCTP, dGTP, and dUTP), 2.7 mM manganese acetate, 135 mM potassium acetate, 7% (v/v) DMSO, 6% (VN) glycerol, 5 units uracil-N-glycosylase, 40 units ZO5 DNA polymerase, and 0.15 µM probe (SEQ ID NO:28, labeled with FAM and CY5). Reverse transcription/PCR was performed in a COBAS TaqMan™ Instrument (Roche Diagnostics, Pleasanton, Calif.) using the following thermalcycling parameters: 4 minutes at 50° C.→30 minutes at 59° C.→2 cycles of 15 seconds at 95° C., 50 seconds at 58° C.→60 cycles of 15 seconds at 91° C., 50 seconds at 58° C.→2 minutes at 40° C. An example of the amplification results is shown in FIG. 6.

Various embodiments of the invention have been described. The descriptions and examples are intended to be illustrative of the invention rather than limiting. Indeed, it will be apparent to those of skill in the art that modifications may be made to the various embodiments of the invention described without departing from the spirit of the invention or scope of the appended claims set forth below.

Each reference cited herein is hereby incorporated by reference in its entirety.

SEQUENCE LISTING

<160> NUMBER OF SEQ ID NOS: 74

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence:region of
      conserved sequence in 3' untranslated region of
      the genomes of flaviviruses

<400> SEQUENCE: 1
gtaagccctc agaaccgtct cggaa 25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence:complement to SEQ ID NO:1

<400> SEQUENCE: 2
ttccgagacg gttctgaggg cttac 25

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence:Japanese encephalitis virus serogroup Primer 1
<220> FEATURE:
<221> NAME/KEY: modified_base
<222> LOCATION: (8)
<223> OTHER INFORMATION: n = t or absent

<400> SEQUENCE: 3
gwaasccnsy crramcysyy tcggrw 26

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence:West Nile virus Primer 1
<220> FEATURE:
<221> NAME/KEY: modified_base
<222> LOCATION: (8)
<223> OTHER INFORMATION: n = t or absent

<400> SEQUENCE: 4
gtaagccncy cagaaccgyy tcggaa 26

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence:Japanese encephalitis virus Primer 1
<220> FEATURE:
<221> NAME/KEY: modified_base
<222> LOCATION: (8)
<223> OTHER INFORMATION: n = absent

<400> SEQUENCE: 5

```
gaaasccnct crraacygty tcggaa                                             26

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence:Murray
      Valley encephalitis virus Primer 1

<400> SEQUENCE: 6
gaaagcctcc cagamccgty tcggaa                                             26

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence:Koutango
      virus Primer 1

<400> SEQUENCE: 7
gtaagccctc agaaccgtct cggaa                                              25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence:Example
      Primer 1

<400> SEQUENCE: 8
gtaagccctc agaaccgtct cggaa                                              25

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence:region of
      conserved sequence in 3' untranslated region of
      the genomes of flaviviruses

<400> SEQUENCE: 9
tctcctagtc tatcccaggt gtcaa                                              25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence:complement
      to SEQ ID NO:9

<400> SEQUENCE: 10
agaggatcag atagggtcca cagtt                                              25

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence:Japanese
      encephalitis virus serogroup Primer 2
<220> FEATURE:
<221> NAME/KEY: modified_base
```

```
<222> LOCATION: (11)
<223> OTHER INFORMATION: n = t or absent

<400> SEQUENCE: 11
yccyastmtw nyyccaggtr tcaa                                              24

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence:West Nile
      virus Primer 2

<400> SEQUENCE: 12
ycctagtcta tcccaggtrt caa                                               23

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence:Japanese
      encephalitis virus Primer 2

<400> SEQUENCE: 13
cccyastmta tyyccaggtg tcaa                                              24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence:Murray
      Valley encephalitis virus Primer 2

<400> SEQUENCE: 14
tcctagtctt ttcccaggtg tcaa                                              24

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence:Example
      Primer 2

<400> SEQUENCE: 15
tcctagtcta tcccaggtgt caa                                               23

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence:region of
      conserved sequence in 3' untranslated region of
      the genomes of flaviviruses

<400> SEQUENCE: 16
ggactagagg ttagaggaga ccccgcgg                                          28

<210> SEQ ID NO 17
<211> LENGTH: 28
<212> TYPE: DNA
<213> ORGANISM: Artificial Sequence
<220> FEATURE:
```

```
<223> OTHER INFORMATION: Description of Artificial Sequence:complement
      of SEQ ID NO:16

<400> SEQUENCE: 17
ccgcggggtc tcctctaacc tctagtcc                                              28

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence:probe for
      detecting flaviviruses
<220> FEATURE:
<221> NAME/KEY: modified_base
<222> LOCATION: (25)
<223> OTHER INFORMATION: n = g, c, t, a or absent
<220> FEATURE:
<221> NAME/KEY: modified_base
<222> LOCATION: (26)
<223> OTHER INFORMATION: n = c, t, g or absent
<220> FEATURE:
<221> NAME/KEY: modified_base
<222> LOCATION: (27)
<223> OTHER INFORMATION: n = g, c, a, t or absent
<220> FEATURE:
<221> NAME/KEY: modified_base
<222> LOCATION: (28)
<223> OTHER INFORMATION: n = g, c, a, t or absent

<400> SEQUENCE: 18
ggwctagwgg ttagaggaga cccynnnn                                              28

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence:probe for
      detecting Japanese encephalitis virus serogroup
      members

<400> SEQUENCE: 19
ggactagwgg ttagaggaga ccccrykk                                              28

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence:probe for
      detecting West Nile virus

<400> SEQUENCE: 20
ggactagwgg ttagaggaga ccccrcgk                                              28

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence:probe for
      detecting Japanese encephalitis virus

<400> SEQUENCE: 21
ggactagagg ttagaggaga ccccgygg                                              28

<210> SEQ ID NO 22
<211> LENGTH: 28
```

```
<212> TYPE: DNA
<213> ORGANISM: Artificial Sequence
<220> FEATURE:
<223> OTHER INFORMATION: Description of Artificial Sequence:probe for
      detecting Murray Valley encephalitis virus

<400> SEQUENCE: 22
ggactagagg ttagaggaga ccccactc                                      28

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence:probe for
      detecting Kunjin virus

<400> SEQUENCE: 23
aataygtgga ttacatgast tcaytgaag                                     29

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence:probe for
      detecting Dengue virus

<400> SEQUENCE: 24
ggactagagg ttagaggaga ccccyssv                                      28

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence:probe for
      detecting yellow fever virus

<400> SEQUENCE: 25
ggtctagagg ttagaggaga ccctccag                                      28

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence:probe for
      detecting Montana myotis leukencephalitis virus

<400> SEQUENCE: 26
ggactagagg ttagaggaga ccccttcc                                      28

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence:probe for
      detecting Modoc virus

<400> SEQUENCE: 27
ggactagagg ttgagggaga cccccggc                                      28

<210> SEQ ID NO 28
<211> LENGTH: 28
<212> TYPE: DNA
```

<213> ORGANISM: Artificial Sequence
<220> FEATURE:
<223> OTHER INFORMATION: Description of Artificial Sequence:Example
      Probe 1

<400> SEQUENCE: 28
ggactagagg ttagaggaga ccccgcgg                                             28

<210> SEQ ID NO 29
<211> LENGTH: 418
<212> TYPE: DNA
<213> ORGANISM: Artificial Sequence
<220> FEATURE:
<223> OTHER INFORMATION: Description of Artificial Sequence:3'
      untranlated region of the genome of St. Louis encephalitis
      virus (SLEV) isolate BFS1750

<400> SEQUENCE: 29
ttgccaccgg atgtcaggta acggtgctg tctgtaacct ggccccaggt gactgggtta      60
tcaaagccaa tctggccgag tgcaaagccc ctcattccga ctcgggaggg tccctagcac    120
gtaggctgga gaggacgcaa aagtcagacc agaaatgcca cctgaaagca tgctaaaggt    180
gctgtctgta catgccccag gaggactggg ttaacaaagc ttaacagccc cagcggccca    240
aaccatggag tgcgtgacca tggcgtaagg actagaggtt agaggagacc ccgctgcaac    300
ttggcaaggc ccaaacccgc tcgaagctgt agagacgggg aaggactag aggttagagg     360 agacccctttg ccgttaacgc aaacaacagc atattgacac ctggaaagac aggagatc    418

<210> SEQ ID NO 30
<211> LENGTH: 342
<212> TYPE: DNA
<213> ORGANISM: Artificial Sequence
<220> FEATURE:
<223> OTHER INFORMATION: Description of Artificial Sequence:3'
      untranlated region of the genome of St. Louis encephalitis
      virus (SLEV) isolate 1750-Std

<400> SEQUENCE: 30
ttgccaccgg atgtcaggta acggtgctg tctgtaacct ggccccaggt gactgggtta      60
tcaaagccaa tctggccgag tgcaaagccc ctcattccga ctcgggaggg tccctagcac    120
gtaggctgga gaggacgcaa aagtcagacc agaaatgcca cctgaaagca tgctaaaggt    180
gctgtctgta catgccccag gaggactggg ttaacaaagc ttaacagccc cagcggccca    240
aaccatggag tgcgtgacca tggcgtaagg actagaggtt agaggagacc ccgcgcaact    300
tggcaaggcc caaacccgct cgaagctgta gagacggggg aa                       342

<210> SEQ ID NO 31
<211> LENGTH: 418
<212> TYPE: DNA
<213> ORGANISM: Artificial Sequence
<220> FEATURE:
<223> OTHER INFORMATION: Description of Artificial Sequence:3'
      untranlated region of the genome of St. Louis encephalitis
      virus (SLEV) isolate TD6-4G

<400> SEQUENCE: 31
ttgccaccgg atgtcaggta acggtgctg cctgtaacct ggccccaggt gactgggtta      60
tcaaagccaa tctggccgag tgcaaagccc ctcattccga ctcgggaggg tccctggcac    120
gtaggctgga gaggacgcaa aagtcagacc agaaatgcca cctgaaagca tgctaaaggt    180
gctgtctgta catgccccag gaggactggg ttaacaaagc ttaacagccc cagcggccca    240

```
aaccatggag tgcgtgacca tggcgtaagg actagaggtt agaggagacc ccgctgcaac      300
tcggcaaggc ccaaacccgc tcgaagctgt agagatgggg aaggactag aggttagagg       360 agaccccttg ccgttaacgc aaacaacagc atattgacac ctggaaagac aggagatc       418
```

<210> SEQ ID NO 32
<211> LENGTH: 342
<212> TYPE: DNA
<213> ORGANISM: Artificial Sequence
<220> FEATURE:
<223> OTHER INFORMATION: Description of Artificial Sequence:3'
      untranlated region of the genome of St. Louis encephalitis
      virus (SLEV) isolate CoaV750

<400> SEQUENCE: 32

```
ttgccaccgg atgtcaggta acggtgctg cctgtaacct ggccccaggt gactgggtta       60
ccaaagccaa tctggctgag tgcaaagccc ctcgttccga ttcgggaggg tccctggcac      120
gtaggctgga gaggacgcaa aagtcagacc agaaatgcca cctgaaagca tgctaaaggt     180
gctgtctgta catgccccag gaggactggg ttaacaaagc ttaacagccc cagcggccca     240
aaccatggag tgcgtgacca tggcgtaagg actagaggtt agaggagacc ccgcgcaact     300
tggcaaggcc aaaacccgct cgaagctgta gagatggggg aa                       342
```

<210> SEQ ID NO 33
<211> LENGTH: 418
<212> TYPE: DNA
<213> ORGANISM: Artificial Sequence
<220> FEATURE:
<223> OTHER INFORMATION: Description of Artificial Sequence:3'
      untranlated region of the genome of St. Louis encephalitis
      virus (SLEV) isolate L695121.05

<400> SEQUENCE: 33

```
ttgccaccgg atgtcaggta acggtgctg tctgtaacct ggccccaggt gactgggtta       60
tcaaagccaa tccggctggg tgcaaagccc ctcattccga ctcgggaggg tccctggcat     120
gtaggctgga gaggacgcac aagtcagacc agaaatgcca cctgaaagca tgctaaaggt    180
gctgtctgta catgccccag gaggactggg ttaacaaagc ttaacagccc cagcggccca     240
aaccatggag tgcgtgacca tggcgtaagg actagaggtt agaggagacc ccgctgtaac    300
ttggcaaggc ccaaacccgc tcgaagctgt agagacgggg aaggactag aggttagagg      360 agaccccttg ccgttaacgc aaacaacagc atattgacac ctggaaagac aggagatc       418
```

<210> SEQ ID NO 34
<211> LENGTH: 418
<212> TYPE: DNA
<213> ORGANISM: Artificial Sequence
<220> FEATURE:
<223> OTHER INFORMATION: Description of Artificial Sequence:3'
      untranlated region of the genome of St. Louis encephalitis
      virus (SLEV) isolate TNM771K
<220> FEATURE:
<221> NAME/KEY: modified_base
<222> LOCATION: (384)
<223> OTHER INFORMATION: n = g, a, c or t

<400> SEQUENCE: 34

```
ttgccaccgg atgtcaggta acggtgctg tctgtaacct ggccccaggt gactgggtca       60
tcaaagccaa tctggctggg tgcaaagccc ctcattccga ctcgggaggg tccctggcac     120
gtaggctgga gaggacgcac aagtcagacc agaaatgcca cctgaaagca tgctaaaggt    180
gctgtctgta catgccccag gaggactggg ttaacaaagc ttaacagccc cagcggccca     240
```

```
aaccatggag agcgtgacca tggcgtaagg actagaggtt agaggagacc ccgctgtaac    300
ttggcaaggc ccaaacccgc tcgaagctgt agagacgggg aaggactag  aggttagagg    360 agacccttg  ccgttaacgc aaanaacagc atattgacac ctggaaagac aggagatc     418

<210> SEQ ID NO 35
<211> LENGTH: 418
<212> TYPE: DNA
<213> ORGANISM: Artificial Sequence
<220> FEATURE:
<223> OTHER INFORMATION: Description of Artificial Sequence:3'
      untranlated region of the genome of St. Louis encephalitis
      virus (SLEV) isolate MSI-7

<400> SEQUENCE: 35
ttgccaccgg atgtcaggta acggtgctg  tctgtaacct ggccccaggc gactgggtta     60
tcaaagccaa tccggctggg tgcaaagccc ctcattccga ctcgggaggg tccctggcac    120
gtaggctgga gaggacgcac aagtcagacc agaaatgcca cctgaaagca tgctaaaggt    180
gctgtctgta catgccccag gaggactggg ttaacaaagc ttaacagccc cagcggccca    240
aaccatggag tgcgtgacca tggcgtaagg actagaggtt agaggagacc ccgctgtaac    300
ttggcaaggc ccaaacccgc tcaaagctgt agagacgggg aaggactag  aggttagagg    360 agacccttg  ccgttaacgc aaacaacagc atattgacac ctggaaagac aggagatc     418

<210> SEQ ID NO 36
<211> LENGTH: 405
<212> TYPE: DNA
<213> ORGANISM: Artificial Sequence
<220> FEATURE:
<223> OTHER INFORMATION: Description of Artificial Sequence:3'
      untranlated region of the genome of St. Louis encephalitis
      virus (SLEV) isolate Kern217

<400> SEQUENCE: 36
ccggatgtca ggtaaacggt gctgtctgta acctggcccc aggtcactgg gttatcaaag     60
ccaacccggc tggtgcaaa  gcccctcatt ccgactcggg agggtccctg gcacgtaggc    120
tggagaggac gcacaagtca gaccagaaat gccacctgaa agcatgctaa aggtgctgtc    180
tgtacatgcc ccaggaggac tgggttaaca aagcttaaca gccccagcgg cccaaaccat    240
ggagtgcgtg accatggcgt aaggactaga ggttagagga ccccgctg   taacttggca    300 aggcccaaac ccgctcaaag ctgtagagac ggggaaggac tagaggttag aggagaccc    360 cttgccgtta acgcaaacaa cagcatattg acacctggaa agaca                   405

<210> SEQ ID NO 37
<211> LENGTH: 375
<212> TYPE: DNA
<213> ORGANISM: Artificial Sequence
<220> FEATURE:
<223> OTHER INFORMATION: Description of Artificial Sequence:3'
      untranlated region of the genome of St. Louis encephalitis
      virus (SLEV) isolate CoaV608

<400> SEQUENCE: 37
cccaggcgac tgggttatca aagccaatcc ggctgggtgc aaagcccctc attccgactc     60
gggagggtcc ctggcacgta ggctggagag gacgcacaag tcagaccaga atgccacct    120 gaaagcatgc taaaggtgct gtctgtacat gccccaggag gactgggtta acaaagctta    180
acagccccag cggcccaaac catggagtgc gtgaccatgg cgtaaggact agaggttaga    240
```

-continued

```
ggagacccg ctgtaacttg gcaaggccca aacccgctca aagctgtaga gacgggggaa    300
ggactagagg ttagaggaga cccttgccg ttaacgcaaa caacagcata ttgacacctg    360
gaaagacagg agatc                                                    375
```

<210> SEQ ID NO 38
<211> LENGTH: 411
<212> TYPE: DNA
<213> ORGANISM: Artificial Sequence
<220> FEATURE:
<223> OTHER INFORMATION: Description of Artificial Sequence:3'
      untranlated region of the genome of St. Louis encephalitis
      virus (SLEV) isolate TBH-28

<400> SEQUENCE: 38

```
ttgccaccgg atgtcaggta aacggtgctg tctgtaacct ggccccaggt gactgggtta     60
tcaaagccaa cccggctggg tgcaaagccc ctcattccga ctcgggaggg tccctggcac    120
gtaggccgga gaggacgcac aagtcagacc agaaatgcca cctgaaagca tgctaaaggt    180
gctgtctgta catgccccag gaggactggg ttaacaaagc ttaacagccc cagcggccca    240
aaccatggag tgcgtgacca tggcgtaagg actagaggtt agaggagacc ccgctgtaat    300
ttggcaaggc ccaaacccgc tcgaagctgt agagacgggg aaggactag aggttagagg     360 agacccttg ccgttaacgc aaacaacagc atattgacac ctggaaagac a              411
```

<210> SEQ ID NO 39
<211> LENGTH: 402
<212> TYPE: DNA
<213> ORGANISM: Artificial Sequence
<220> FEATURE:
<223> OTHER INFORMATION: Description of Artificial Sequence:3'
      untranlated region of the genome of St. Louis encephalitis
      virus (SLEV) isolate VR1265

<400> SEQUENCE: 39

```
ccggaagtca ggtaaacggt gctgtctgta acctggcccc aggtgactgg ttatcaaag     60 ccaatctggc tggtgcaaa gcccctcatt ccgactcggg agggtccctg cacgtaggc    120 tggagcggac gcacaagtca gaccagaaat gccacctgaa agcatgctaa aggtgctgtc   180
tgtacatgcc ccaggaggac tgggttaaca agcttaaca gccccagcgg cccaaaccat   240
ggagtgcgtg accatggcgt aaggactaga ggttagagga ccccgctg taacttggca    300 aggcccaaac ccgctcgaag ctgtagagac ggggaagga ctagaggtta gaggagaccc    360
cttgccgtca acgcaaacaa cagcatattg acacctggaa ag                      402
```

<210> SEQ ID NO 40
<211> LENGTH: 374
<212> TYPE: DNA
<213> ORGANISM: Artificial Sequence
<220> FEATURE:
<223> OTHER INFORMATION: Description of Artificial Sequence:3'
      untranlated region of the genome of St. Louis encephalitis
      virus (SLEV) isolate CoAV353

<400> SEQUENCE: 40

```
cccaggtgac tgggttatca agccaatct agctgagtgc aaagcccctc attccgactc     60
gggagggtcc ctggcacgta ggctggagag acgcaaaag tcagaccaga atgccacct    120 gaaagcatgc taaaggtgct gtctgtacat gccccaggag gactgggtta acaaagctta   180
acagccccag cggcccaaac catggagtgc gtgaccatgg cgtaaggact agaggttaga   240 ggagacccg ctgcaacttg gcaaggccca aacccgctcg aagctgtaga gacgggggaa   300
```
ggactagagg ttagaggaga ccccttgccg ttaacgcaaa caacagcata ttgacacctg        360
gaaagacagg agat                                                          374

<210> SEQ ID NO 41
<211> LENGTH: 27
<212> TYPE: DNA
<213> ORGANISM: Artificial Sequence
<220> FEATURE:
<223> OTHER INFORMATION: Description of Artificial Sequence:Dengue virus
      consensus upstream primer

<400> SEQUENCE: 41
gagccccgtc caaggacgta aaaagaa                                             27

<210> SEQ ID NO 42
<211> LENGTH: 27
<212> TYPE: DNA
<213> ORGANISM: Artificial Sequence
<220> FEATURE:
<223> OTHER INFORMATION: Description of Artificial Sequence:Dengue virus
      consensus upstream primer
<220> FEATURE:
<221> NAME/KEY: modified_base
<222> LOCATION: (27)
<223> OTHER INFORMATION: n = t-butyl-benzyl-dA

<400> SEQUENCE: 42
gagccccgtc caaggacgta aaaagan                                             27

<210> SEQ ID NO 43
<211> LENGTH: 27
<212> TYPE: DNA
<213> ORGANISM: Artificial Sequence
<220> FEATURE:
<223> OTHER INFORMATION: Description of Artificial Sequence:Dengue virus
      consensus upstream primer
<220> FEATURE:
<221> NAME/KEY: modified_base
<222> LOCATION: (26)
<223> OTHER INFORMATION: n = methyl-dA
<220> FEATURE:
<221> NAME/KEY: modified_base
<222> LOCATION: (27)
<223> OTHER INFORMATION: n = t-butyl-benzyl-dA

<400> SEQUENCE: 43
gagccccgtc caaggacgta aaaagnn                                             27

<210> SEQ ID NO 44
<211> LENGTH: 27
<212> TYPE: DNA
<213> ORGANISM: Artificial Sequence
<220> FEATURE:
<223> OTHER INFORMATION: Description of Artificial Sequence:Dengue virus
      type I upstream primer

<400> SEQUENCE: 44
gagccccgtc caaggacgta aaatgaa                                             27

<210> SEQ ID NO 45
<211> LENGTH: 27
<212> TYPE: DNA
<213> ORGANISM: Artificial Sequence
<220> FEATURE:
<223> OTHER INFORMATION: Description of Artificial Sequence:Dengue virus
      type I upstream primer
<220> FEATURE:
<221> NAME/KEY: modified_base

```
<222> LOCATION: (27)
<223> OTHER INFORMATION: n = t-butyl-benzyl-dA

<400> SEQUENCE: 45
gagccccgtc caaggacgta aaatgan                                              27

<210> SEQ ID NO 46
<211> LENGTH: 27
<212> TYPE: DNA
<213> ORGANISM: Artificial Sequence
<220> FEATURE:
<223> OTHER INFORMATION: Description of Artificial Sequence:Dengue virus
      type I upstream primer
<220> FEATURE:
<221> NAME/KEY: modified_base
<222> LOCATION: (26)
<223> OTHER INFORMATION: n = methyl-dA
<220> FEATURE:
<221> NAME/KEY: modified_base
<222> LOCATION: (27)
<223> OTHER INFORMATION: n = t-butyl-benzyl-dA

<400> SEQUENCE: 46
gagccccgtc caaggacgta aaatgnn                                              27

<210> SEQ ID NO 47
<211> LENGTH: 27
<212> TYPE: DNA
<213> ORGANISM: Artificial Sequence
<220> FEATURE:
<223> OTHER INFORMATION: Description of Artificial Sequence:Dengue virus
      types II and III upstream primer

<400> SEQUENCE: 47
gagccccgtc caaggacgtt aaagaa                                               27

<210> SEQ ID NO 48
<211> LENGTH: 27
<212> TYPE: DNA
<213> ORGANISM: Artificial Sequence
<220> FEATURE:
<223> OTHER INFORMATION: Description of Artificial Sequence:Dengue virus
      types II and III upstream primer
<220> FEATURE:
<221> NAME/KEY: modified_base
<222> LOCATION: (27)
<223> OTHER INFORMATION: n = t-butyl-benzyl-dA

<400> SEQUENCE: 48
gagccccgtc caaggacgtt aaaagan                                              27

<210> SEQ ID NO 49
<211> LENGTH: 27
<212> TYPE: DNA
<213> ORGANISM: Artificial Sequence
<220> FEATURE:
<223> OTHER INFORMATION: Description of Artificial Sequence:Dengue virus
      types II and III upstream primer
<220> FEATURE:
<221> NAME/KEY: modified_base
<222> LOCATION: (26)
<223> OTHER INFORMATION: n = methyl-dA
<220> FEATURE:
<221> NAME/KEY: modified_base
<222> LOCATION: (27)
<223> OTHER INFORMATION: n = t-butyl-benzyl-dA

<400> SEQUENCE: 49
gagccccgtc caaggacgtt aaaagnn                                              27
```

```
<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence:Dengue virus
      type IV upstream primer

<400> SEQUENCE: 50
attgaagtca ggccacttgt gcca                                          24

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence:Dengue virus
      type IV upstream primer
<220> FEATURE:
<221> NAME/KEY: modified_base
<222> LOCATION: (24)
<223> OTHER INFORMATION: n = t-butyl-benzyl-dA

<400> SEQUENCE: 51
attgaagtca ggccacttgt gccn                                          24

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence:Dengue virus
      type IV upstream primer
<220> FEATURE:
<221> NAME/KEY: modified_base
<222> LOCATION: (23)
<223> OTHER INFORMATION: n = ethyl-dC
<220> FEATURE:
<221> NAME/KEY: modified_base
<222> LOCATION: (24)
<223> OTHER INFORMATION: n = t-butyl-benzyl-dA

<400> SEQUENCE: 52
attgaagtca ggccacttgt gcnn                                          24

<210> SEQ ID NO 53
<211> LENGTH: 25
<212> TYPE: DNA
<213> ORGANISM: Artificial Sequence
<220> FEATURE:
<223> OTHER INFORMATION: Description of Artificial Sequence:Dengue virus
      downstream primer

<400> SEQUENCE: 53
gatctctggt ctttcccagc gtcaa                                         25

<210> SEQ ID NO 54
<211> LENGTH: 25
<212> TYPE: DNA
<213> ORGANISM: Artificial Sequence
<220> FEATURE:
<223> OTHER INFORMATION: Description of Artificial Sequence:Dengue virus
      downstream primer
<220> FEATURE:
<221> NAME/KEY: modified_base
<222> LOCATION: (25)
<223> OTHER INFORMATION: n = t-butyl-benzyl-dA

<400> SEQUENCE: 54
```

```
gatctctggt ctttcccagc gtcan                                              25
```

<210> SEQ ID NO 55
<211> LENGTH: 25
<212> TYPE: DNA
<213> ORGANISM: Artificial Sequence
<220> FEATURE:
<223> OTHER INFORMATION: Description of Artificial Sequence:Dengue virus
      downstream primer
<220> FEATURE:
<221> NAME/KEY: modified_base
<222> LOCATION: (24)
<223> OTHER INFORMATION: n = methyl-dA
<220> FEATURE:
<221> NAME/KEY: modified_base
<222> LOCATION: (25)
<223> OTHER INFORMATION: n = t-butyl-benzyl-dA

<400> SEQUENCE: 55

```
gatctctggt ctttcccagc gtcnn                                              25
```

<210> SEQ ID NO 56
<211> LENGTH: 28
<212> TYPE: DNA
<213> ORGANISM: Artificial Sequence
<220> FEATURE:
<223> OTHER INFORMATION: Description of Artificial Sequence:yellow fever
      virus upstream primer

<400> SEQUENCE: 56

```
aaccgggata aaaactacgg gtggagaa                                           28
```

<210> SEQ ID NO 57
<211> LENGTH: 28
<212> TYPE: DNA
<213> ORGANISM: Artificial Sequence
<220> FEATURE:
<223> OTHER INFORMATION: Description of Artificial Sequence:yellow fever
      virus upstream primer
<220> FEATURE:
<221> NAME/KEY: modified_base
<222> LOCATION: (28)
<223> OTHER INFORMATION: n = t-butyl-benzyl-dA

<400> SEQUENCE: 57

```
aaccgggata aaaactacgg gtggagan                                           28
```

<210> SEQ ID NO 58
<211> LENGTH: 28
<212> TYPE: DNA
<213> ORGANISM: Artificial Sequence
<220> FEATURE:
<223> OTHER INFORMATION: Description of Artificial Sequence:yellow fever
      virus upstream primer
<220> FEATURE:
<221> NAME/KEY: modified_base
<222> LOCATION: (27)
<223> OTHER INFORMATION: n = methyl-dA
<220> FEATURE:
<221> NAME/KEY: modified_base
<222> LOCATION: (28)
<223> OTHER INFORMATION: n = t-butyl-benzyl-dA

<400> SEQUENCE: 58

```
aaccgggata aaaactacgg gtggagnn                                           28
```

<210> SEQ ID NO 59
<211> LENGTH: 26
<212> TYPE: DNA
<213> ORGANISM: Artificial Sequence

```
<220> FEATURE:
<223> OTHER INFORMATION: Description of Artificial Sequence:yellow fever
      virus upstream primer

<400> SEQUENCE: 59
ataaaaacta cgggtggaga accgga                                              26

<210> SEQ ID NO 60
<211> LENGTH: 26
<212> TYPE: DNA
<213> ORGANISM: Artificial Sequence
<220> FEATURE:
<223> OTHER INFORMATION: Description of Artificial Sequence:yellow fever
      virus upstream primer
<220> FEATURE:
<221> NAME/KEY: modified_base
<222> LOCATION: (26)
<223> OTHER INFORMATION: n = t-butyl-benzyl-dA

<400> SEQUENCE: 60
ataaaaacta cgggtggaga accggn                                              26

<210> SEQ ID NO 61
<211> LENGTH: 24
<212> TYPE: DNA
<213> ORGANISM: Artificial Sequence
<220> FEATURE:
<223> OTHER INFORMATION: Description of Artificial Sequence:yellow fever
      virus downstream primer

<400> SEQUENCE: 61
actccggtct ttccctggcg tcaa                                                24

<210> SEQ ID NO 62
<211> LENGTH: 24
<212> TYPE: DNA
<213> ORGANISM: Artificial Sequence
<220> FEATURE:
<223> OTHER INFORMATION: Description of Artificial Sequence:yellow fever
      virus downstream primer
<220> FEATURE:
<221> NAME/KEY: modified_base
<222> LOCATION: (24)
<223> OTHER INFORMATION: n = t-butyl-benzyl-dA

<400> SEQUENCE: 62
actccggtct ttccctggcg tcan                                                24

<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence:yellow fever
      virus downstream primer
<220> FEATURE:
<221> NAME/KEY: modified_base
<222> LOCATION: (23)
<223> OTHER INFORMATION: n = methyl-dA
<220> FEATURE:
<221> NAME/KEY: modified_base
<222> LOCATION: (24)
<223> OTHER INFORMATION: n = t-butyl-benzyl-dA

<400> SEQUENCE: 63
actccggtct ttccctggcg tcnn                                                24

<210> SEQ ID NO 64
<211> LENGTH: 25
```

```
<212> TYPE: DNA
<213> ORGANISM: Artificial Sequence
<220> FEATURE:
<223> OTHER INFORMATION: Description of Artificial Sequence:St Louis
      encephalitis virus upstream primer

<400> SEQUENCE: 64
caaagcccct cattccgact cggga                                            25

<210> SEQ ID NO 65
<211> LENGTH: 25
<212> TYPE: DNA
<213> ORGANISM: Artificial Sequence
<220> FEATURE:
<223> OTHER INFORMATION: Description of Artificial Sequence:St Louis
      encephalitis virus upstream primer
<220> FEATURE:
<221> NAME/KEY: modified_base
<222> LOCATION: (25)
<223> OTHER INFORMATION: n = t-butyl-benzyl-dA

<400> SEQUENCE: 65
caaagcccct cattccgact cgggn                                            25

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence:St Louis
      encephalitis virus upstream primer

<400> SEQUENCE: 66
tctcctgtct ttccaggtgt caa                                              23

<210> SEQ ID NO 67
<211> LENGTH: 23
<212> TYPE: DNA
<213> ORGANISM: Artificial Sequence
<220> FEATURE:
<223> OTHER INFORMATION: Description of Artificial Sequence:St Louis
      encephalitis virus upstream primer
<220> FEATURE:
<221> NAME/KEY: modified_base
<222> LOCATION: (23)
<223> OTHER INFORMATION: n = t-butyl-benzyl-dA

<400> SEQUENCE: 67
tctcctgtct ttccaggtgt can                                              23

<210> SEQ ID NO 68
<211> LENGTH: 23
<212> TYPE: DNA
<213> ORGANISM: Artificial Sequence
<220> FEATURE:
<223> OTHER INFORMATION: Description of Artificial Sequence:St.Louis
      encephalitis virus (SLEV) first primer complement

<400> SEQUENCE: 68
ttgacacctg gaaagacagg aga                                              23

<210> SEQ ID NO 69
<211> LENGTH: 24
<212> TYPE: DNA
<213> ORGANISM: Artificial Sequence
<220> FEATURE:
<223> OTHER INFORMATION: Description of Artificial Sequence:St.Louis
      encephalitis virus (SLEV) second primer
```

```
<400> SEQUENCE: 69
caaagcccct cattccgact cggg                                              24

<210> SEQ ID NO 70
<211> LENGTH: 30
<212> TYPE: DNA
<213> ORGANISM: Artificial Sequence
<220> FEATURE:
<223> OTHER INFORMATION: Description of Artificial Sequence:flavivirus
      anti-sense probe

<400> SEQUENCE: 70
gggtctcctc taacctctag tccttcccccc                                       30

<210> SEQ ID NO 71
<211> LENGTH: 98
<212> TYPE: DNA
<213> ORGANISM: Artificial Sequence
<220> FEATURE:
<223> OTHER INFORMATION: Description of Artificial Sequence:region of
      conserved sequence in 3' untranslated region of
      the genome of flavivirus AF196835

<400> SEQUENCE: 71 caacccccagg aggactgggt gaacaaagcc gcgaagtgat ccatgtaagc cctcagaacc      60
gtctcggaag gaggacccca catgttgtaa cttcaaag                               98

<210> SEQ ID NO 72
<211> LENGTH: 105
<212> TYPE: DNA
<213> ORGANISM: Artificial Sequence
<220> FEATURE:
<223> OTHER INFORMATION: Description of Artificial Sequence:region of
      conserved sequence in 3' untranslated region of
      the genome of flavivirus AF196835

<400> SEQUENCE: 72
tgactgaagc tgtaggtcag gggaaggact agaggttagt ggagaccccg tgccacaaaa      60
caccacaaca aaacagcata ttgacacctg ggatagacta ggaga                      105

<210> SEQ ID NO 73
<211> LENGTH: 121
<212> TYPE: DNA
<213> ORGANISM: Artificial Sequence
<220> FEATURE:
<223> OTHER INFORMATION: Description of Artificial Sequence:region of
      conserved sequence in 3' untranslated region of
      the genome of flavivirus AF196835

<400> SEQUENCE: 73
cagggcgaaa ggactagagg ttagaggaga ccccgcggtt taaagtgcac ggcccagcct      60
gactgaagct gtaggtcagg ggaaggacta gaggttagtg gagaccccgt gccacaaaac     120
a                                                                     121

<210> SEQ ID NO 74
<211> LENGTH: 25
<212> TYPE: DNA
<213> ORGANISM: Artificial Sequence
<220> FEATURE:
<223> OTHER INFORMATION: Description of Artificial Sequence:Example
      Primer 2
```

-continued

```
<400> SEQUENCE: 74
tctcctagtc tatcccaggt gtcaa                                              25
```

What is claimed is:

1. A kit for the detection of a nucleic acid of a member of the Japanese encephalitis virus serogroup, comprising:

a) a first oligonucleotide that comprises SEQ ID NO.:4;

b) a second oligonucleotide that comprises SEQ ID NO:12; and c) a detectably-labeled third oligonucleotide that comprises SEQ ID NO:20, wherein the first and second oligonucleotide lengths are from 25 to 100 nucleotides, and the third oligonucleotide length is from 28 to 100 nucleotides.

2. The kit of claim 1, wherein the first oligonucleotide comprises SEQ ID NO:8.

3. The kit of claim 1, wherein the third oligonucleotide comprises SEQ ID NO:28.

4. The kit of claim 1, wherein:

the first oligonucleotide comprises SEQ ID NO:8;

the second oligonucleotide comprises SEQ ID NO:12; and the third oligonucleotide comprises SEQ ID NO:28.

5. The kit of claim 1, wherein:

the first oligonucleotide comprises SEQ ID NO:8;

the second oligonucleotide comprises SEQ ID NO:74; and the third oligonucleotide comprises SEQ ID NO:28.

6. The kit of claim 2, wherein the residue at position 24 of SEQ ID NO.:8 is N6-alkyl-deoxyadenosine.

7. The kit of claim 6, wherein the residue at position 24 of SEQ ID NO.:8 is N6-methyl-deoxyadenosine.

8. The kit of claim 2, wherein the residue at position 25 of SEQ ID NO.:8 is N6-alkyl-deoxyadenosine.

9. The kit of claim 8, wherein the residue at position 25 of SEQ ID NO.:8 is N6-tert-butylbenzyl-deoxyadenosine.

10. The kit of claim 2, wherein the residue at position 24 of SEQ ID NO.:8 is N6-methyldeoxyadenosine and the residue at position 25 of SEQ ID NO.:8 is N6-tert-butyl-benzyldeoxyadenosine.

11. The kit of claim 1, wherein the second oligonucleotide comprises SEQ ID NO.:15.

12. The kit of claim 11, wherein the residue at position 23 of SEQ ID NO.:15 is N6-alkyl-deoxyadenosine.

13. The kit of claim 11, wherein the residue at position 23 of SEQ ID NO.:15 is N6-alkyldeoxyadenosine.

14. The kit of claim 11, wherein the second oligonucleotide comprises SEQ ID NO.:74.

15. The kit of claim 14, wherein the residue at position 25 of SEQ ID NO.:74 is N6-alkyldeoxyadenosine.

16. The kit of claim 14, wherein the residue at position 25 of SEQ ID NO.:74 is N6-tertbutyl-benzyl-deoxyadenosine.

17. The kit of claim 1, wherein the detectably-labeled third oligonucleotide comprises SEQ ID NO.:28.

18. The kit of claim 17, wherein the detectablylabeled third oligonucleotide comprises a fluorescent moiety.

19. The kit of claim 18, wherein the detectably-labeled third oligonucleotide further comprises a quencher moiety.

20. The kit of claim 18, wherein the fluorescent moiety is selected from the group consisting of fluorescein-family dyes, polyhalofluorescein-family dyes, hexachlorofluorescein-family dyes, coumarin-family dyes, rhodamine-family dyes, cyanine-family dyes, oxazine-family dyes, thiazine-family dyes, squaraine family dyes, chelated lanthanide-family dyes, and BODIPY®-family dyes.

21. The kit of claim 18, wherein the fluorescent moiety is 6-carboxyfluorescein.

22. The kit of claim 19, wherein the quencher moiety is selected from the group consisting of fluorescein-family dyes, polyhalofluorescein-family dyes, hexachlorofluorescein-family dyes, coumarin-family dyes, rhodamine-family dyes, cyanine-family dyes, oxazine-family dyes, thiazine-family dyes, squaraine family dyes, chelated lanthanide-family dyes, BODIPY®-family dyes, and nonfluorescent quencher moieties.

23. The kit of claim 22, wherein the non-fluorescent quencher moiety is BHQ™-family dyes, Iowa Black™, or Dabcyl.

24. The kit of claim 19, wherein the quencher moiety is Cy5™.

25. The kit of claim 1, additionally comprising a thermostable DNA polymerase.

26. The kit of claim 25, wherein the thermostable DNA polymerase is selected from the group of Carboxydothermus hydrogenformans DNA polymerase, Thermosipho africanus DNA polymerase, Bacillus pallidus DNA polymerase, Thermus species Z05 DNA polymerase, Thermus aquatidus DNA polymerase, Thermus thermophilus DNA polymerase, Thermatoga maritima DNA polymerase, Thermatoga neapolitana DNA polymerase, and Thermus sps 17 DNA polymerase.

27. The kit of claim 1, additionally comprising instructions for detecting a nucleic acid of a member of the Japanese encephalitis virus serogroup.

* * * * *